(12) United States Patent
Coppola et al.

(10) Patent No.: US 8,741,575 B2
(45) Date of Patent: Jun. 3, 2014

(54) METHODS OF PREDICTING HIGH GRADE GLIOMAS USING SENESCENCE ASSOCIATED GENES

(75) Inventors: Domenico Coppola, Tampa, FL (US); Dung-Tsa Chen, Tampa, FL (US); Steven Brem, Haverford, PA (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 13/597,753

(22) Filed: Aug. 29, 2012

(65) Prior Publication Data
US 2012/0322687 A1    Dec. 20, 2012

Related U.S. Application Data

(63) Continuation of application No. PCT/US2011/027400, filed on Mar. 7, 2011.

(60) Provisional application No. 61/310,989, filed on Mar. 5, 2010.

(51) Int. Cl.
*C12Q 1/68* (2006.01)
*A61K 49/00* (2006.01)

(52) U.S. Cl.
USPC .......................................... 435/6.14; 424/9.1

(58) Field of Classification Search
None
See application file for complete search history.

(56) References Cited

U.S. PATENT DOCUMENTS

| 7,705,120 B2 * | 4/2010 | Lillie et al. ................. 530/350 |
| 2008/0102451 A1 * | 5/2008 | Lesniewski et al. .............. 435/6 |
| 2010/0167939 A1 | 7/2010 | Aldape et al. |

FOREIGN PATENT DOCUMENTS

| JP | 2006262841 A | 10/2006 |
| WO | 0018907 A2 | 4/2000 |
| WO | 2004053157 A2 | 6/2004 |
| WO | 2007017065 A2 | 2/2007 |
| WO | 2007026895 A1 | 3/2007 |

OTHER PUBLICATIONS

Noushmehr, H. et al. 2010. Identification of a CpG island methylator phenotype that defines a distinct subgroup of glioma. Cancer Cell. vol. 17, 510-522.

Schoenberg, B.S. (1983) Epidemiology of central nervous system tumor. In: Walker, M.D., editor. Oncology of the Nervous System. Boston: Nijhoff; p. 1-30.

Levin et al., (1989) Neoplasms of the central nervous system. In: Devita, V. et al. editors. Cancer: Principles and Practice of Oncology. 3rd edition, Philadelphia, PA.: Lippincott; p. 1557-1611.

Kleihues, P. et al., (1999) Primary and secondary glioblastomas: from concept to clinical diagnosis. Neuro-Oncol. pp. 44-51.

Bao, S. et al. 2006. Glioma stem cells promote radioresistance by preferential activation of the DNA damage response. Nature. vol. 444, pp. 756-760.

Cockett et al., (2000) Applied genomics: integration of the technology within pharmaceutical research and development. Current Opinion in Biotechnology. vol. 11, pp. 602-609.

Chen D.T. et al., Proliferative genes dominate malignancy-risk gene signature in histologically-normal breast tissue. Breast Cancer Res Treat. Jan. 2010; vol. 119, Issue 2, pp. 335-346.

Miller, R. and Siegmund, D. (1982) Maximally selected Chi square statistics. Biometrics vol. 38, pp. 1011-1016.

Lausen, B. and Schumacher, M. (1996) Evaluating the effect of optimized cutoff values in the assessment of prognostic factors. Computational Statistics and Data Analysis, vol. 21, pp. 307-326.

Benjamini, Y., and Hochberg, Y. (1995). Controlling the false discovery rate: a practical and powerful approach to multiple testing. Journal of the Royal Statistical Society Series B, vol. 57, No. 1, pp. 289-300.

The Children's Brain Tumor Foundation Internet Site; the American Brain Tumor Association Internet Site. http://www.cbtf.org. Accessed on Nov. 29, 2012.

International Search Report for PCT/US2011/027400 mailed on Nov. 28, 2011.

* cited by examiner

*Primary Examiner* — Jim Ketter
(74) *Attorney, Agent, or Firm* — Michele L. Lawson; Smith & Hopen, P.A.

(57) ABSTRACT

The present invention relates to biomarkers for neoplasias such as high grade gliomas. The inventors have discovered that the overexpression of senescence associated genes (SAG) is associated with a poor prognosis in subjects with high grade gliomas. The present invention provides SAG biomarkers for predicting response to therapy for subjects having high grade glioma based on dividing the samples into high and low risk groups; diagnosing high grade glioma; monitoring progression of high grade glioma from one biological state to another; and determining efficacy of treatment for high grade gliomas.

21 Claims, 52 Drawing Sheets

METHODS OF PREDICTING HIGH GRADE GLIOMAS USING SENESCENCE ASSOCIATED GENES

CROSS REFERENCE TO RELATED APPLICATIONS

This application is a continuation of and claims priority to International Patent Application No. PCT/US11/27400, entitled "Methods of Predicting High Grade Gliomas Using Senescence Associated Genes," filed on Mar. 7, 2011 which is a non-provisional of and claims priority to U.S. provisional patent application No. 61/310,989, with the same title, filed on Mar. 5, 2010 of which are hereby incorporated by reference into this disclosure.

FIELD OF INVENTION

This invention relates to tumorigenic assays. Specifically, the invention provides a method of determining high grade gliomas using biomarkers.

BACKGROUND OF THE INVENTION

Glial derived tumors or "gliomas" are transformed cells that display increased metabolic activity as a result of the transformation process. Gliomas comprise a diverse group of neoplasms that differ in their morphology, their CNS location, their degree of invasiveness, their tendency for progression, and their growth characteristics. Neoplastic transformation can occur in all glial types which allow the production of a large variety of pathological and morphological variants. Most primary brain tumors derived from glial cells have lost growth control regulation which gives rise to astrocytomas, glioblastomas, or oligodendrocytomas.

The most important determinant of survival for gliomas is the "grade" of the glioma. The low grade gliomas are easier to treat while the high grade gliomas (anaplastic astrocytoma and glioblastoma) are much more difficult to successfully treat. High grade gliomas account for about 30% of primary brain tumors in adults and are the second most common cause of cancer death in children under age 15. (The Children's Brain Tumor Foundation Internet Site; the American Brain Tumor Association Internet Site)

Gliomas have specific signs and symptoms that are primarily related to the location of the glioma. For example, gliomas found in the temporal lobe of the brain may cause epilepsy, difficulty with speech or loss of memory. Gliomas located in the frontal lobe may cause behavioral changes, weakness in the extremities, or difficulty with speech. Gliomas in the occipital lobe may cause loss of vision. Gliomas in the parietal lobe may cause loss of spatial orientation, diminished sensation on the opposite side of the body, or the inability to recognize once familiar objects or people.

The World Health Organization (WHO) has subdivided gliomas by histological grade. These grades are an indication of differentiation status, malignant potential, response to treatment, and survival. (Noushmehr, H. et al. 2010. Identification of a CpG island methylator phenotype that defines a distinct subgroup of glioma. *Cancer Cell*. Vol. 17:510-522) Increasing grade indicates increasing malignancy and decreasing differentiation, which is associated with increased mitotic activity and enhanced cell migration. Grades are classified from Grade I through Grade IV.

Grade I gliomas are generally slow growing, exhibit few mitotic features and are characterized by most cells having normal characteristics. Grade II gliomas have an increased number of cells with polymorphic nuclei in mitosis and there is no clear line of demarcation from normal cells. High grade gliomas are divided by grade into two categories: anaplastic astrocytomas (Grade III) and glioblastoma multiforme (Grade IV). (Schoenberg, B. S. (1983) Epidemiology of central nervous system tumor. In: Walker, M. D., editor. *Oncology of the Nervous System*. Boston: Nijhoff; p. 1-30; Levin et al., (1989) Neoplasms of the central nervous system. In: Devita, S. et al. editors. *Cancer: Principles and Practice of Oncology*. 3$^{rd}$ edition, Philadelphia, Pa.: Lippincott; p. 1557-1611; Kleihues, P. et al., (1999) Primary and secondary glioblastomas: from concept to clinical diagnosis. *Neuro-Oncol.* 1:44-51)

Glioblastomas are Grade IV gliomas and are the most lethal primary brain tumor with a median survival of less than 12 months because of resistance to radiation and other treatments. (Bao, S. et al. 2006. Glioma stem cells promote radioresistance by preferential activation of the DNA damage response. *Nature*. Vol. 444:756-760) Most glioblastomas are diagnosed as de novo or primary tumors. These primary tumors exhibit cellular pleomorphism, vascular proliferation, mitoses, and multinucleated giant cells. Glioblastomas are more common in males than females. Approximately 5% of glioblastoma tumors are secondary tumors which progress from lower-grade tumors, such as grades II and III. These secondary tumors are usually seen in younger patients, are more evenly distributed between males and females, and exhibit longer survival times than primary tumors. (Noushmehr et al. 2010) Tumor cells of glioblastoma are the most undifferentiated among the brain tumors which allows the tumor cells to exhibit high potentials for migration and proliferation. Glioblastomas are highly invasive which contributes to the poor prognosis once onset occurs. Glioblastomas present as diffuse tumors with invasion into normal brain, but frequently recur or progress after radiation as focal masses, suggesting that only a fraction of tumor cells is responsible for regrowth. (Bao, S. et al. 2006)

The current method of diagnosing gliomas is through biopsy and evaluation of tissue histology. It would be highly desirable to have a biomarker for the detection of high grade gliomas. Furthermore, it would be highly desirable to have a screening methodology to evaluate the potential for successful therapy in subjects having high grade gliomas. Additionally, it would be highly desirable to have additional treatment regimens targeting the biochemical processes associated with high grade gliomas.

New prognostic and predictive markers are needed to accurately predict patient response to treatment, such as small molecule and biological molecule drugs. The classification of patient samples is crucial to cancer diagnosis and treatment. Associating a patient's response to treatment with molecular and genetic markers can elucidate new opportunities for treatment in non-responding patients or indicate one treatment over other treatment choices. By pre-selecting patients who are likely to respond well to an agent or combination therapy can reduce the number of patients needed in a clinical study or accelerate the time needed to complete a clinical development program (Cockett et al., Current Opinion in Biotechnology (2002) 11:602-609)

While it is known that the prognosis of high grade gliomas/ glioblastoma multiform worsens with age, the basis for this observation is unknown. It is also common knowledge that cellular senescence and tumorigenesis are related and involve emergence of genomic instability, alterations of the telomere, emergence of autophagy, and alterations in mitochondrial metabolism and energy-dependent signal transduction. Thus what is needed is a diagnostic marker for classifying subjects according to the prediction of response to therapy for subjects having high grade glioma; diagnosis of high grade glioma; monitoring progression of high grade glioma from one biological state to another; and efficacy of treatment for high grade glioma.

SUMMARY OF INVENTION

In one embodiment of the present invention a method of predicting the response of a subject to therapy for high grade glioma is presented. The method is comprised of: obtaining an expression level of at least one gene or gene expression product in a tumor sample; comparing the expression level of the at least one gene or gene expression product to a predetermined control expression level; and determining a therapeutic response based on the comparison of the expression level of the at least one gene or gene expression product obtained from the tumor sample to the predetermined control expression level. The method can further include the steps of obtaining a senescence score for the at least one gene or gene expression product and associating the senescence score with patient survival using statistical methods.

The at least one gene can be a senescence associated gene (SAG). The at least one gene expression product can be derived from an SAG. The at least one gene can be selected from the group consisting of CCL2, CCL7, CDKN1A, COPG, CSF2RB, CXCL1, ICAM1, IGFBP3, IL6, IL8, SAA4, TNFRSF11B, TNFSF11 and TP53. The high grade glioma can be selected from the group consisting of gliomas, astrocytomas, oligodendrogliomas, anaplastic oligodendrogliomas, and glioblastomas.

In another embodiment of the present invention, a method of diagnosing neoplasia is presented comprising: obtaining the expression levels of at least one senescence associated gene (SAG) or gene expression product in a sample and comparing the expression levels of the at least one SAG or gene expression product to a predetermined control level wherein an increase in the expression level of the at least one SAG or gene expression product over the predetermined control level indicates the presence of neoplasia.

The neoplasia can be a high grade glioma. The neoplasia can be selected from the group consisting of gliomas, astrocytomas, oligodendrogliomas, anaplastic oligodendrogliomas, glioblastomas, neuroblastomas, and meningiomas. The at least one gene can be selected from the group consisting of CCL2, CCL7, CDKN1A, COPG, CSF2RB, CXCL1, ICAM1, IGFBP3, IL6, IL8, SAA4, TNFRSF11B, TNFSF11 and TP53.

In a further embodiment of the present invention a method of monitoring neoplasia progression from one biological state to another in a tumor sample is presented comprising: detecting a first expression level of at least one gene or gene expression product in a tumor sample at a first timepoint; detecting a second expression level of the at least one gene or gene expression product in the tumor sample at a second time point wherein the second timepoint is at a given interval after the first timepoint; and comparing the first and the second expression levels wherein an increase in the second expression level as compared to the first expression level is indicative of neoplasia progression and a decrease in the second expression level as compared to the first expression level is indicative of neoplasia regression.

The neoplasia can be a high grade glioma. The neoplasia can be selected from the group consisting of gliomas, astrocytomas, oligodendrogliomas, anaplastic oligodendrogliomas, glioblastomas, neuroblastomas, and meningiomas. The at least one gene can be a senescence associated gene (SAG). The at least one gene expression product can be derived from an SAG. The at least one gene can be selected from the group consisting of CCL2, CCL7, CDKN1A, COPG, CSF2RB, CXCL1, ICAM1, IGFBP3, IL6, IL8, SAA4, TNFRSF11B, TNFSF11 and TP53.

Another embodiment of the present invention includes a method for evaluating the efficacy of an agent for modulating a senescence associated gene (SAG) comprising: detecting a first expression level of at least one senescence associated gene or gene expression product in a tumor sample at a first timepoint; administering the agent to the tumor sample; detecting a second expression level of the at least one senescence associated gene or gene expression product in the tumor sample at a second timepoint wherein the second timepoint is at a given interval after the first timepoint; and comparing the first expression level to the second expression level wherein a decrease in the second expression level as compared to the first expression level indicates the agent is efficacious for modulating the senescence associated gene. The at least one gene can be selected from the group consisting of CCL2, CCL7, CDKN1A, COPG, CSF2RB, CXCL1, ICAM1, IGFBP3, IL6, IL8, SAA4, TNFRSF11B, TNFSF11 and TP53.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
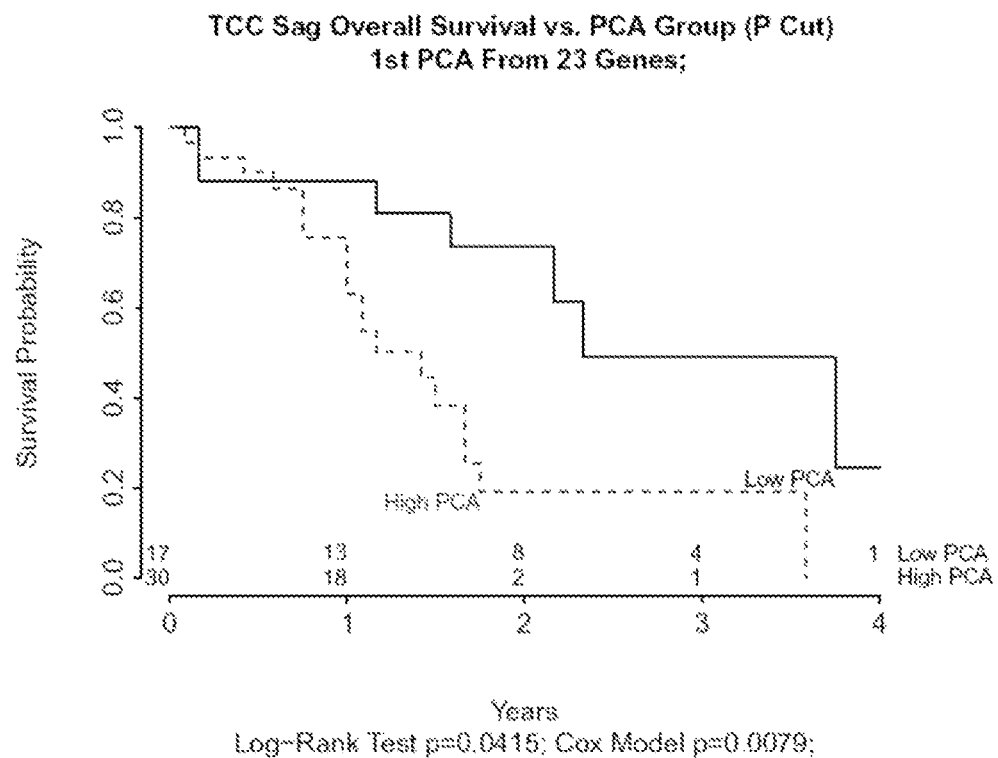
FIG. 1 is a Kaplan-Meier survival curve depicting two risk groups (high and low-risk) and showing significant separation of the two survival curves (median survival: 17 and 28 months, respectively, for high versus low senescence score).

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "agent" as used herein describes a composition, compound, chemical or extract that can be administered or tested by the present invention as a modulator of a senescence associated gene. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof "Agent" is used interchangeably herein with "compound", "composition", "chemical", "drug", and "extract".

"Subject" is used to describe an animal, preferably a human, to whom treatment is administered, including prophylactic treatment with the compositions of the present invention. "Subject" and "patient" are used interchangeably herein.

The genes of the present invention may serve as biomarkers for: (1) the diagnosis of disease; (2) the prognosis of diseases (e.g. monitoring disease progression or regression from one biological state to another); (3) the susceptibility or prediction of response to treatment for a disease; or (4) the evaluation of the efficacy to a treatment for disease. For the diagnosis of disease, the level of the specific gene in the subject can be compared to a baseline or control level in which if the level is above the control level, a certain disease is implicated. The prognosis of disease can be assessed by comparing the level of the specific gene biomarker at a first timepoint to the level of the biomarker at a second timepoint which occurs at a given interval after the first timepoint. The prediction of response to treatment for a disease can be determined by obtaining the level of a specific gene biomarker and correlating this level to an overall senescence score. The evaluation of the efficacy of the treatment for a disease can be assessed by comparing the level of the specific gene biomarker at a first timepoint before administration of the treatment to the level of the biomarker at a second timepoint which occurs at a specified interval after the administration of the treatment.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

Methods to measure protein/polypeptide expression levels of selected biomarkers in the present invention include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners.

The term "high grade glioma" as used herein refers to gliomas of Grade III or above. Generally, as the grade of the glioma increases, the chances of malignancy also increase and the survival rate decreases.

The terms "diagnosing" or "diagnosis" as used herein refers to the determination of whether a subject comprises a disease or condition such as cancer. "Diagnosing" can also refer to distinguishing one cancer from another.

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The terms "risk or susceptibility" as used herein refers to the determination as to whether a subject would or would not respond to a particular therapy such as chemotherapy, such as one or more alkylating agents; radiotherapy; adjuvant therapy; surgery; or a combination thereof in order to optimize therapy for an individual subject. Cancers that express biomarkers that are indicative of a more highly aggressive cancer or poor prognosis may be treated with more aggressive therapies.

The term "treatment" or "treating" as used herein refers to the ability to ameliorate, suppress, mitigate, or eliminate the clinical symptoms after the onset of a disease state. Treatment can include chemicals, such as chemotherapeutic agents or test compounds, and/or non-chemical treatment such as radiation, electrical pulses, and magnetic fields. An effective or successful treatment provides a clinically observable improvement.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a prepropeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include genes involved in cell cycle regulation, apoptosis, cell proliferation, and angiogenesis. More specifically, biomarkers of the present invention include senescence associated genes (SAG), specifically, IL6, IL8, TP53, CDKN1A, ICAM-1, TNFSF11, TNFRSF11B, CCL-2, CCL-7, IGFBP-3, CXCL1, SAA4, COPG, and CSF2RB.

The term "biological state" as used herein refers to the result of the occurrence of a series of biological processes. As the biological processes change relative to each other, the biological state also changes. One measurement of a biological state is the level of activity of biological variables such as biomarkers, parameters, and/or processes at a specified time or under specified experimental or environmental conditions. A biological state can include, for example, the state of an individual cell, a tissue, an organ, and/or a multicellular organism. A biological state can be measured in samples taken from a normal subject or a diseased subject thus measuring the biological state at different time intervals may indicate the progression of a disease in a subject. The biological state may include a state that is indicative of disease (e.g. diagnosis); a state that is indicative of the progression or regression of the disease (e.g. prognosis); a state that is indicative of the susceptibility (risk) of a subject to therapy for the disease; and a state that is indicative of the efficacy of a treatment of the disease.

The term "cell" or "cells" is used synonymously herein and refers to in vitro cultures of mammalian cells grown and maintained as known in the art, as well as biological samples obtained from tumor specimens or normal specimens in vivo.

The term "senescence" as used herein refers to the permanent cessation of DNA replication and cell growth that is not reversible by growth factors. This phenomenon can occur at the end of the proliferative lifespan of normal cells or in normal or tumor cells in response to cytotoxic drugs, DNA damage or other cellular insult. Senescence can be characterized by certain morphological features including, but not limited to, increased size, flattened morphology, increased granularity, and senescence-associated β-galactosidase activity (SA-β-gal).

A "senescence associated gene" or "SAG" as used herein refers to a gene which is modulated (either induced or repressed) when a cell expresses a senescent phenotype. Specific senescence associated genes utilized in the present invention include, but are not limited to, CCL2, CCL7, CDKN1A, COPG, CSF2RB, CXCL1, ICAM1, IGFBP3, IL6, IL8, SAA4, TNFRSF11B, TNFSF11 and TP53.

The terms "overall senescence score" as used herein refers to a number generated using the first principal component of principal component analysis to reflect the combined effect of the senescence-associated gene (SAG) signature. This number is a summation of the SAG and is based on the assigned weights of each gene (each senescence score). The senescence score is based on a weighted value that is generated using principal component analysis according to the methodology described in Chen D. T. et al., which is incorporated herein in its entirety by reference. (Chen D. T. et al., Proliferative genes dominate malignancy-risk gene signature in histologically-normal breast tissue. Breast Cancer Res Treat. 2010 January; 119(2):335-46)

The terms "SAG signature" as used herein refers to the specific pattern of gene modulation of senescence associated genes (SAG) in neoplasias, specifically high grade gliomas. This SAG signature is comprised of the 14 SAG utilized in this invention.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

A "therapeutically effective amount" as used herein is defined as concentrations or amounts of components which are sufficient to effect beneficial or desired clinical results, including, but not limited to, inhibiting neoplastic transformation of cells; inhibiting inappropriate cell growth; inhibiting the proliferation of neoplastic/cancerous cells; inducing apoptosis in neoplastic/cancerous cells; decreasing the level of an SAG in a sample; and enhancing the therapeutic effect of chemotherapy medications. Compositions of the present invention can be used to effect a favorable change in the condition whether that change is an improvement or a complete elimination of symptoms due to neoplasia/cancer. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing cancer treatment or enhancing cancer treatment without causing significant side effects or adverse reactions.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measurable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal (e.g. non-tumorous, not undergoing neoplastic transformation, not exhibiting inappropriate cell growth). In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease (e.g. tumorous, cancerous, exhibiting inappropriate cell growth). In other embodiments, the baseline level can be established from a previous sample from the subject being tested, so that the disease progression or regression of the subject can be monitored over time and/or the efficacy of treatment can be evaluated.

The term "neoplasia", "cancer", "tumor", "cancerous", and malignant" as used herein, refer to the physiological condition in mammals that is typically characterized by unregulated cell growth or the presence of tumors. Examples of cancer benefited by the present invention include, but are not limited to, tumors in neural tissue such as gliomas, oligodendrogliomas, glioblastomas, astrocytomas, anaplastic oligodendroglioma, neuroblastomas, neuroepitheliomatous tumors, meningiomas, and nerve sheath tumors.

The term "about" as used herein is not intended to limit the scope of the invention but instead encompass the specified material, parameter or step as well as those that do not materially affect the basic and novel characteristics of the invention.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications. It includes the recited sequences as well as their complementary sequences, which can be easily ascertained by those of ordinary skill in the art.

The term "nucleic acid" as used herein may be double-stranded, single-stranded, or contain portions of both double and single stranded sequence. If the nucleic acid is single-stranded, the sequence of the other strand is also identifiable and thus the definition includes the complement of the sequence disclosed.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

A "probe set" as used herein refers to a group of one or more polynucleotides that each selectively hybridize to the same target (for example, a specific genomic region or mRNA) that correlates with cancer diagnosis or prognosis. As such, a single "probe set" may comprise any number of different isolated polynucleotides that selectively hybridize to a given target. The probe sets used in the instant invention can be comprised of any number of probe sets from 1 probe set to 24 probe sets, including those numbers between 1 and 24.

While it is known that the prognosis of high grade gliomas/glioblastoma multiform worsens with age, the basis for this observation is unknown. It is also common knowledge that cellular senescence and tumorigenesis are related and involve emergence of genomic instability, alterations of the telomere, emergence of autophagy, and alterations in mitochondrial metabolism and energy-dependent signal transduction. The inventors demonstrate that overexpression of senescence associated genes (SAG) indicates a poorer prognosis.

The present invention is based upon the discovery that SAG levels are elevated in high grade gliomas. Furthermore, the prognosis of the subject to respond to treatment correlates with the level of SAG. Thus, in a first aspect, the present invention provides a method of predicting the response to high grade glioma therapy by assaying levels of SAG.

EXAMPLE 1

Materials and Methods

Frozen tumor samples from 47 patients of different ages (31 to 81 years) with the histologic diagnosis of HGG were macrodissected and arrayed on a custom version of the Affymetrix HG-U133+GeneChip.

A set of 14 known senescence-associated genes (SAGs) including CCL2, CCL7, CDKN1A, COPG, CSF2RB, CXCL1, ICAM1, IGFBP3, IL6, IL8, SAA4, TNFRSF11B, TNFSF11 and TP53 were examined. An overall senescence score was generated using the first principal component from principal component analysis to reflect the combined effect of the senescence-associated gene signature. The methods of using principal component analysis to obtain a gene signature score are the same as those described in Chen D. T. et al., which is incorporated herein in its entirety by reference. (Chen D. T. et al., Proliferative genes dominate malignancy-risk gene signature in histologically-normal breast tissue. Breast Cancer Res Treat. 2010 January; 119(2):335-46)

Pearson correlation and Cox proportional hazards regression were used to examine the association of each SAG and the senescence score with age at onset and overall patient survival. False discovery rate was used to adjust for multiple comparisons.

Statistical Methods:

Descriptive statistics were provided for demographic information including frequency for category data (e.g., gender) and range, median, and mean with standard deviation for continuous variables (e.g., age). The inventors examined clinical association of a predetermined set of 14 genes related to age, senescence-associated genes (SAGs), including IL6, IL8, TP53, CDKN1A, ICAM-1, TNFSF11, TNFRSF11B, CCL-2, CCL-7, IGFBP-3, CXCL1, SAA4, COPG, and CSF2RB. Expression levels of these SAGs were measured using a customized Affymetrix gene chip. A total of 23 probe sets were used with some SAGs having multiple probe sets. These probe sets are depicted in FIGS. 10-32 wherein one probe set is depicted for each set of figures. For example, FIG. 10a-d all depict probe set 1 which is comprised of the IL-6 gene.

An overall senescence score was generated using the first principal component from principal component analysis to reflect the combined effect of the SAG signature, as described above in the Chen reference. Spearman correlation and Cox proportional hazards model were used to examine the association of the senescent score with age at onset, grade, and overall survival. A maximal chi-square statistics with a corrected p value was used to dichotomize the senescence score into two risk groups (low and high) for comparing the two corresponding Kaplan-Meier survival curves (Miller, R. and Siegmund, D. (1982) Maximally selected Chi square statistics. *Biometrics* 48, 1011-1016; Lausen, B. and Schumacher, M. (1996) Evaluating the effect of optimized cutoff values in the assessment of prognostic factors. *Computational Statistics and Data Analysis* 21, 307-326). Linear regression was used to associate the data based on age.

The proportion of smallest and largest values that were not considered as potential cut-off values for the maximal chi-square statistics were 33% (⅓) and 67% (⅔), respectively. The cut-off value between the high and low risk groups was −0.927. Univariate analysis was also performed to examine individual gene effect. False discovery rate (FDR) was used to adjust for multiple comparisons (Benjamini, Y., and Hochberg, Y. (1995). Controlling the false discovery rate: a practical and powerful approach to multiple testing. *Journal of the Royal Statistical Society Series* B, 57, 289-300).

Demographic Statistics:

A total of 47 patients were in the study with 18 female (38%) and 29 male (62%). There were 4 patients (9%) with grade 2, 2 patients (4%) with grade 3, 39 patients (83%) with grade 4, and 2 patients (4%) with GS (gliosarcoma) grade. Distribution of age at diagnosis had a range from 31 to 81 years with a median of 54 years and a mean of 55 years with a standard deviation of 13. The median follow-up time was 14 months with 26 events (55%).

Figure 2:
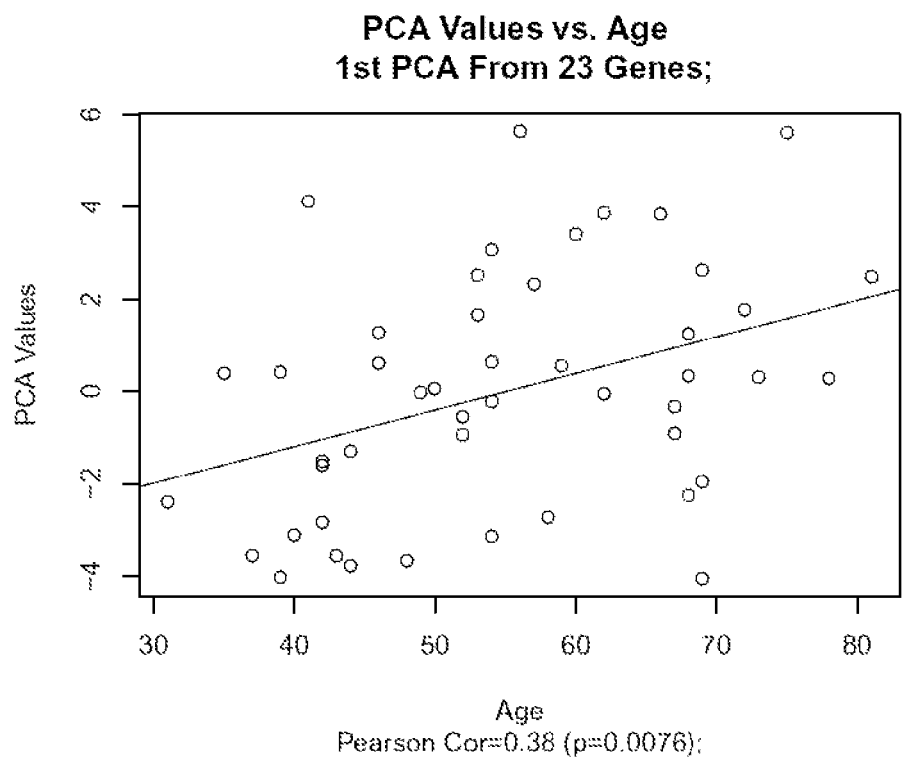
FIG. 2 is an image depicting an age-related gradient in the senescence score representation of the combined SAGs.

SAG Data Analysis:

The inventors used linear regression and found an age-related gradient in the senescence score representation of the combined SAGs (r=0.38; p=0.008; FIG. 2).

Moreover, the SAG signature was associated with poor prognosis (relative risk=1.22 with 95% confidence interval= (1.05, 1.42), and p=0.008 based on Cox proportional hazard model). A dichotomized senescence score using the maximal chi-square statistics yielded two risk groups (high and low-risk) and showed significant separation of the two survival curves (median survival: 17 and 28 months, respectively, for high versus low senescence score; p=0.04; FIG. 1). The cut-off for the two groups was −0.927. As shown in FIG. 1, patient survival time is greatly increased in the low-risk group as compared to the high-risk group.

Figure 3:
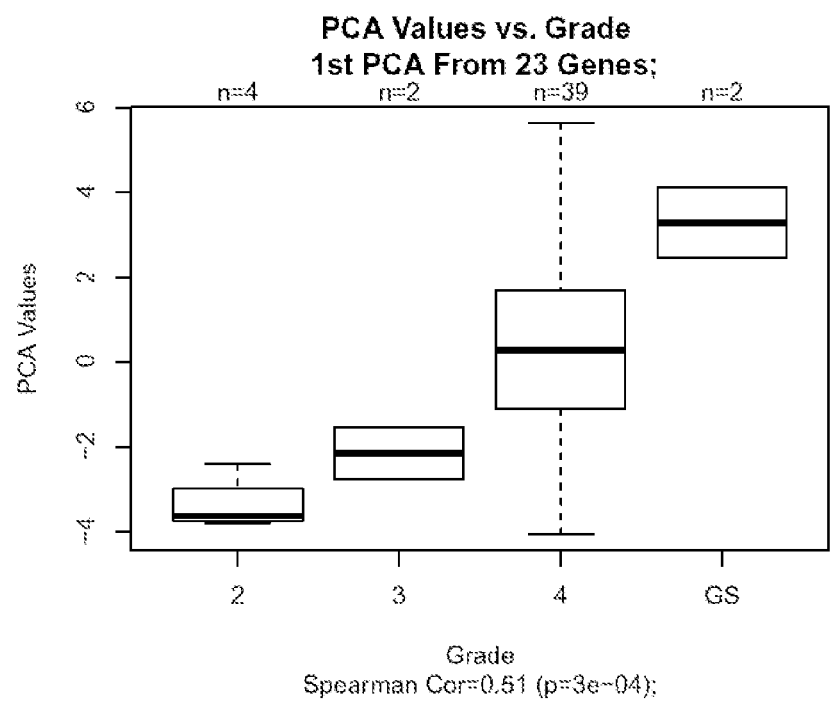
FIG. 3 is an image depicting SAG signature was positive correlated with grade with a higher score in patients with grade 4 and GS ($r=0.51$; $p=0.0003$).
Figure 4:
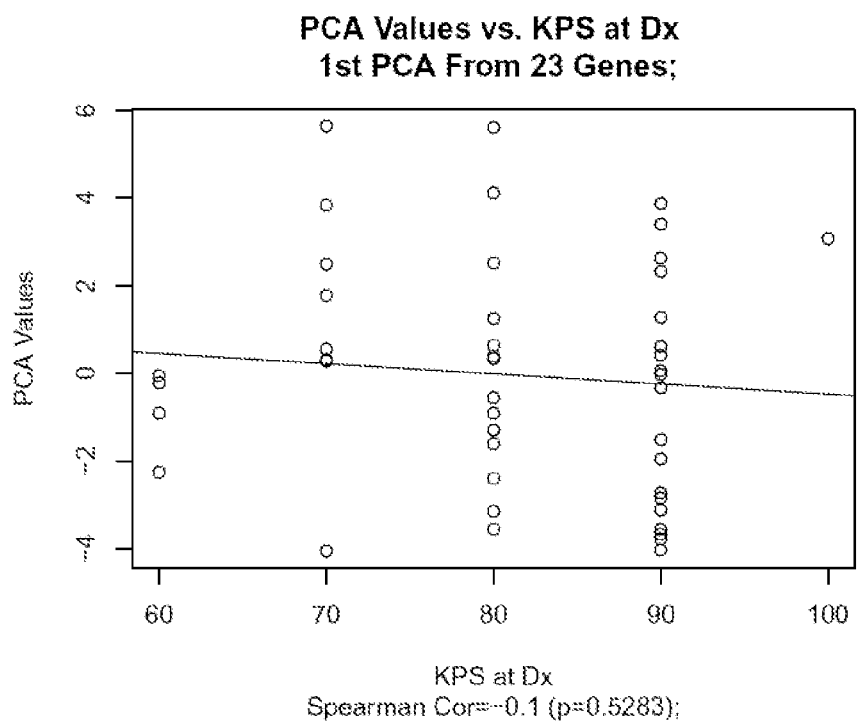
FIG. 4 is an image depicting principal component analysis (PCA) values versus KPS at Dx values.

FIG. 3 illustrates that the SAG signature was positively correlated with grade, with a higher score in patients with grade 4 and GS (r=0.51; p=0.0003; FIG. 3). As shown in FIG. 3, senescence scores between about −1 to about 4 were demonstrated in those subjects with high grade gliomas. The data in FIG. 3 can be used to diagnose the particular grade of tumor that is present in a subject.

Figure 5:
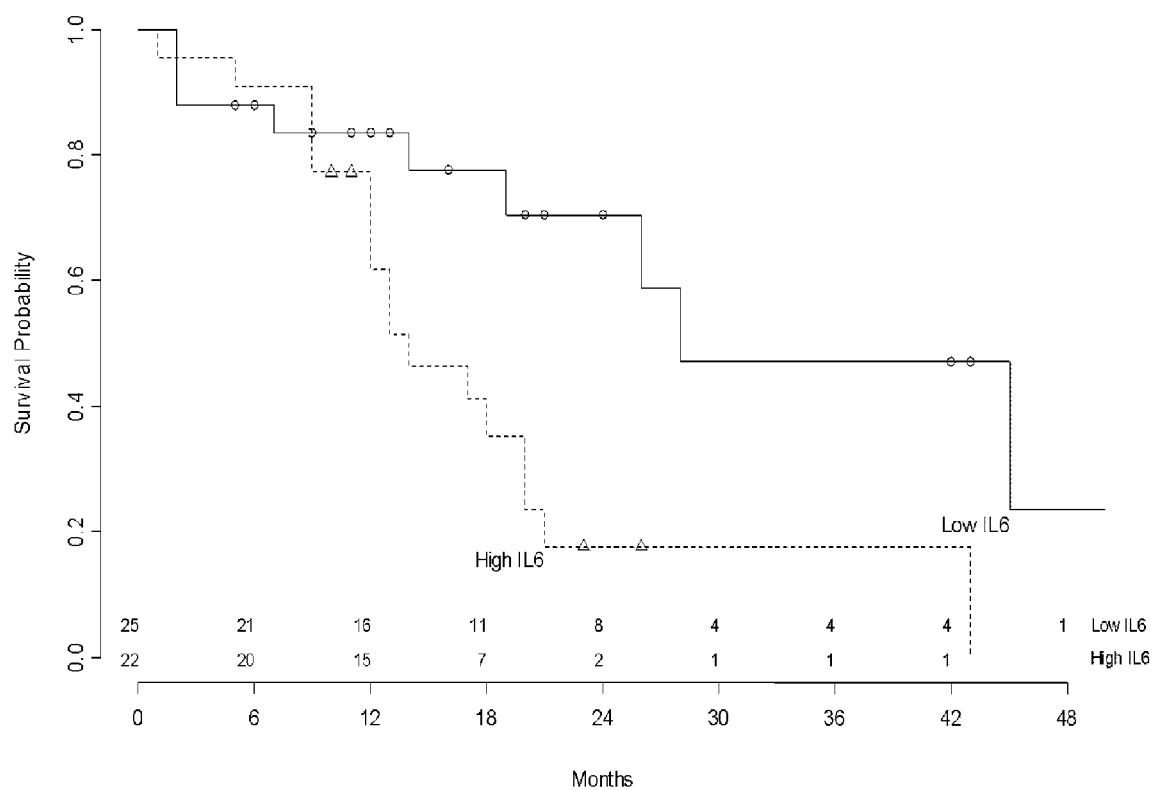
FIG. 5 is an image depicting that gene IL6 was significantly associated with patient survival. Gene IL6 had a median survival of 14 and 28 months, respectively, for high versus low senescence score with $p=0.046$.
Figure 6:
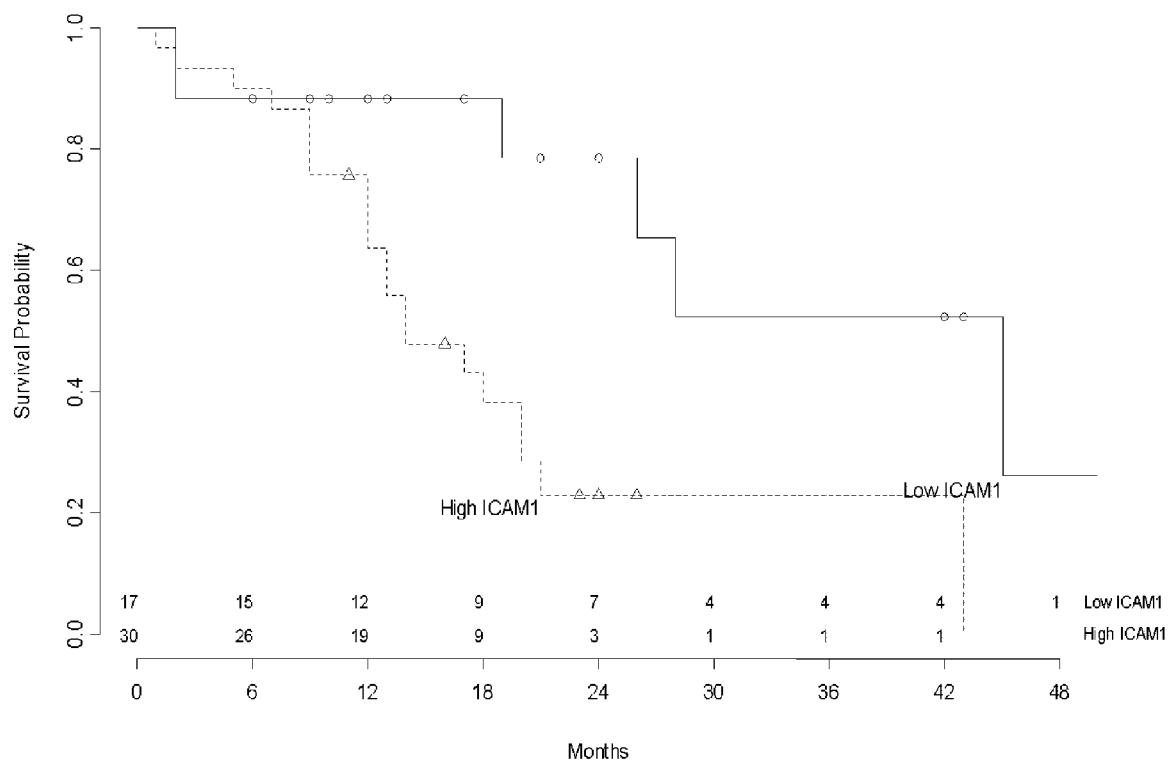
FIG. 6 is an image depicting that gene ICAM1 was significantly associated with patient survival. Gene ICAM1 had a median survival of 14 and 45 months, respectively, for high versus low senescence score with $p=0.04$.

Four SAGs were significantly associated with patient survival: IL6, ICAM1, COPG, and TNFSF11 at 5% FDR based on Cox proportional hazard model. Two of them (IL6 and ICAM1) had significant separation of survival curves by the maximal chi-square statistics. Specifically, gene IL6 had a median survival of 14 and 28 months, respectively, for high versus low senescence score with p=0.046 in FIG. 5 Similarly, gene ICAM1 had a median survival of 14 and 45 months, respectively, for high versus low senescence score with p=0.04 in FIG. 6

Figure 7:
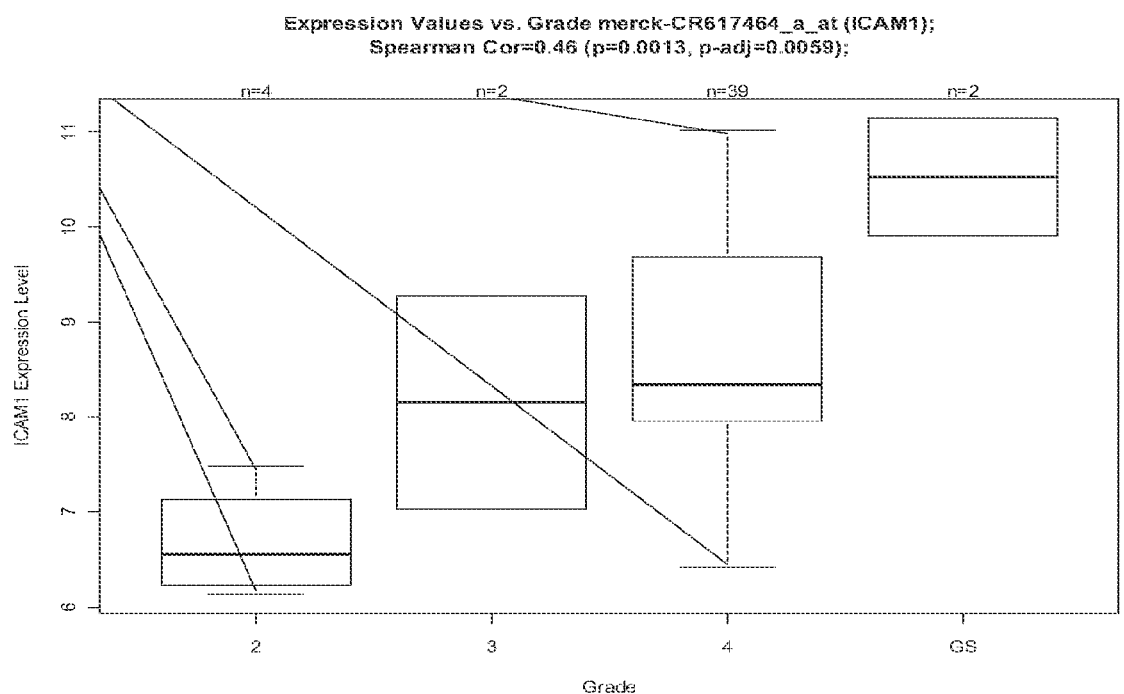
FIG. 7 is an image depicting that gene IL6 was significantly correlated with grade ($r=0.50$).
Figure 8:
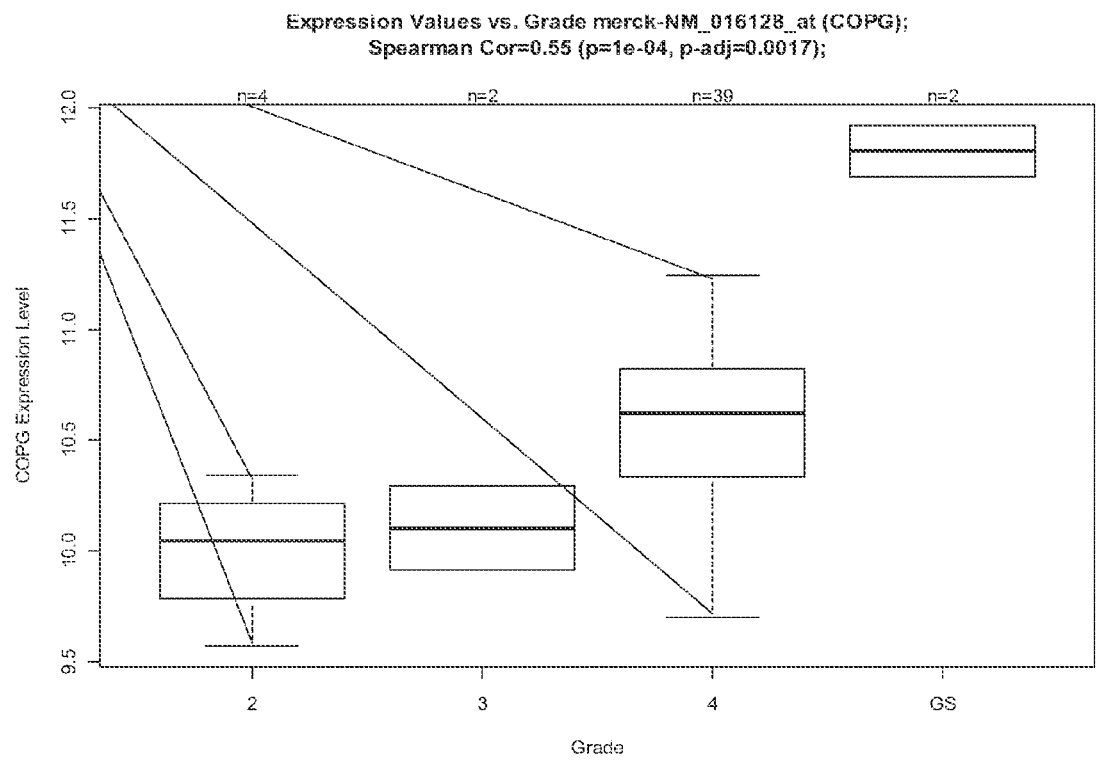
FIG. 8 is an image depicting that gene ICAM1 was significantly correlated with grade ($r=0.45$ and $0.46$).
Figure 9:
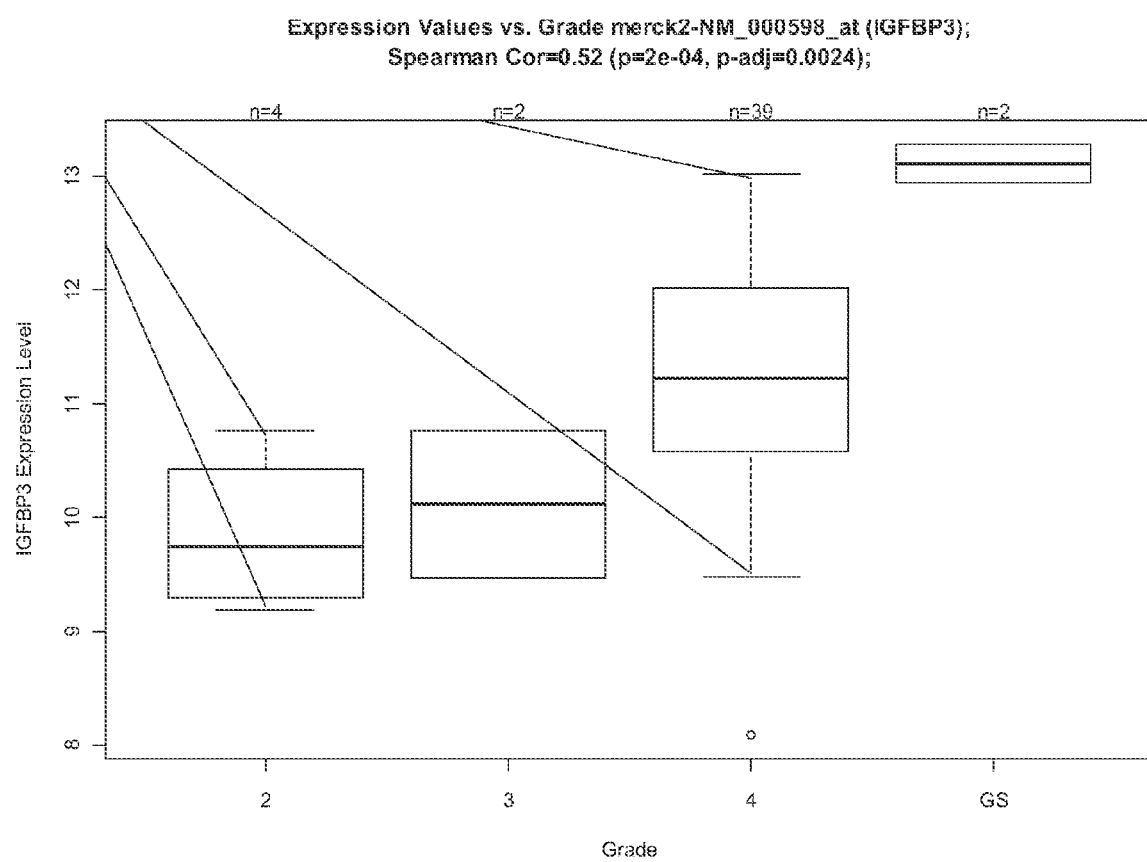
FIG. 9 is an image depicting that gene COPG was significantly correlated with grade ($r=0.55$).
Figure 10A:
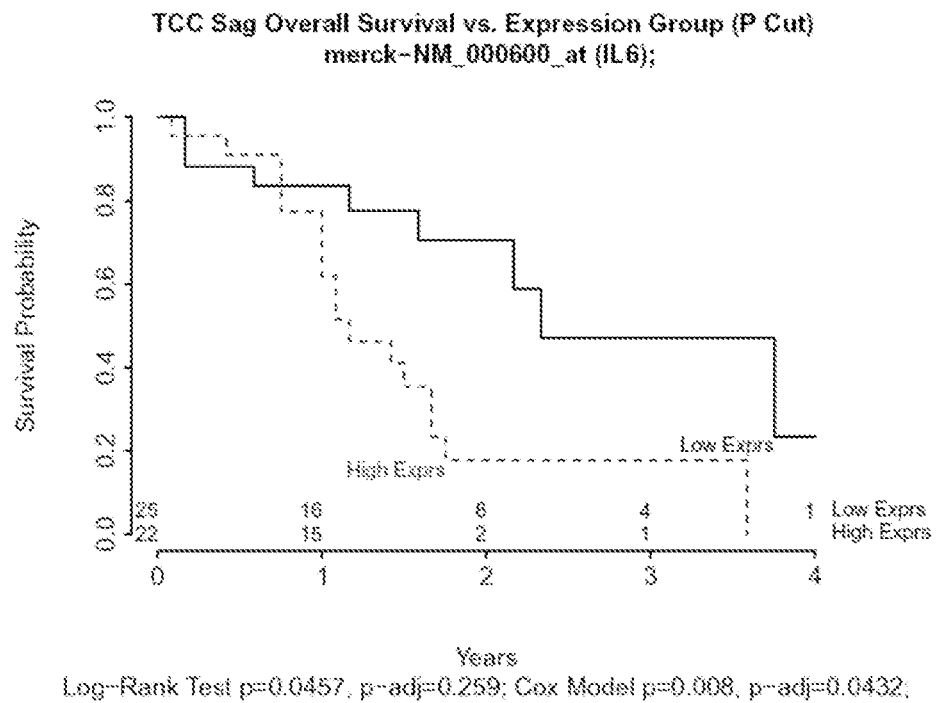
FIG. 10 is a series of images depicting the first probe set (Probe Set 1) (merck-NM_000600_ at IL6) containing the IL6 gene. (A) a Kaplan-Meier survival curve depicting two risk groups (high and low-risk) and showing significant separation of the two survival curves. (B) graph depicting expression values versus age for IL6. (C) graph depicting expression values versus grade for IL6. (D) graph depicting expression values versus KPS at Dx.
Figure 10B:
Figure 10C:
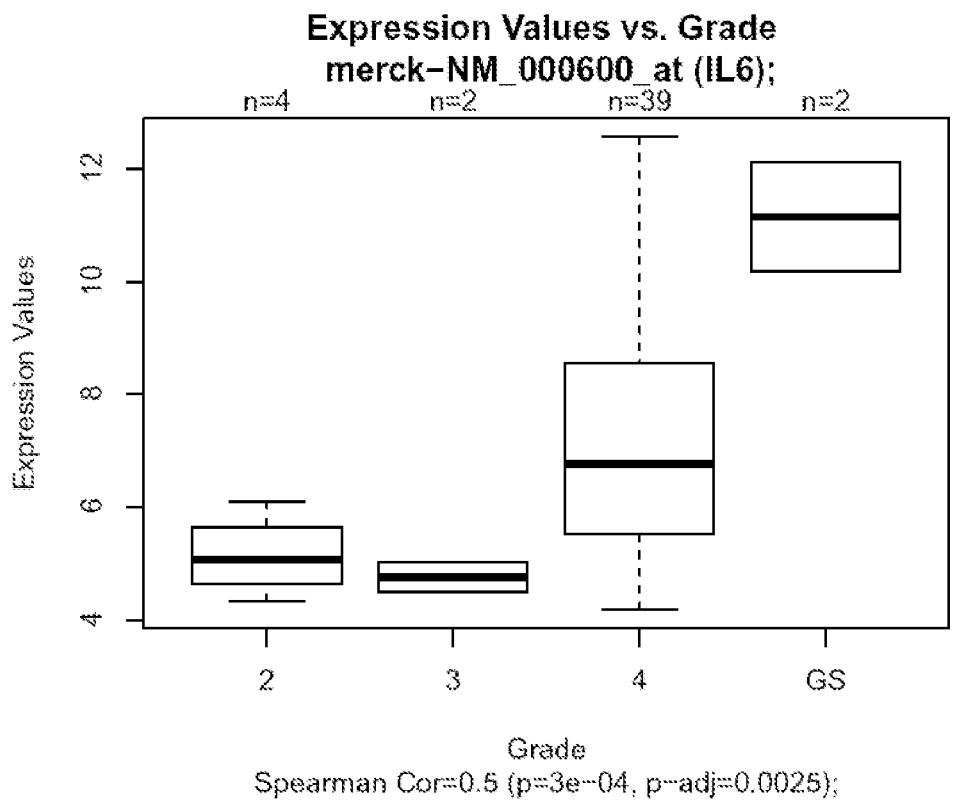
Figure 10D:
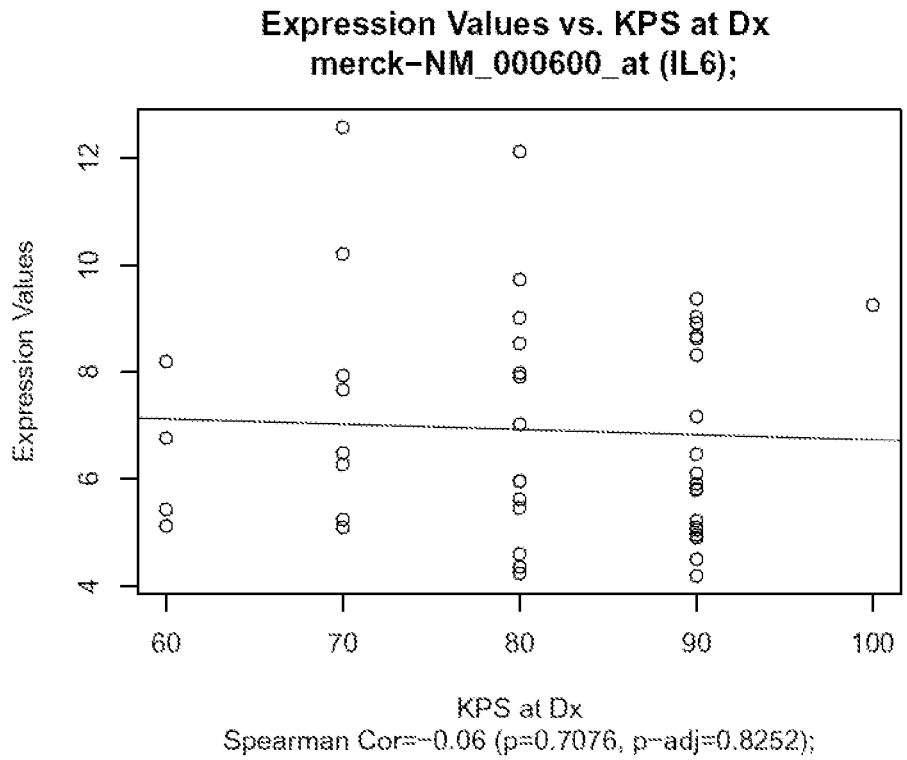
Figure 11A:
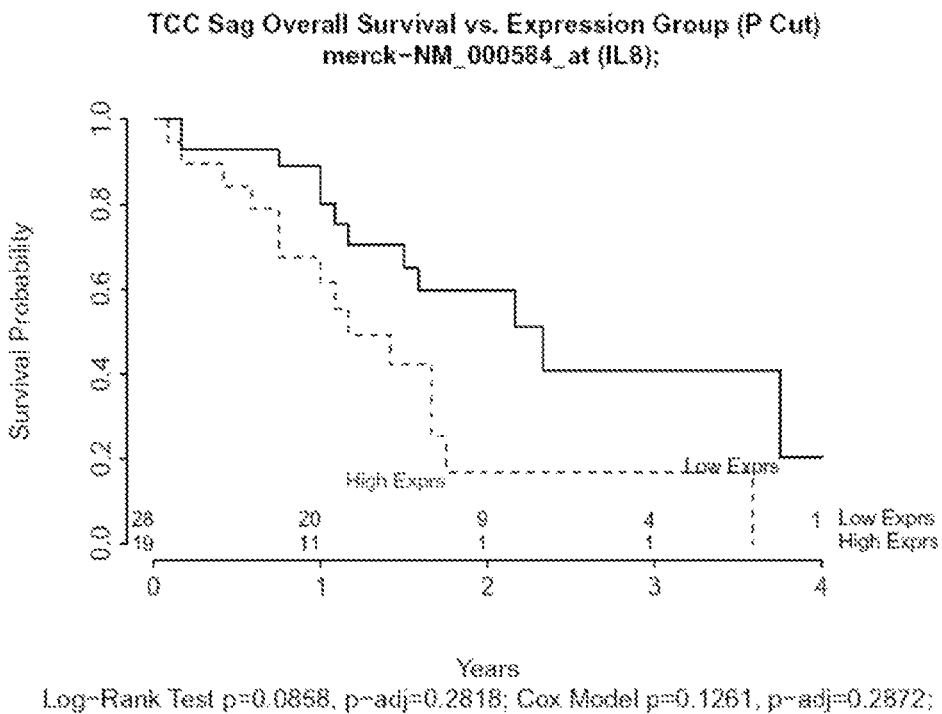
FIG. 11 is a series of images depicting the second probe set (Probe Set 2) (merck-NM_000584_at IL8) containing the IL8 gene. (A) a Kaplan-Meier survival curve depicting two risk groups (high and low-risk) and showing significant separation of the two survival curves. (B) graph depicting expression values versus age for IL8. (C) graph depicting expression values versus grade for IL8. (D) graph depicting expression values versus KPS at Dx.
Figure 11B:
Figure 11C:
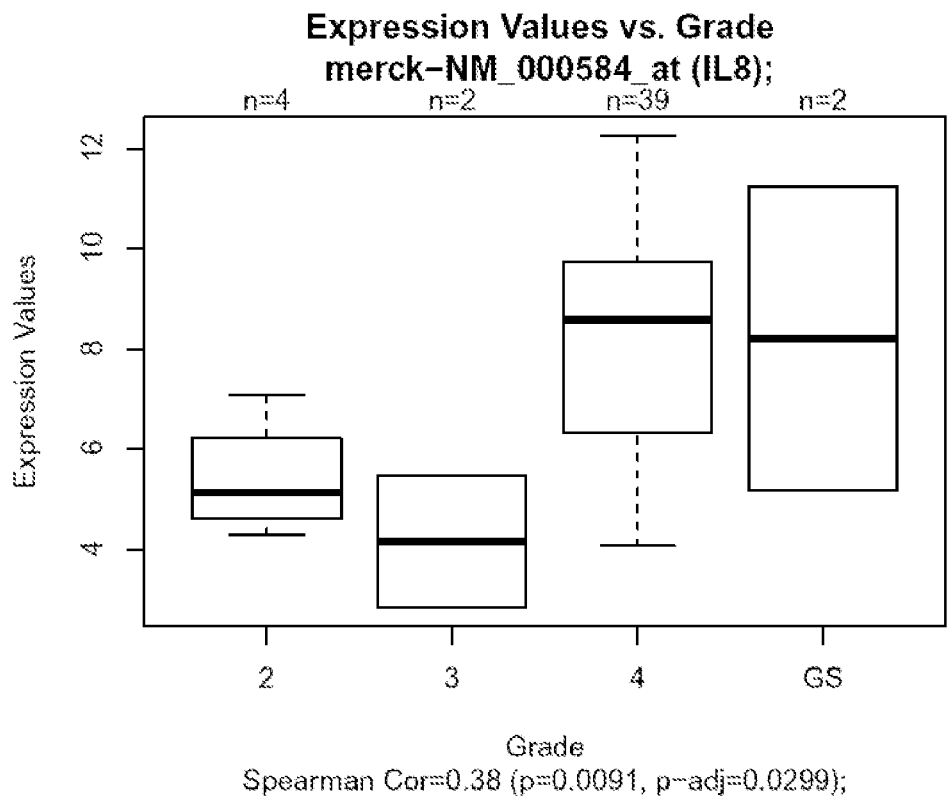
Figure 11D:
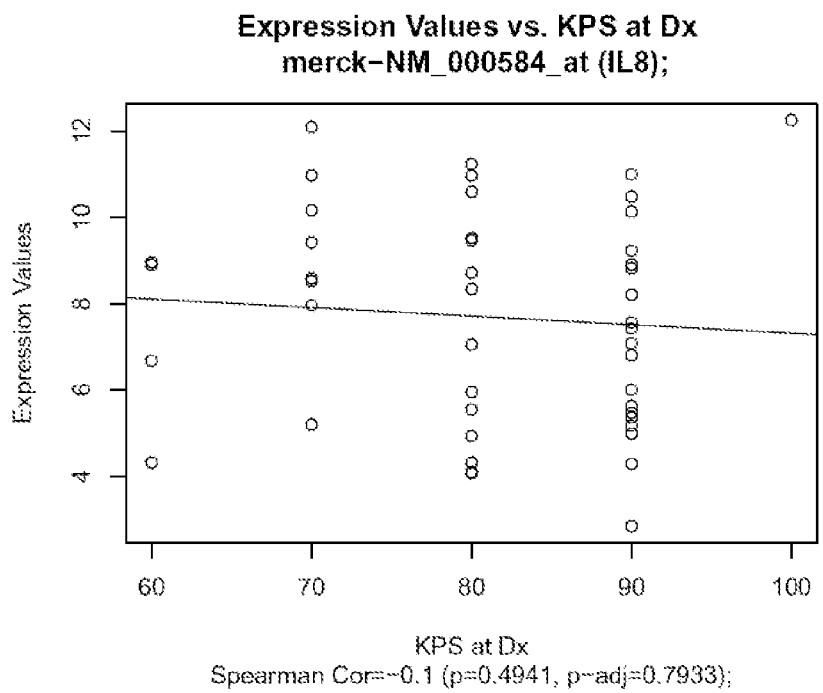
Figure 12A:
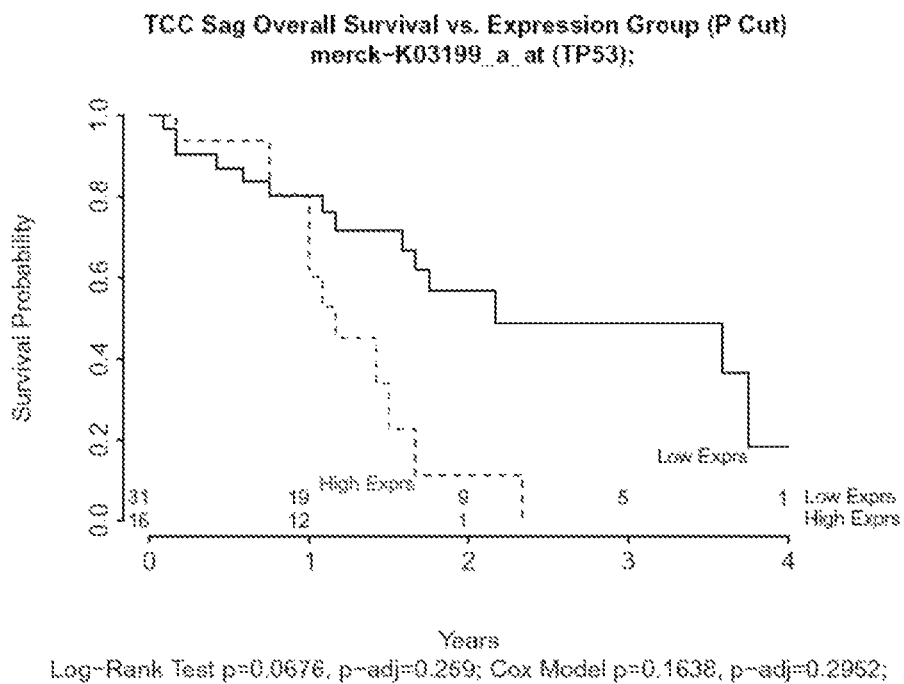
FIG. 12 is a series of images depicting the third probe set (Probe Set 3) (merck-K03199_a_at TP53) containing the TP53 gene. (A) a Kaplan-Meier survival curve depicting two risk groups (high and low-risk) and showing significant separation of the two survival curves. (B) graph depicting expression values versus age for TP53. (C) graph depicting expression values versus grade for TP53. (D) graph depicting expression values versus KPS at Dx.
Figure 12B:
Figure 12C:
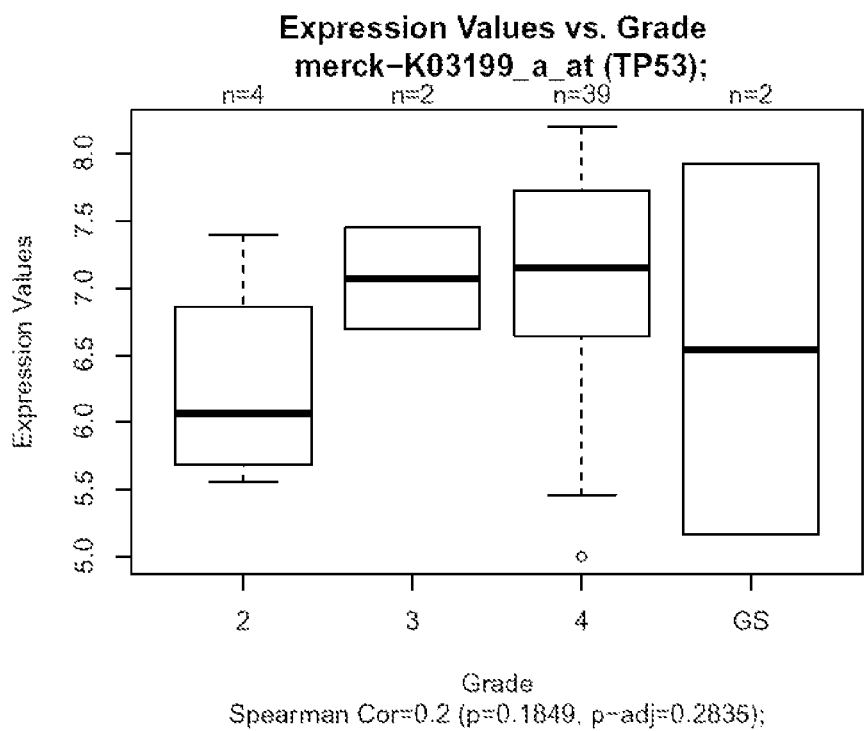
Figure 12D:
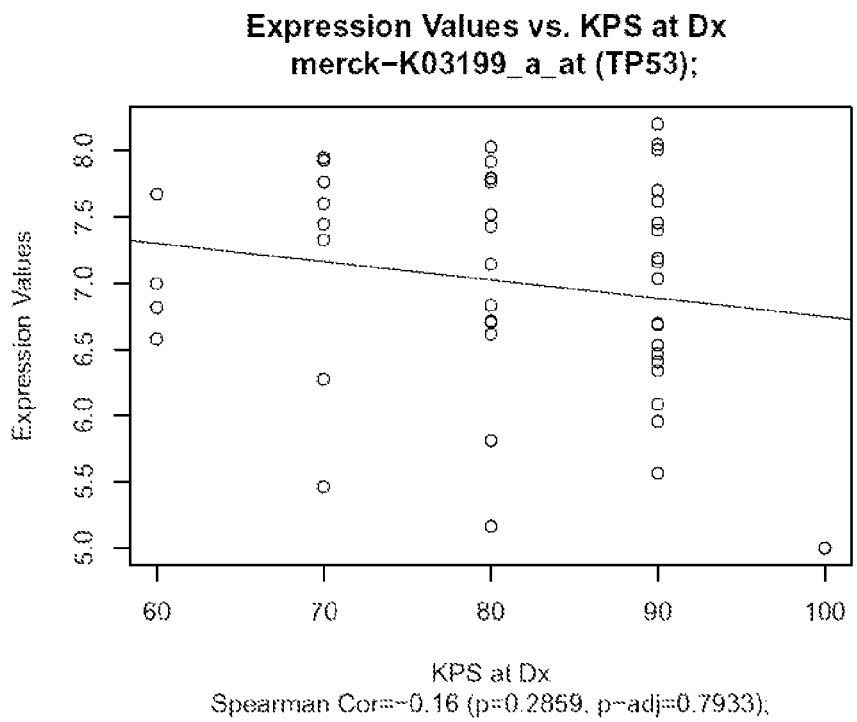
Figure 13A:
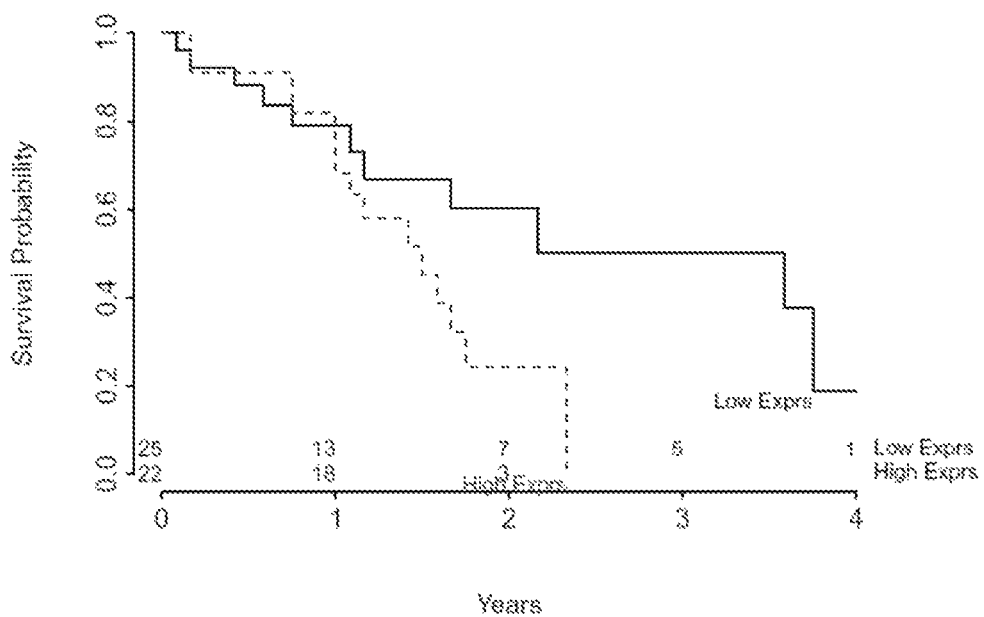
FIG. 13 is a series of images depicting the fourth probe set (Probe Set 4) (merck2-NM_000546 at TP53) containing the TP53 gene. (A) a Kaplan-Meier survival curve depicting two risk groups (high and low-risk) and showing significant separation of the two survival curves. (B) graph depicting expression values versus age for TP53. (C) graph depicting expression values versus grade for TP53. (D) graph depicting expression values versus KPS at Dx.
Figure 13B:
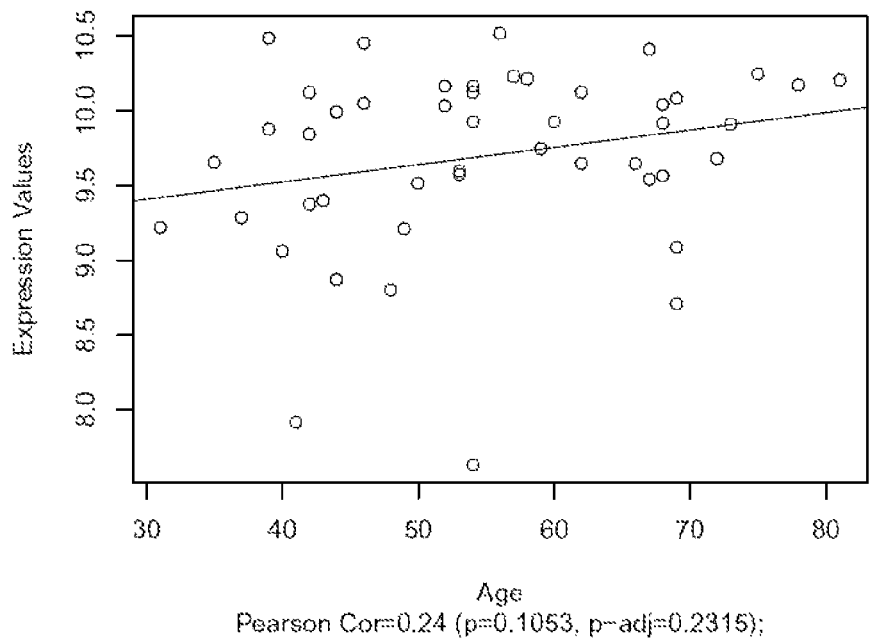
Figure 13C:
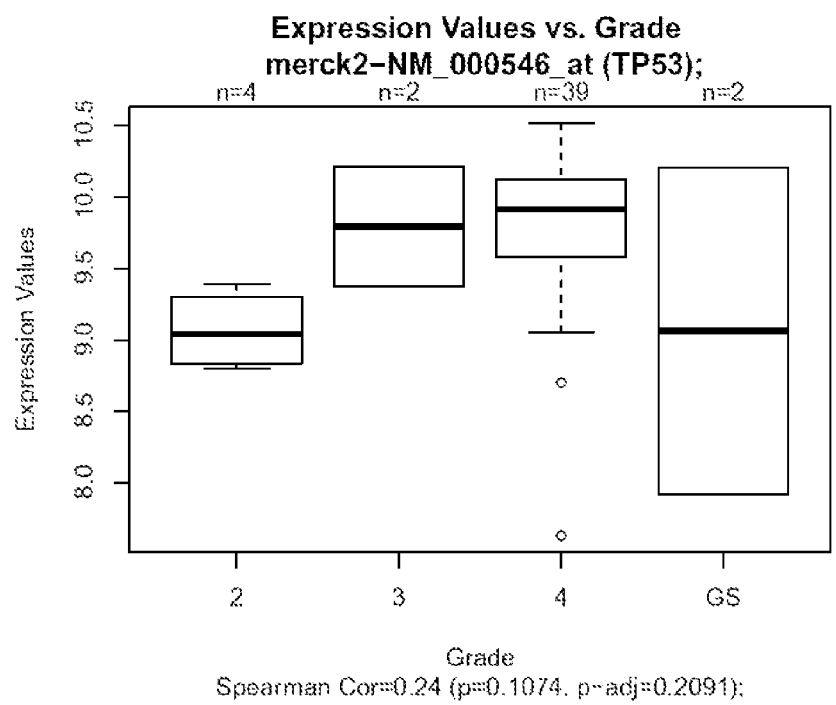
Figure 13D:
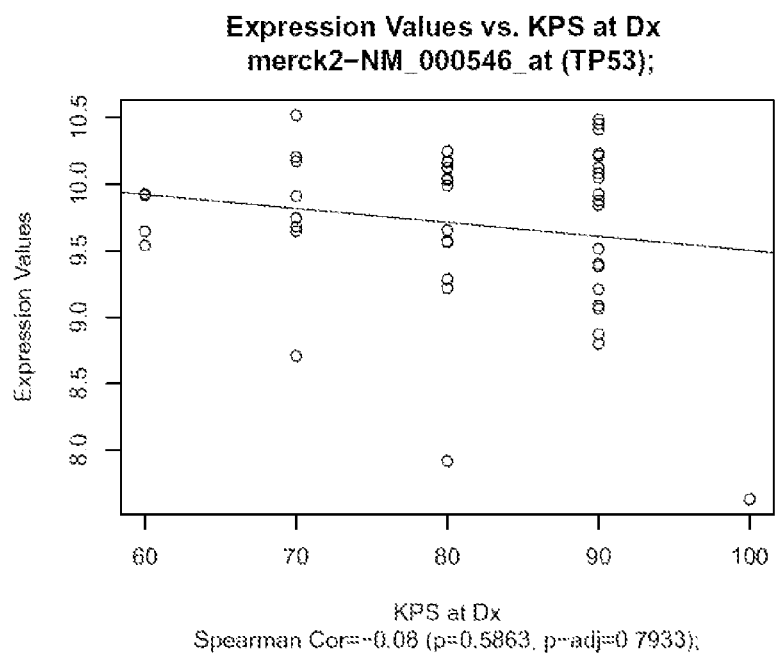
Figure 14A:
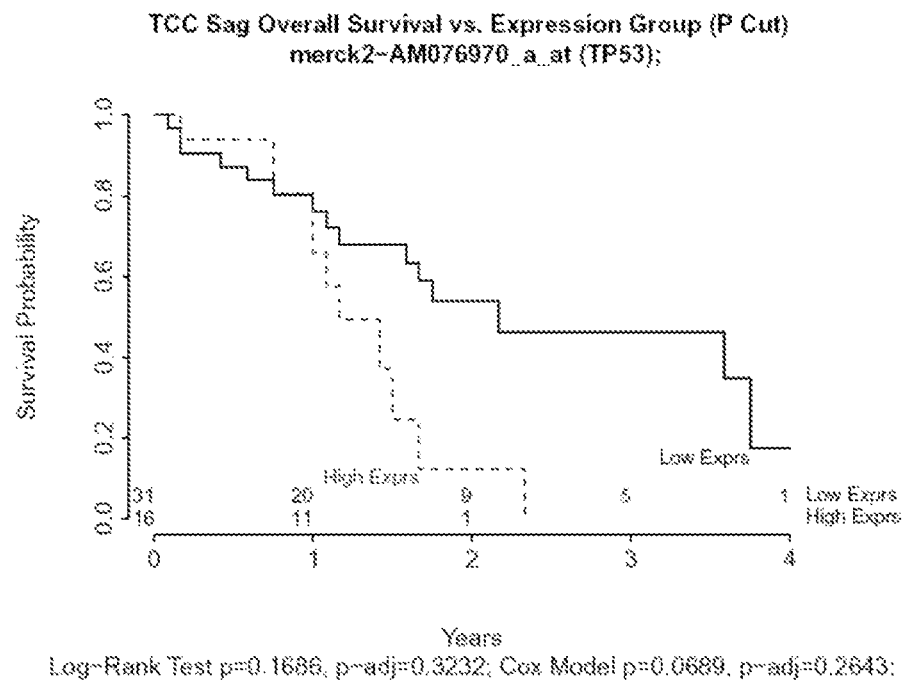
FIG. 14 is a series of images depicting the fifth probe set (Probe Set 5) (merck2-AM076970_a_at TP53) containing the TP53 gene. (A) a Kaplan-Meier survival curve depicting two risk groups (high and low-risk) and showing significant separation of the two survival curves. (B) graph depicting expression values versus age for TP53. (C) graph depicting expression values versus grade for TP53. (D) graph depicting expression values versus KPS at Dx.
Figure 14B:
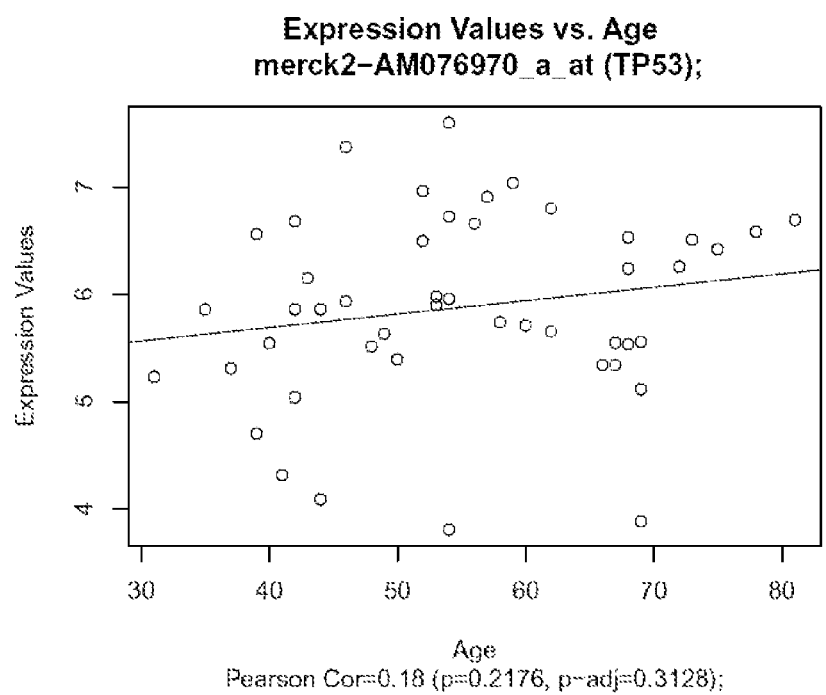
Figure 14C:
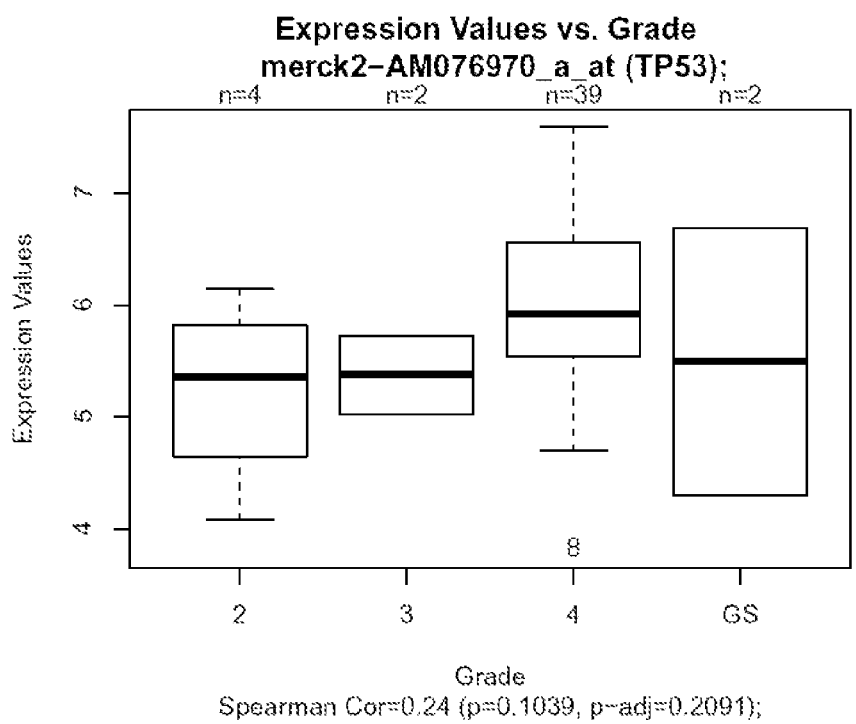
Figure 14D:
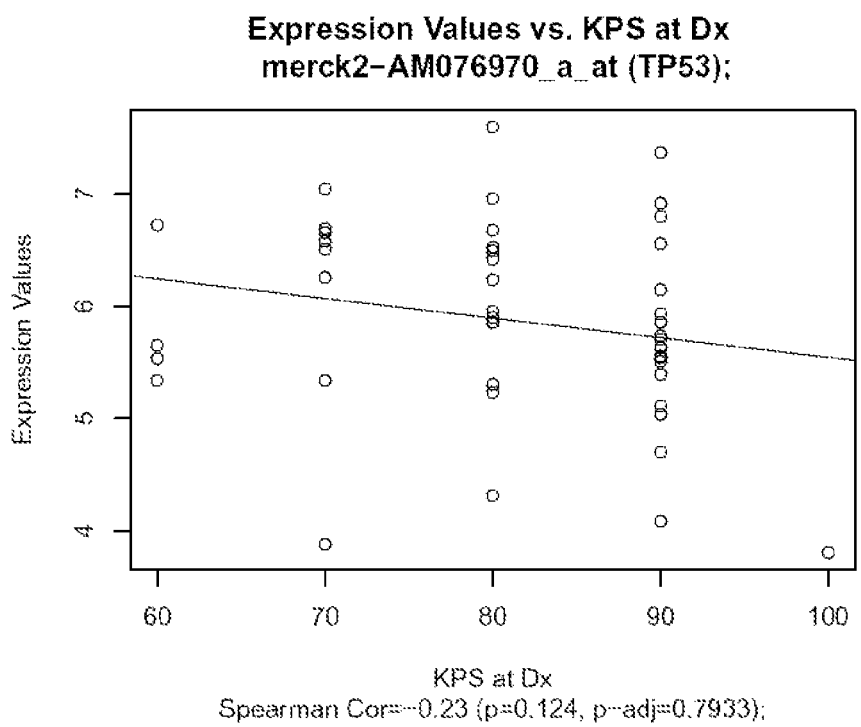
Figure 15A:
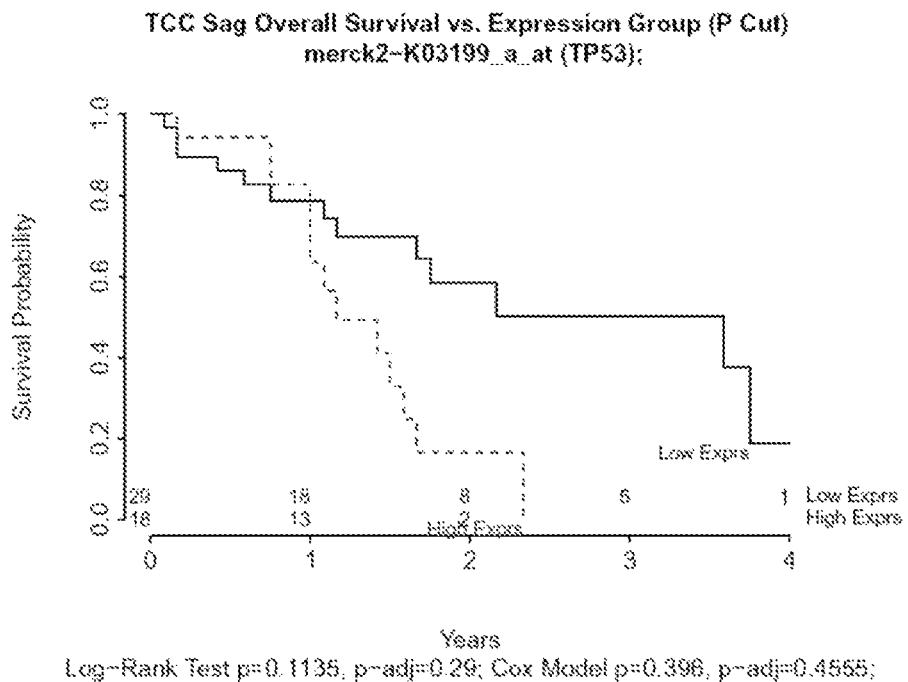
FIG. 15 is a series of images depicting the sixth probe set (Probe Set 6) (merck2-K03199_a_at TP53) containing the TP53 gene. (A) a Kaplan-Meier survival curve depicting two risk groups (high and low-risk) and showing significant separation of the two survival curves. (B) graph depicting expression values versus age for TP53. (C) graph depicting expression values versus grade for TP53. (D) graph depicting expression values versus KPS at Dx.
Figure 15B:
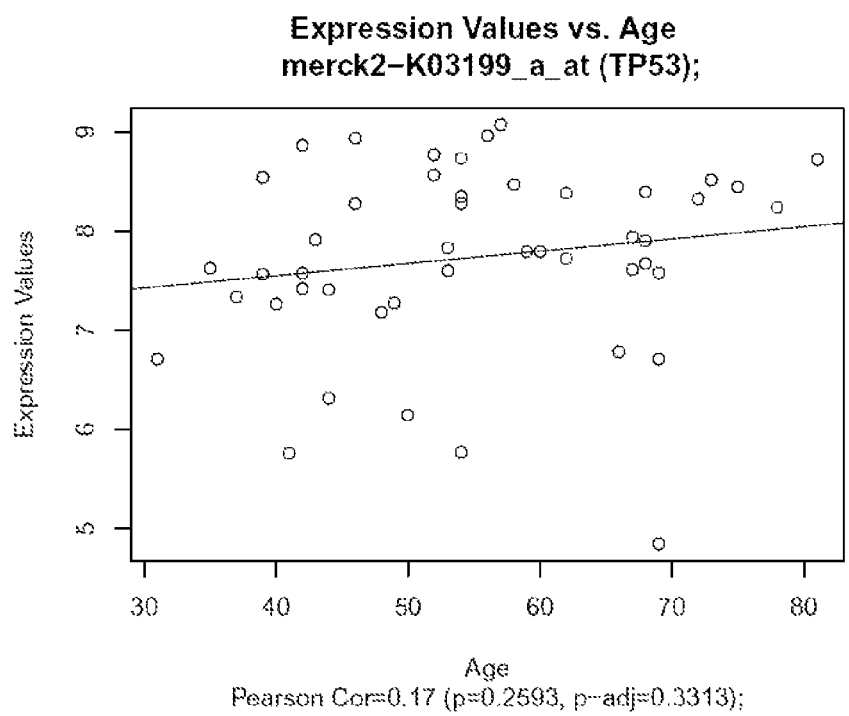
Figure 15C:
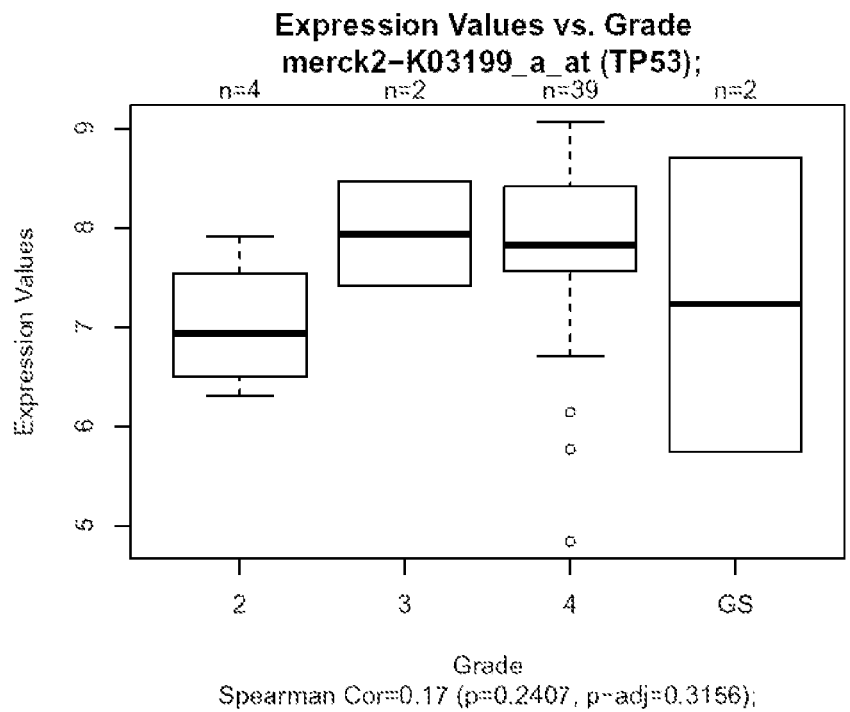
Figure 15D:
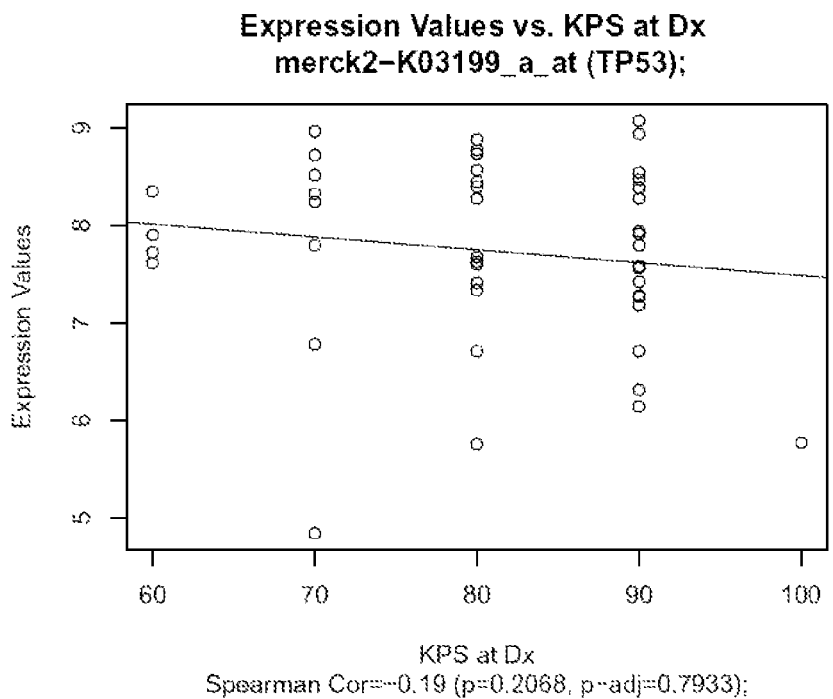
Figure 16A:
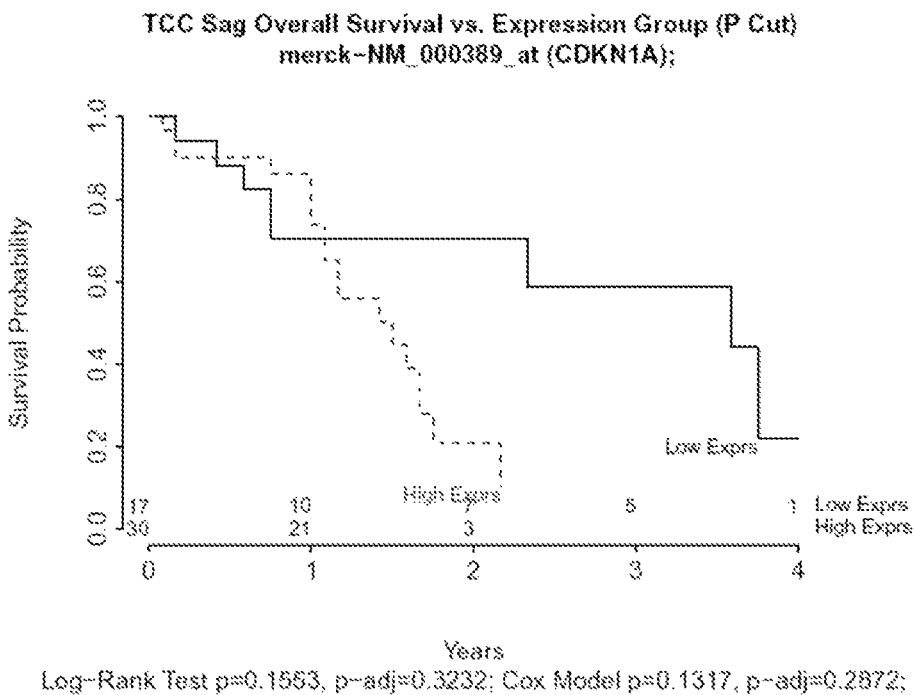
FIG. 16 is a series of images depicting the seventh probe set (Probe Set 7) (merck-NM_000389_at CDKN1A) containing the CDKN1A gene. (A) a Kaplan-Meier survival curve depicting two risk groups (high and low-risk) and showing significant separation of the two survival curves. (B) graph depicting expression values versus age for CDKN1A. (C) graph depicting expression values versus grade for CDKN1A. (D) graph depicting expression values versus KPS at Dx.
Figure 16B:
Figure 16C:
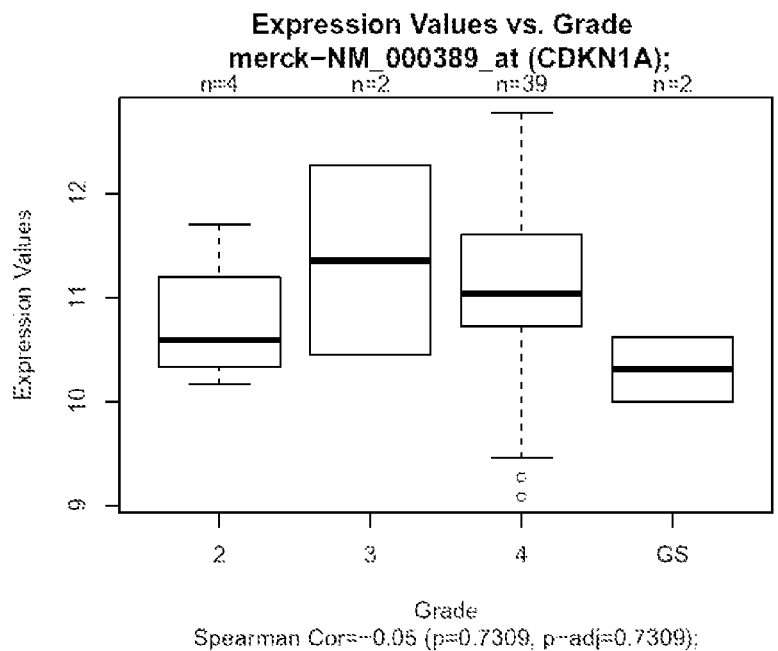
Figure 16D:
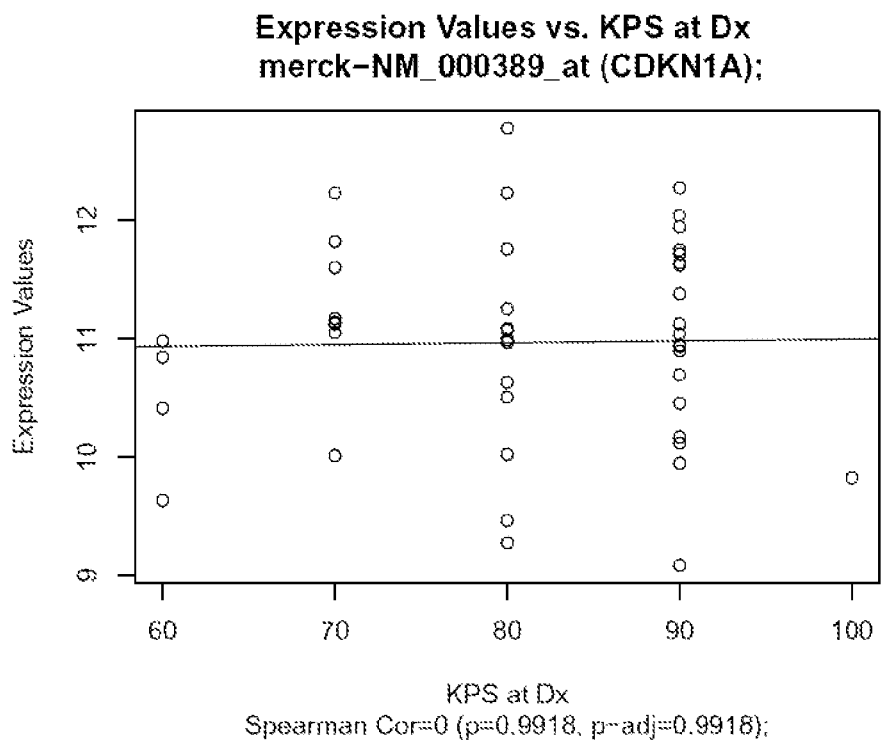
Figure 17A:
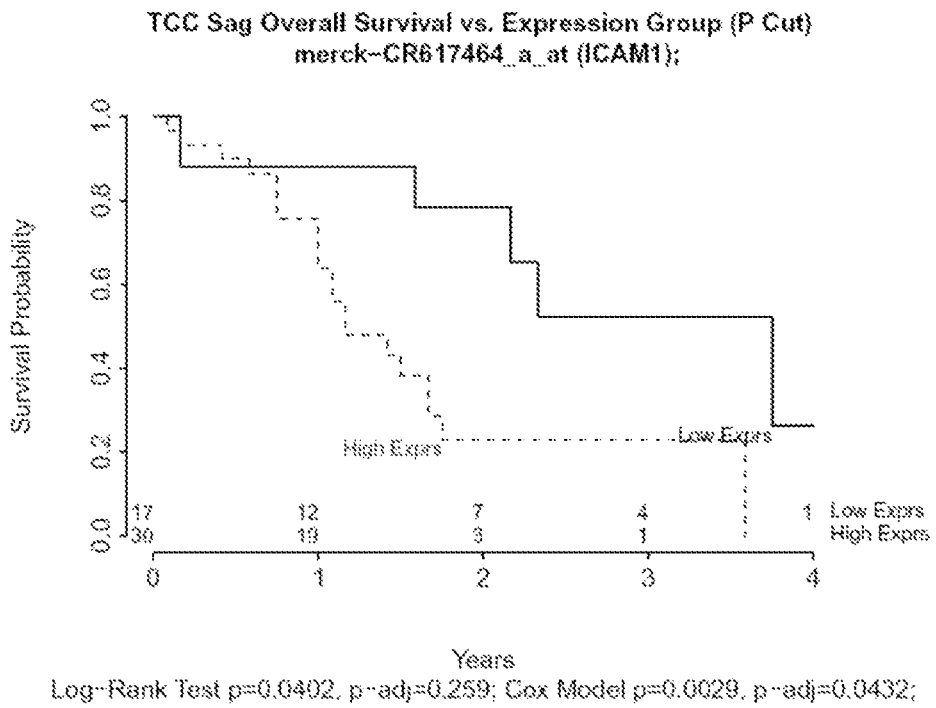
FIG. 17 is a series of images depicting the eighth probe set (Probe Set 8) (merck-CR617464_a_at ICAM1) containing the ICAM1 gene. (A) a Kaplan-Meier survival curve depicting two risk groups (high and low-risk) and showing significant separation of the two survival curves. (B) graph depicting expression values versus age for ICAM1. (C) graph depicting expression values versus grade for ICAM1. (D) graph depicting expression values versus KPS at Dx.
Figure 17B:
Figure 17C:
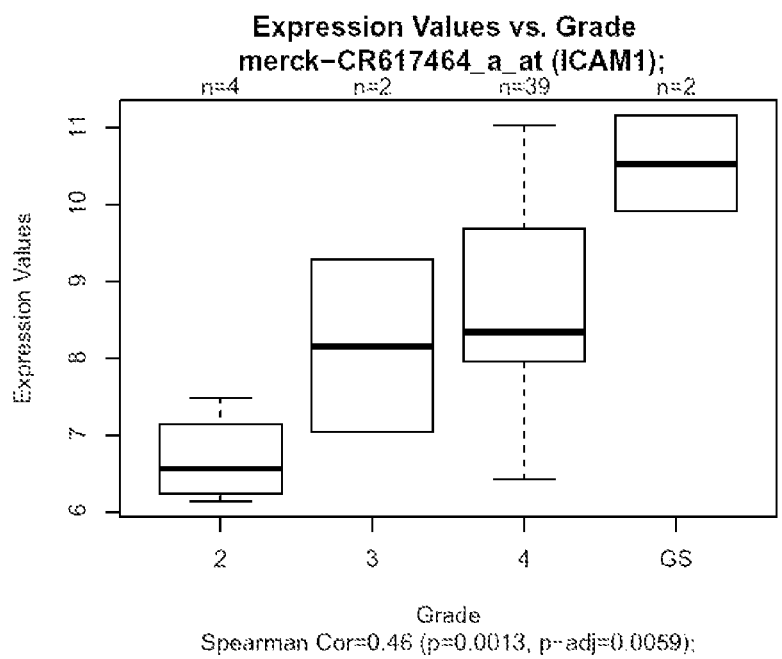
Figure 17D:
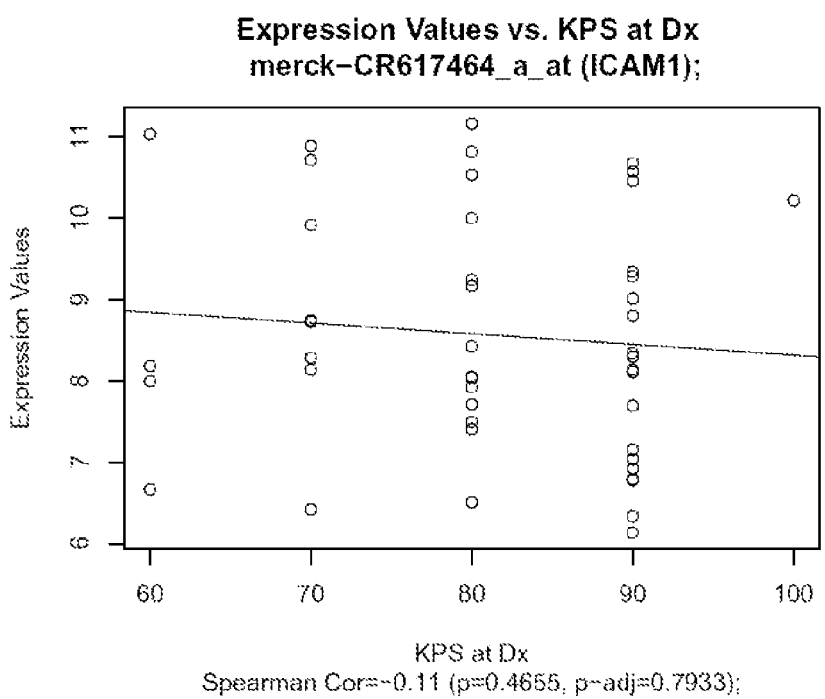
Figure 18A:
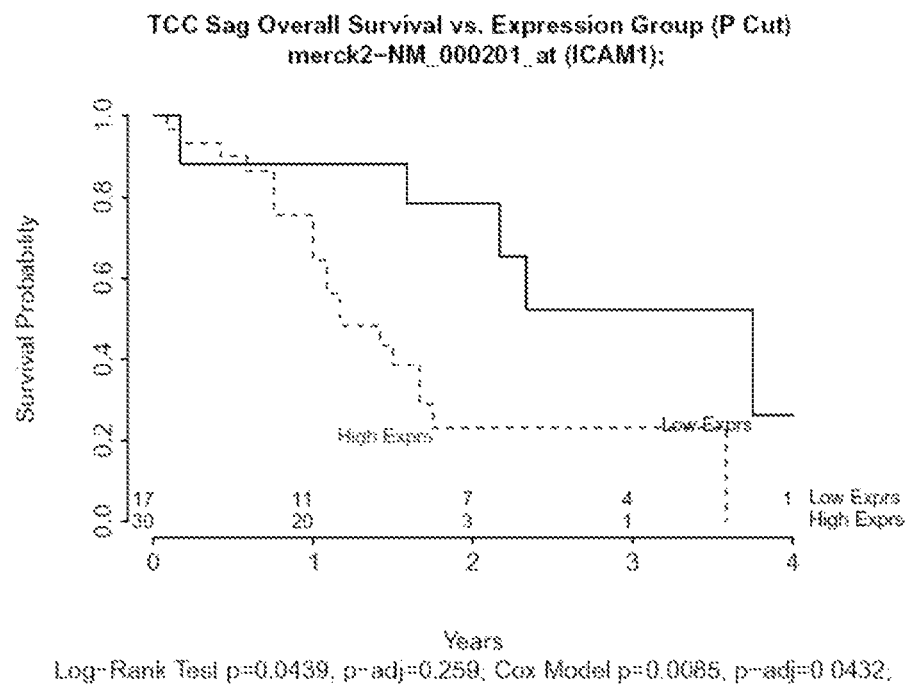
FIG. 18 is a series of images depicting the ninth probe set (Probe Set 9) (merck2-NM_000201 at ICAM1) containing the ICAM1 gene. (A) a Kaplan-Meier survival curve depicting two risk groups (high and low-risk) and showing significant separation of the two survival curves. (B) graph depicting expression values versus age for ICAM1. (C) graph depicting expression values versus grade for ICAM1. (D) graph depicting expression values versus KPS at Dx.
Figure 18B:
Figure 18C:
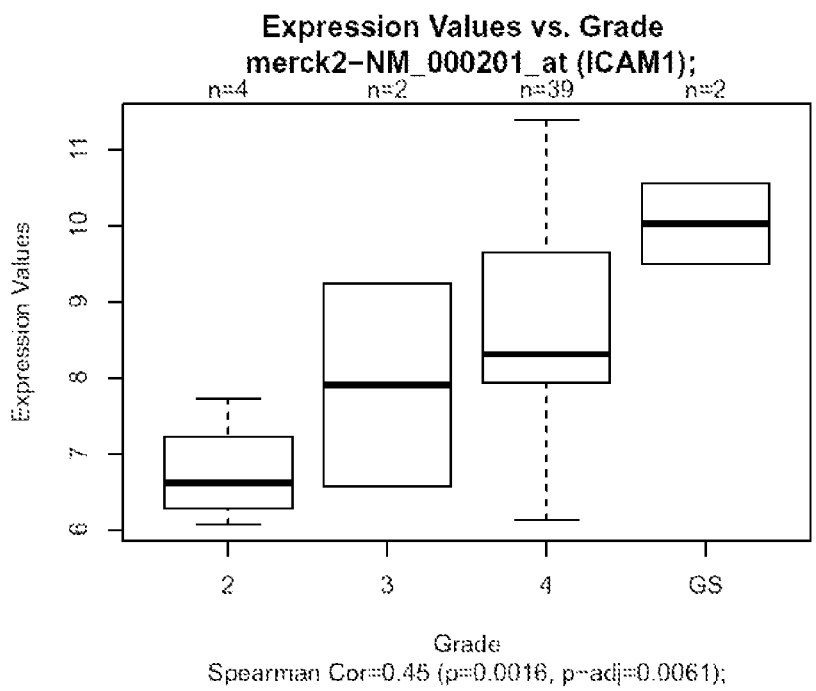
Figure 18D:
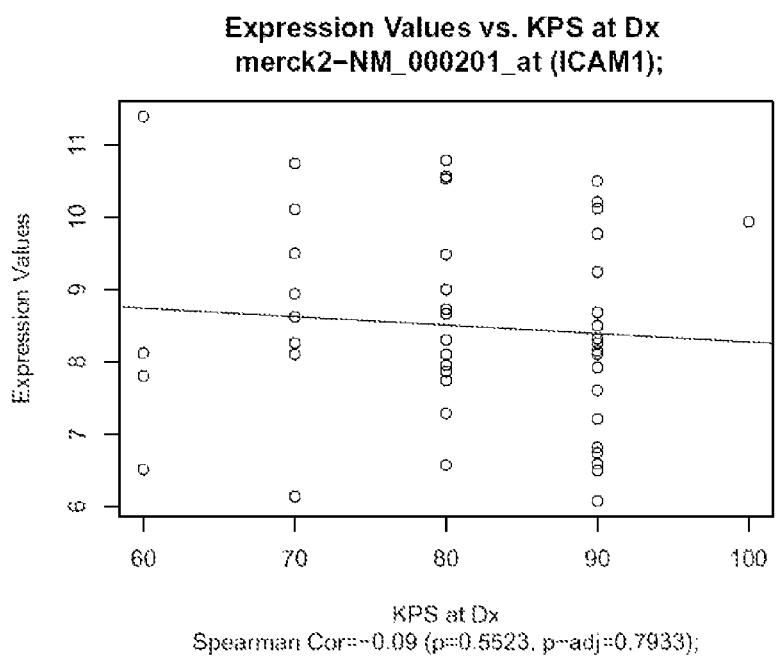
Figure 19A:
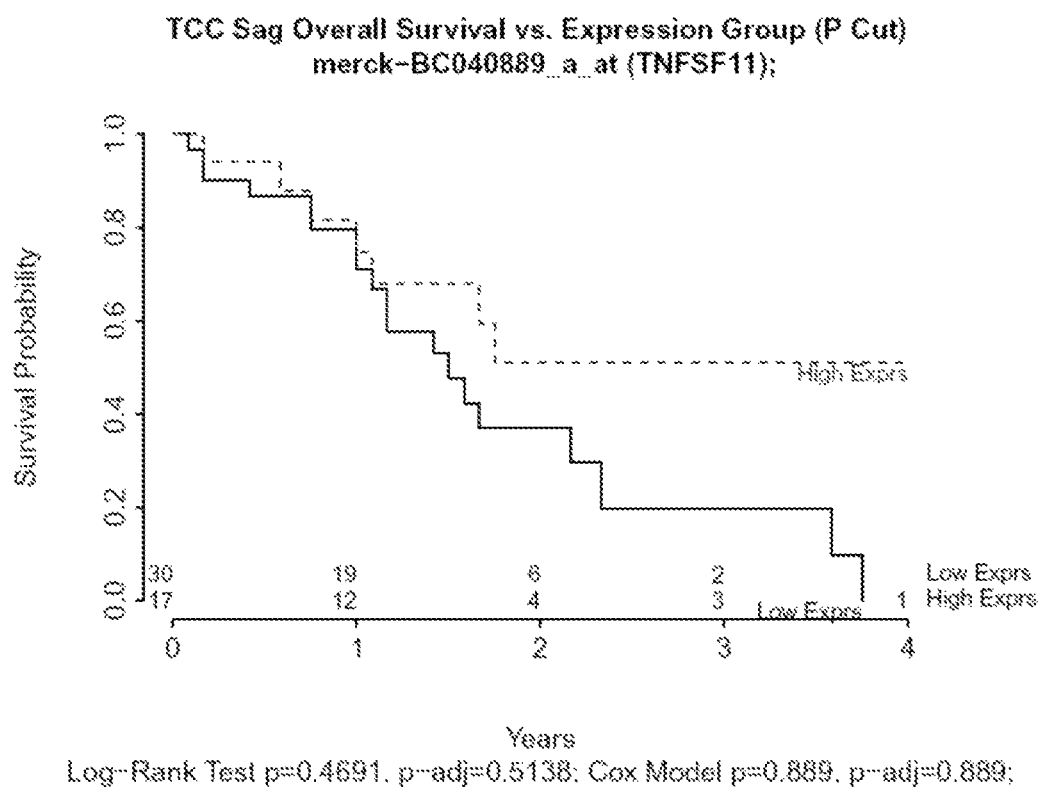
FIG. 19 is a series of images depicting the tenth probe set (Probe Set 10) (merck-BC040889_a_at TNFSF11) containing the TNFSF11 gene. (A) a Kaplan-Meier survival curve depicting two risk groups (high and low-risk) and showing significant separation of the two survival curves. (B) graph depicting expression values versus age for TNFSF11. (C) graph depicting expression values versus grade for TNFSF11. (D) graph depicting expression values versus KPS at Dx.
Figure 19B:
Figure 19C:
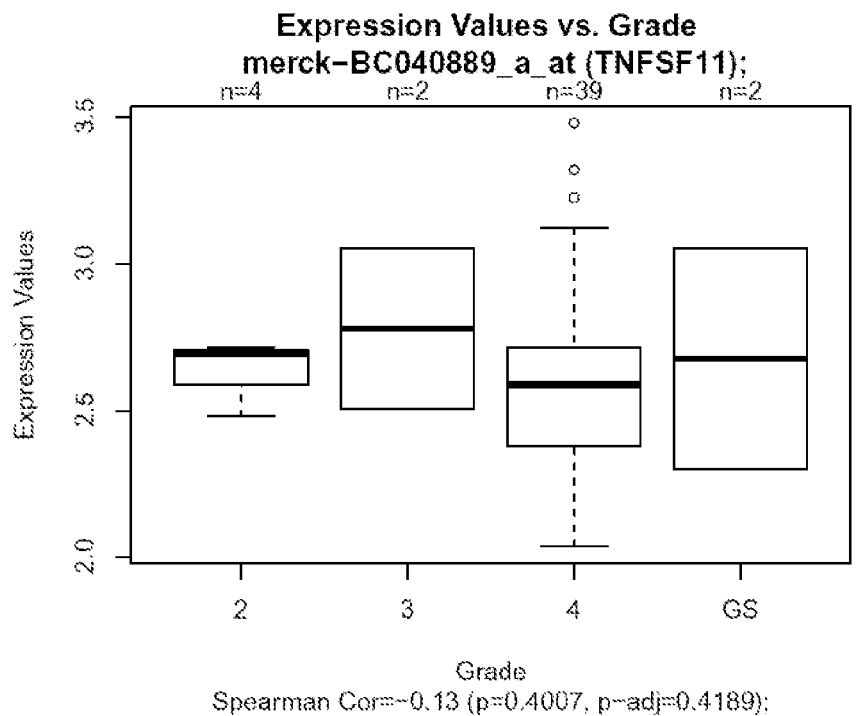
Figure 19D:
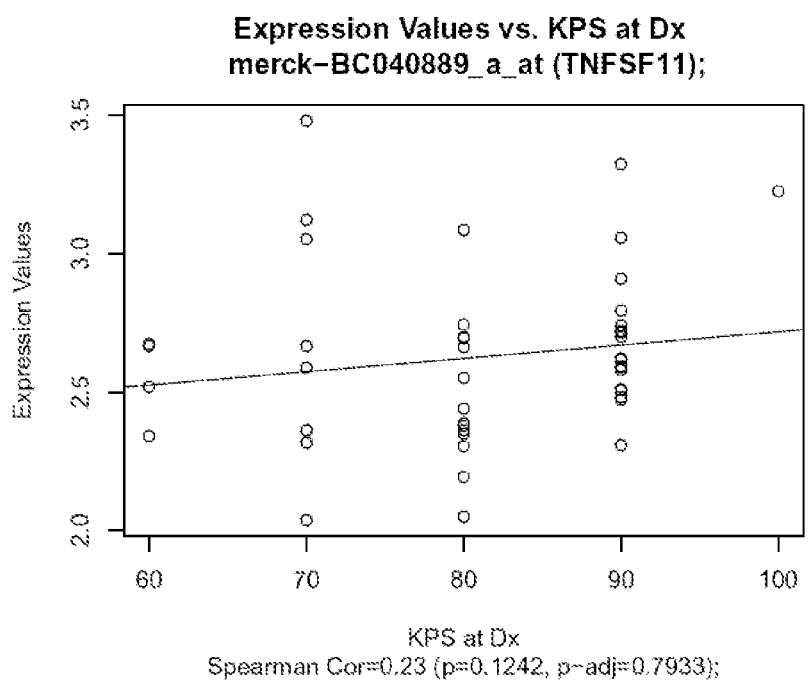
Figure 20A:
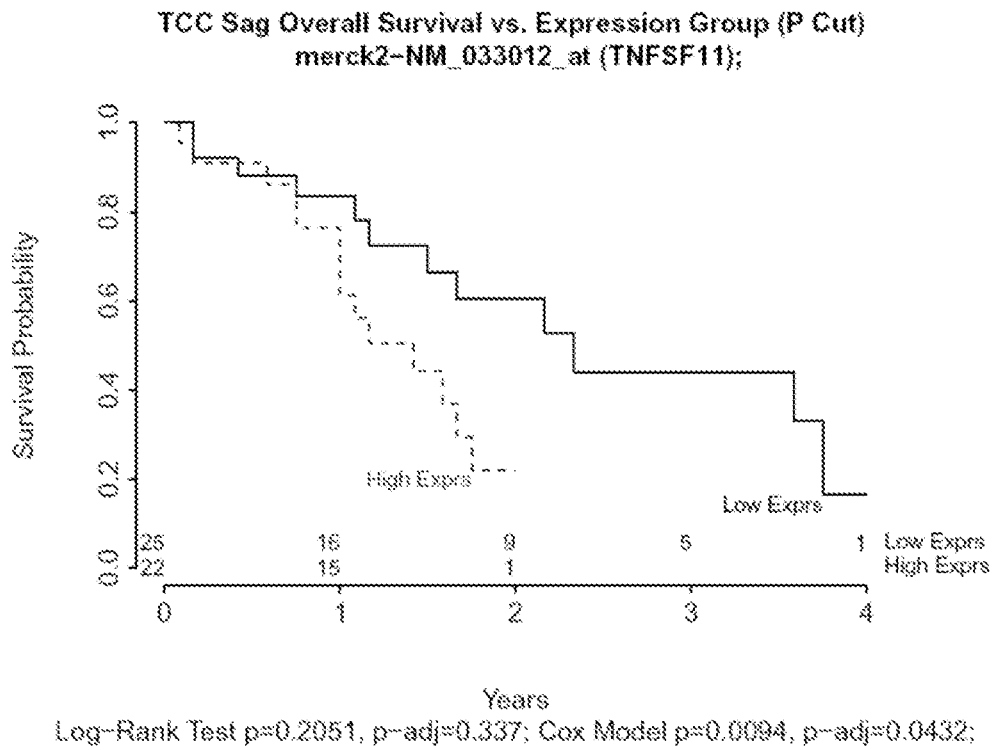
FIG. 20 is a series of images depicting the eleventh probe set (Probe Set 11) (merck2-NM_033012_at TNFSF11) containing the TNFSF11 gene. (A) a Kaplan-Meier survival curve depicting two risk groups (high and low-risk) and showing significant separation of the two survival curves. (B) graph depicting expression values versus age for TNFSF11. (C) graph depicting expression values versus grade for TNFSF11. (D) graph depicting expression values versus KPS at Dx.
Figure 20B:
Figure 20C:
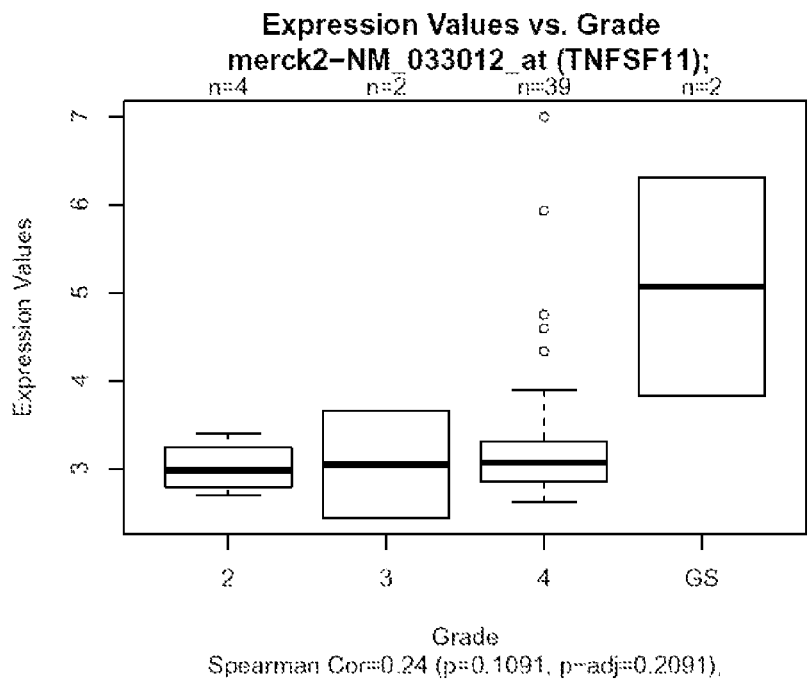
Figure 20D:
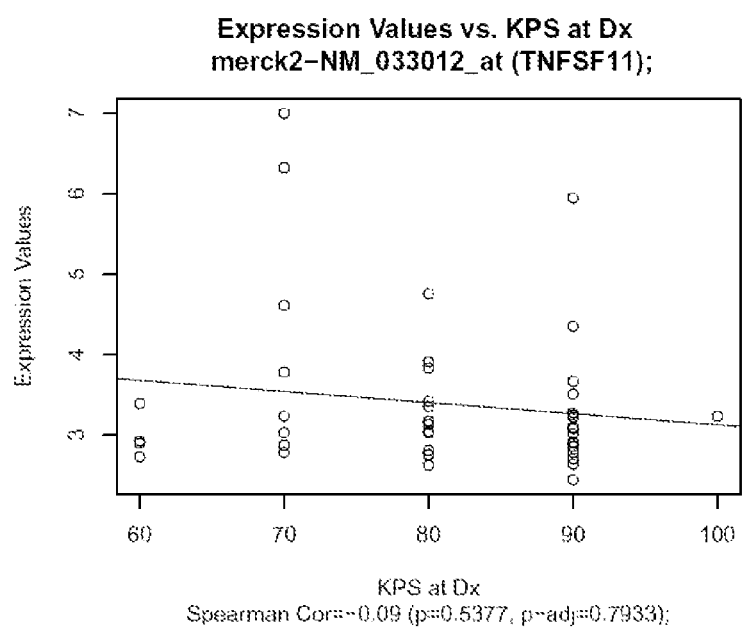
Figure 21A:
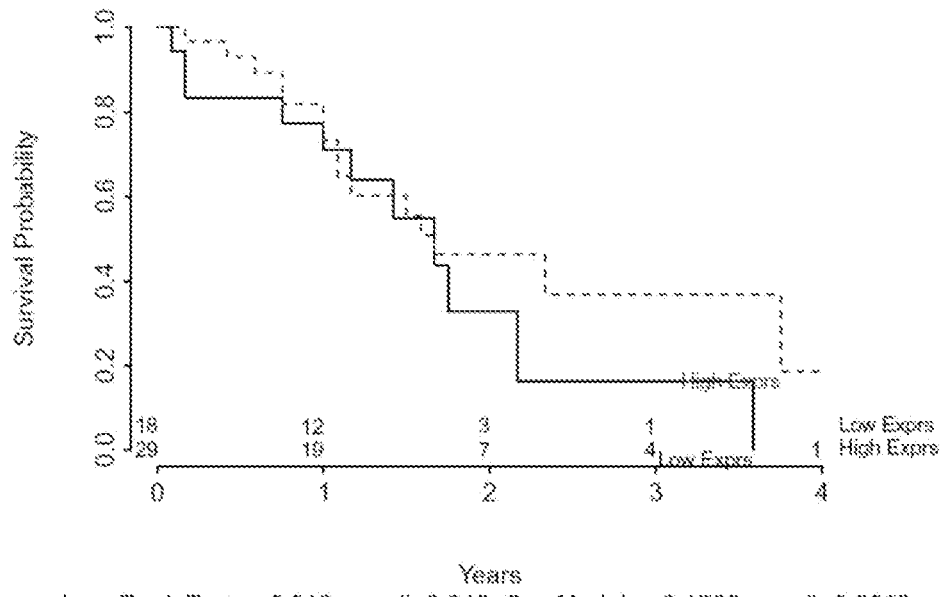
FIG. 21 is a series of images depicting the twelfth probe set (Probe Set 12) (merck2-AB064268_a_at TNFSF11) containing the TNFSF11 gene. (A) a Kaplan-Meier survival curve depicting two risk groups (high and low-risk) and showing significant separation of the two survival curves. (B) graph depicting expression values versus age for TNFSF11. (C) graph depicting expression values versus grade for TNFSF11. (D) graph depicting expression values versus KPS at Dx.
Figure 21B:
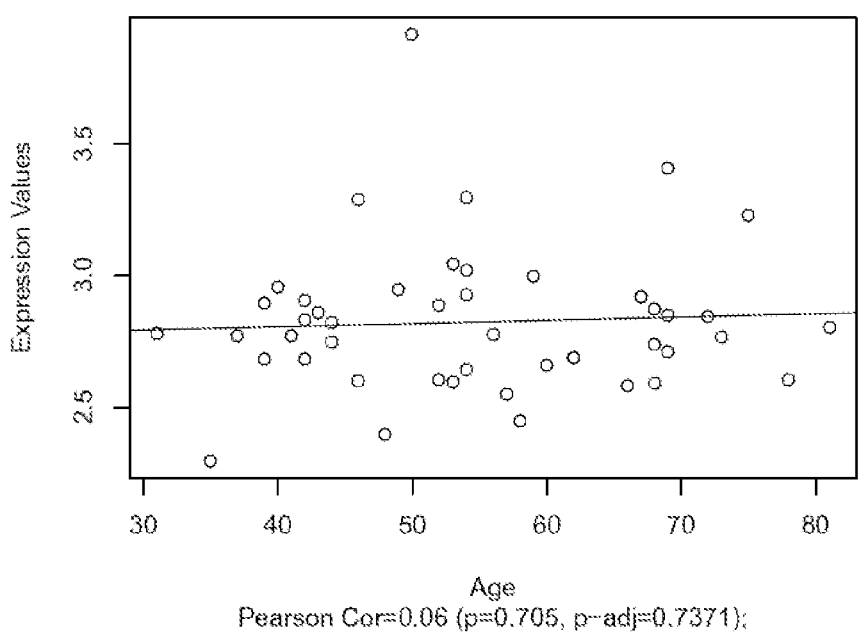
Figure 21C:
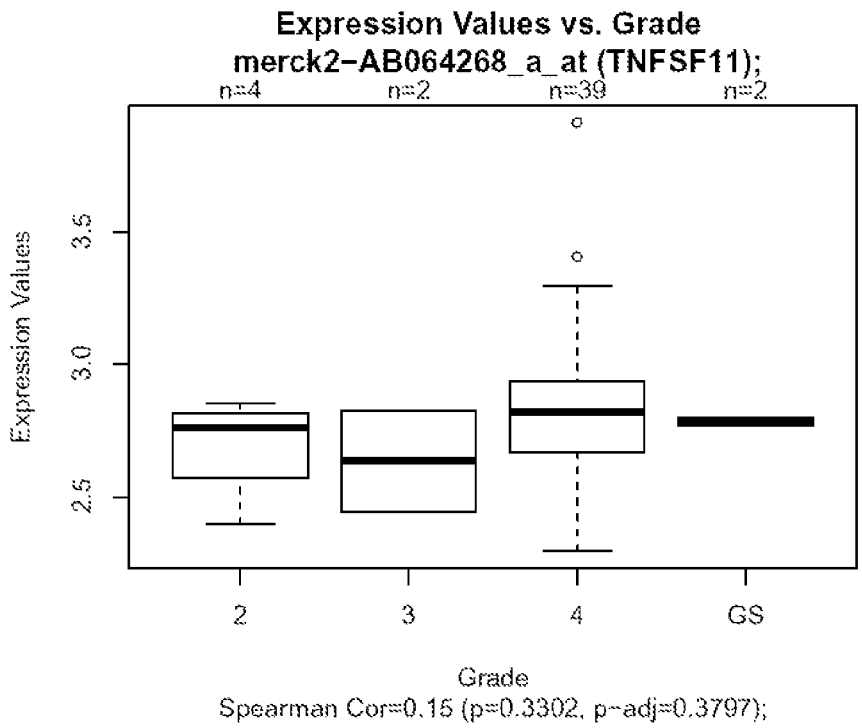
Figure 21D:
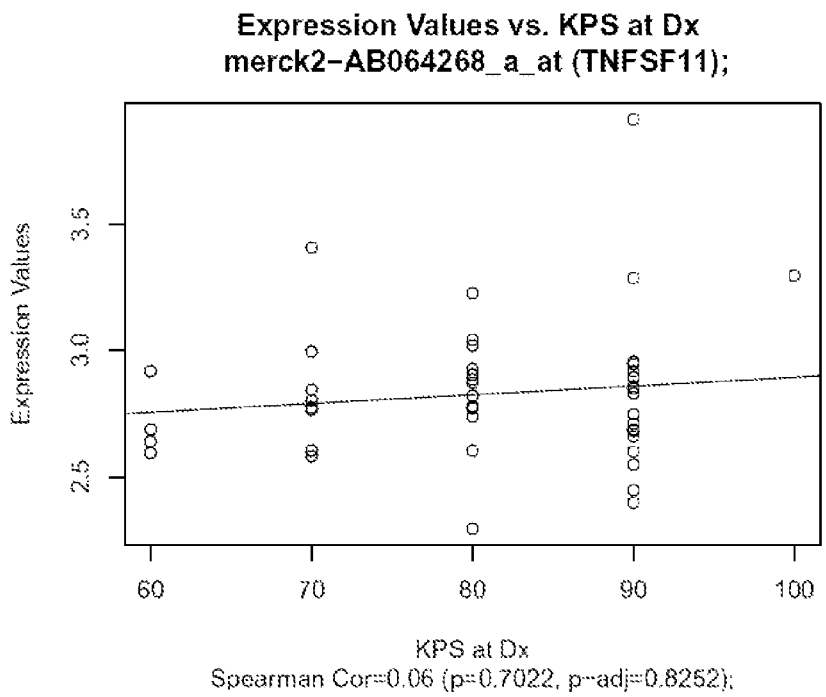
Figure 22A:
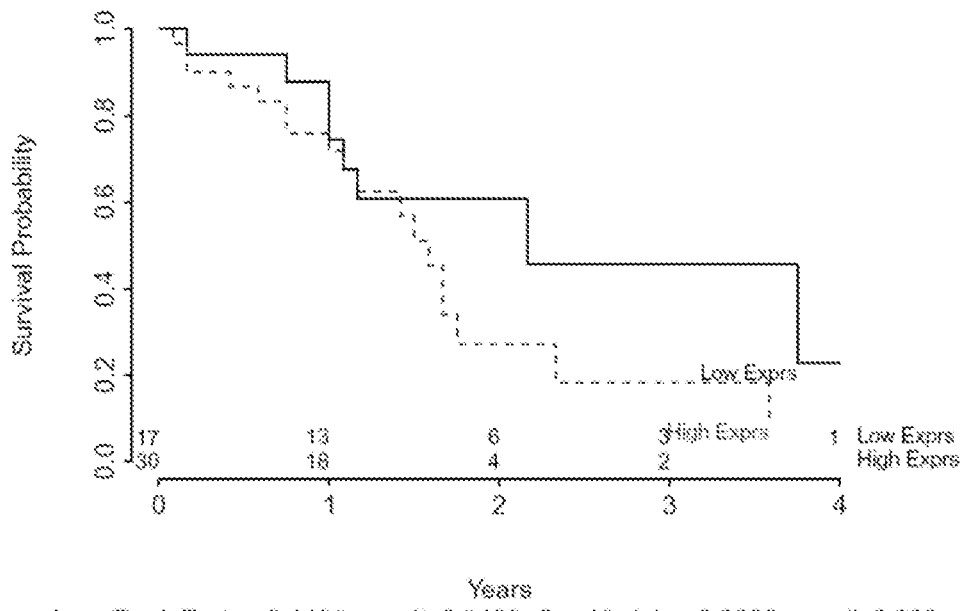
FIG. 22 is a series of images depicting the thirteenth probe set (Probe Set 13) (merck-BC030155_a_at TNFRSF11B) containing the TNFRSF11B gene. (A) a Kaplan-Meier survival curve depicting two risk groups (high and low-risk) and showing significant separation of the two survival curves. (B) graph depicting expression values versus age for TNFRSF11B. (C) graph depicting expression values versus grade for TNFRSF11B. (D) graph depicting expression values versus KPS at Dx.
Figure 22B:
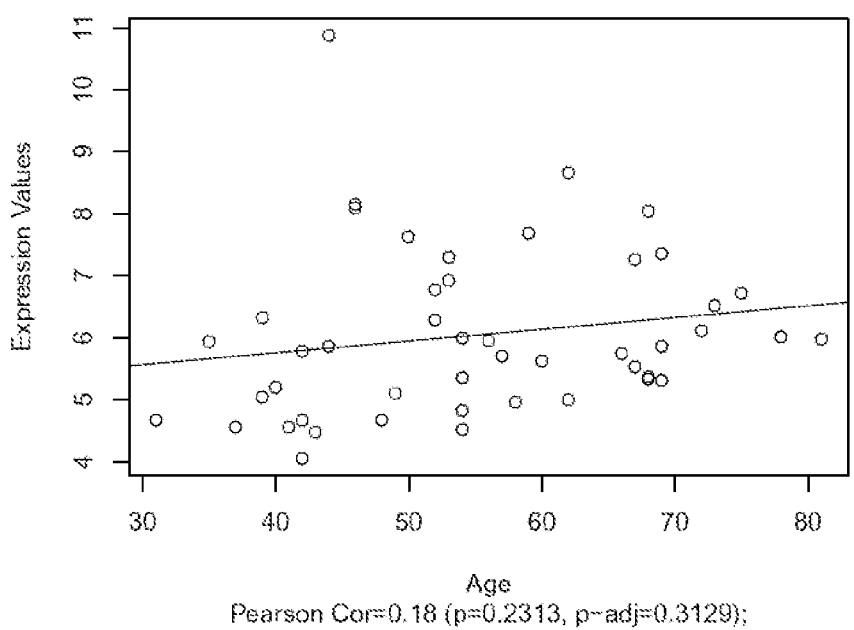
Figure 22C:
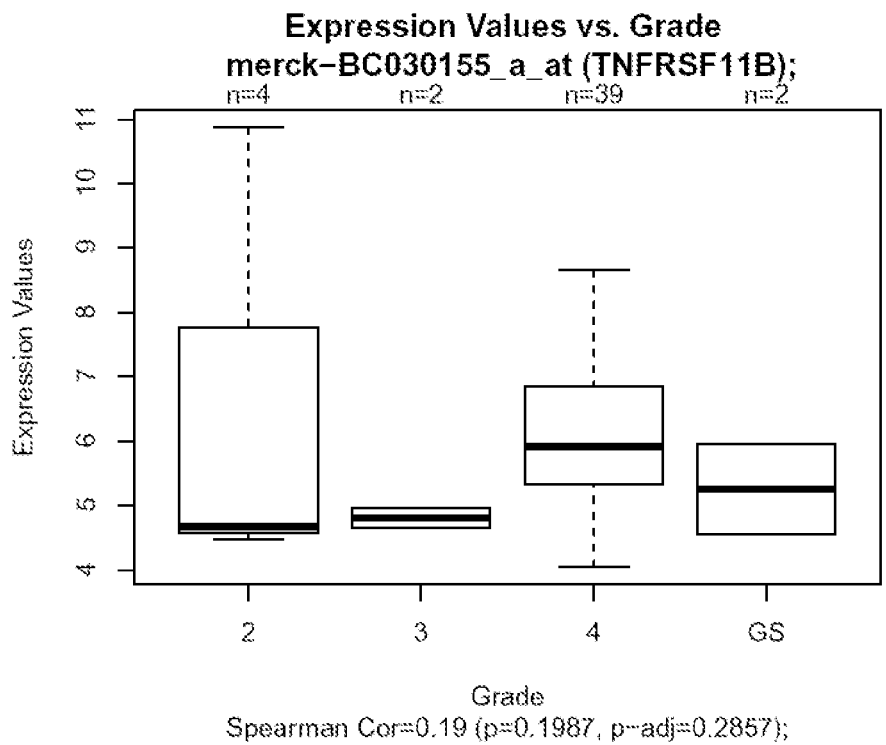
Figure 22D:
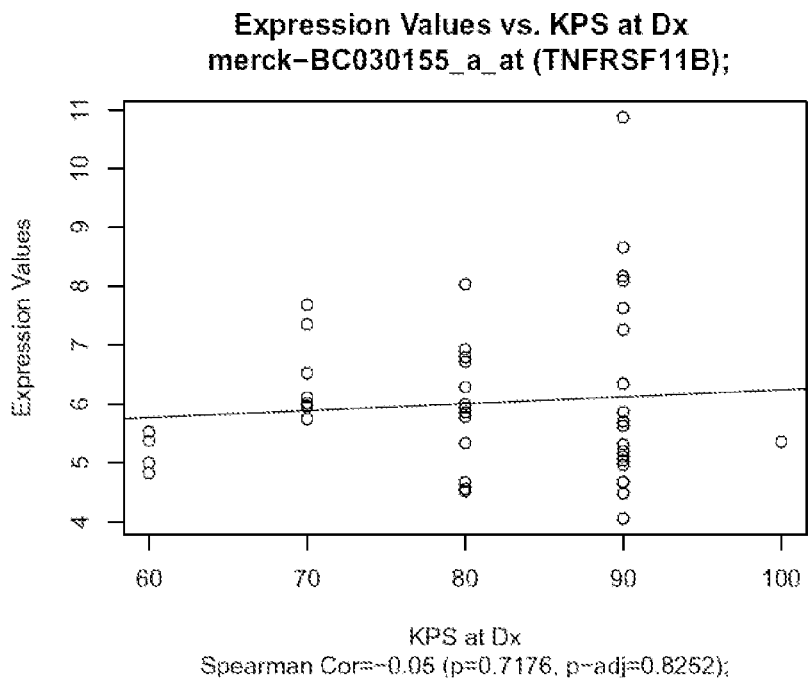
Figure 23A:
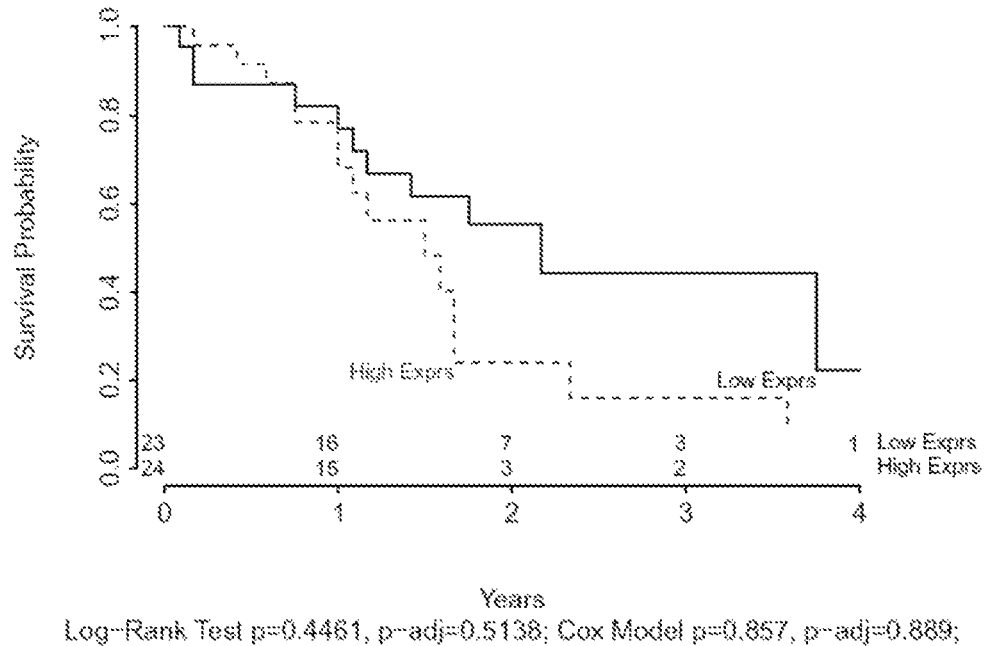
FIG. 23 is a series of images depicting the fourteenth probe set (Probe Set 14) (merck2-NM_002546_at TNFRSF11B) containing the TNFRSF11B gene. (A) a Kaplan-Meier survival curve depicting two risk groups (high and low-risk) and showing significant separation of the two survival curves. (B) graph depicting expression values versus age for TNFRSF11B. (C) graph depicting expression values versus grade for TNFRSF11B. (D) graph depicting expression values versus KPS at Dx.
Figure 23B:
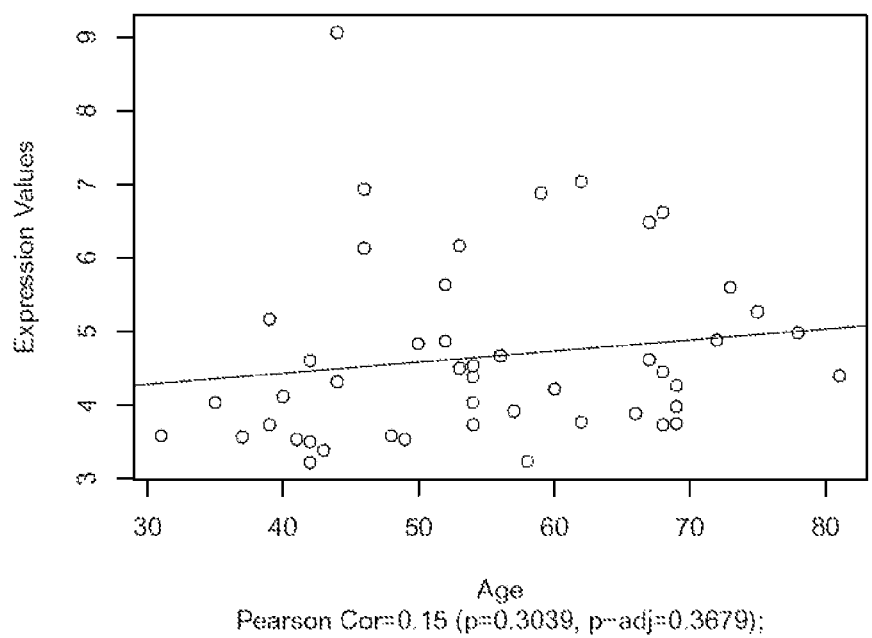
Figure 23C:
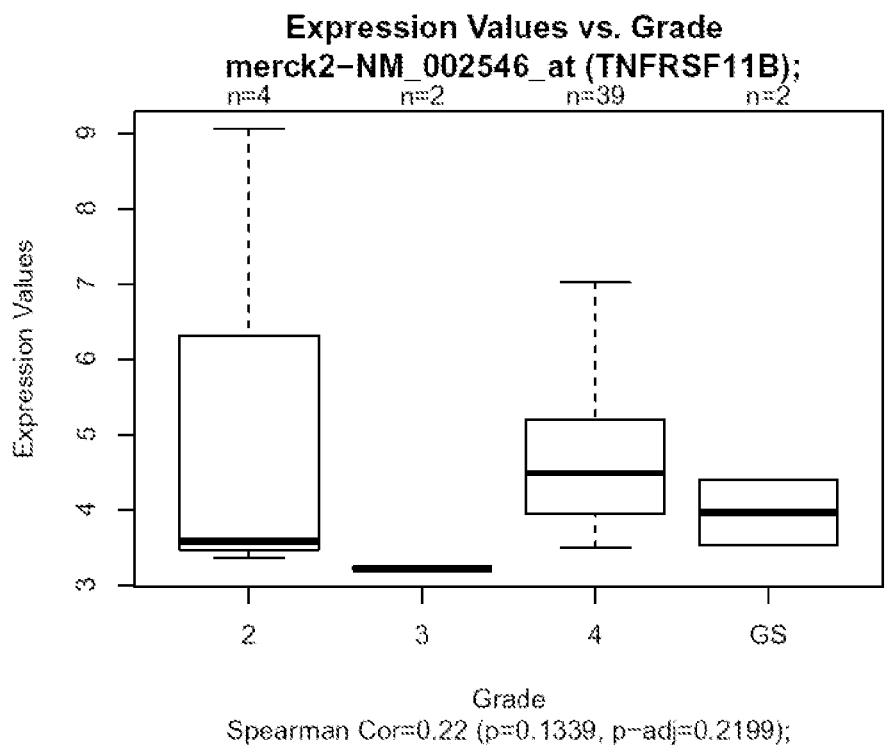
Figure 23D:
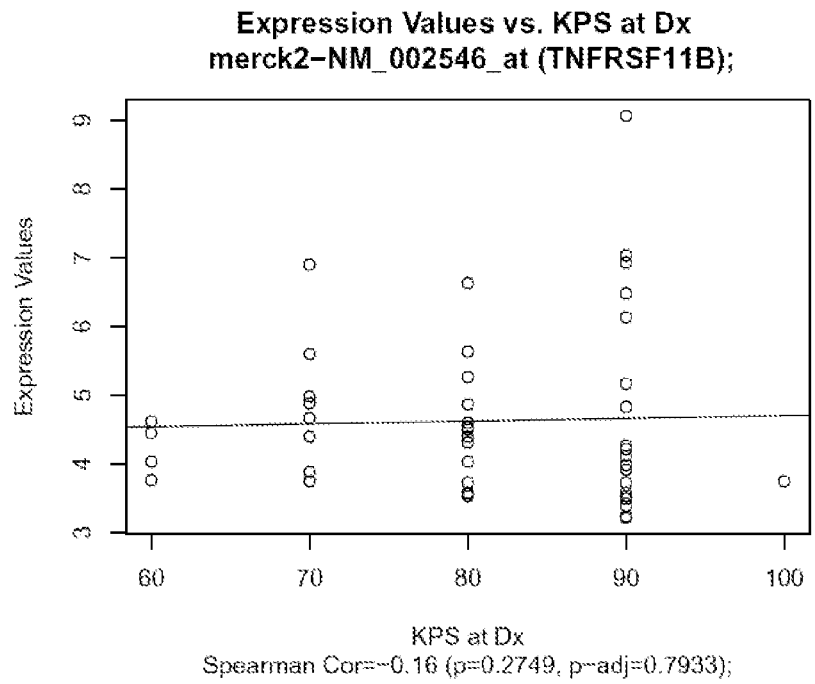
Figure 24A:
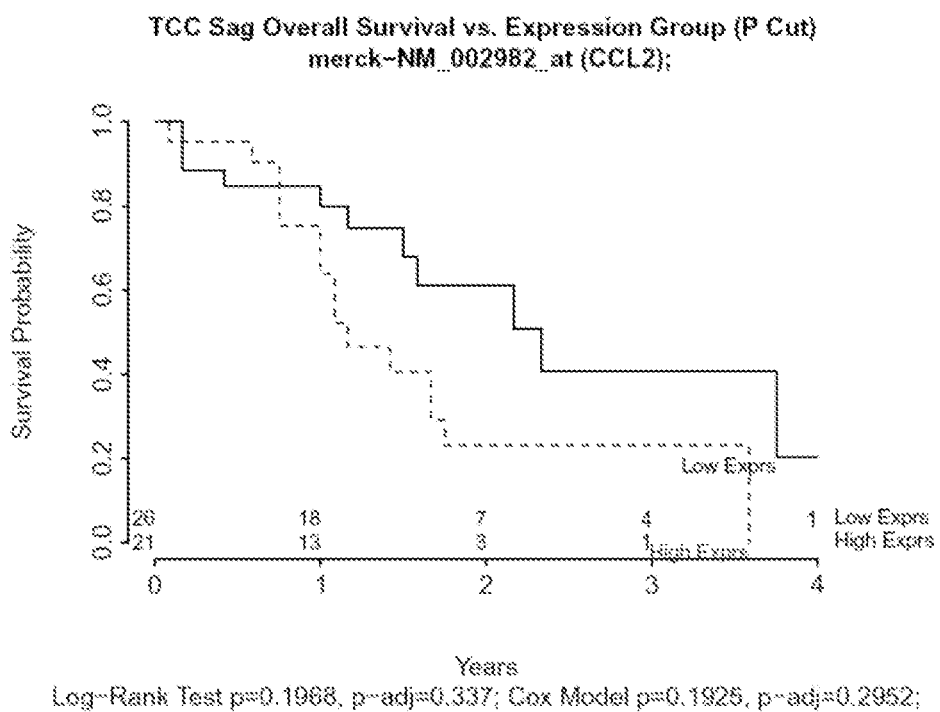
FIG. 24 is a series of images depicting the fifteenth probe set (Probe Set 15) (merck-NM_002982 at CCL2) containing the CCL2 gene. (A) a Kaplan-Meier survival curve depicting two risk groups (high and low-risk) and showing significant separation of the two survival curves. (B) graph depicting expression values versus age for CCL2. (C) graph depicting expression values versus grade for CCL2. (D) graph depicting expression values versus KPS at Dx.
Figure 24B:
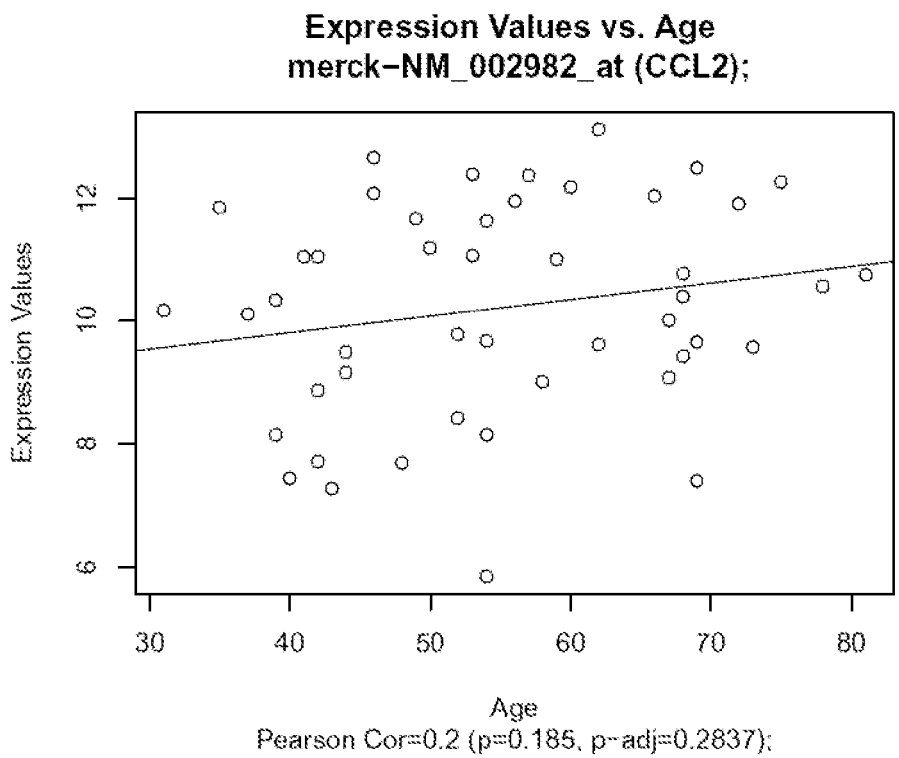
Figure 24C:
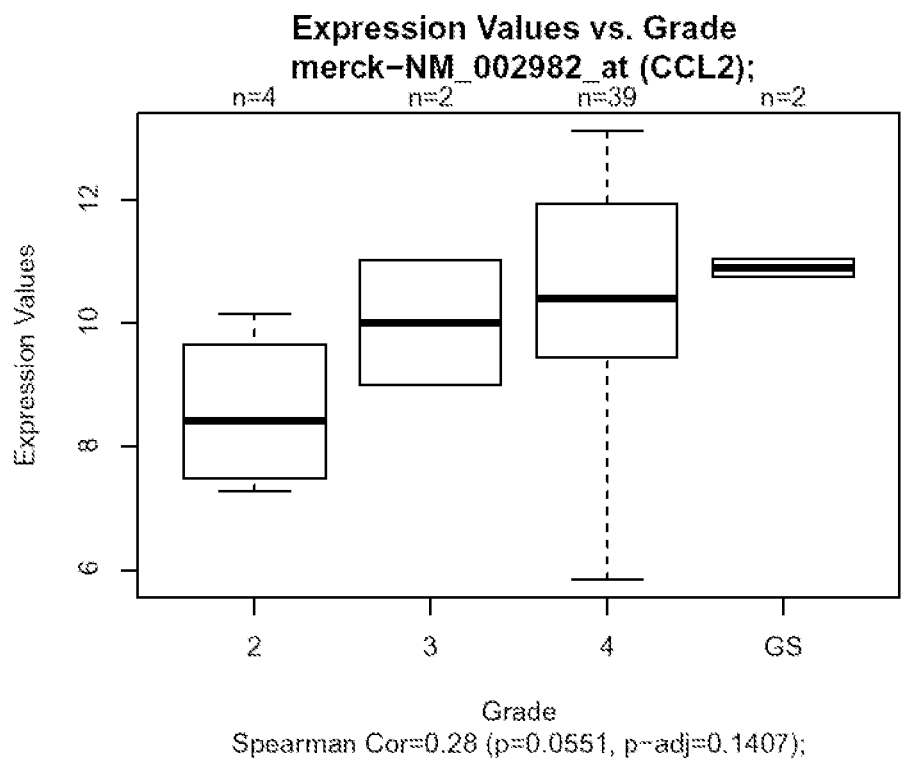
Figure 24D:
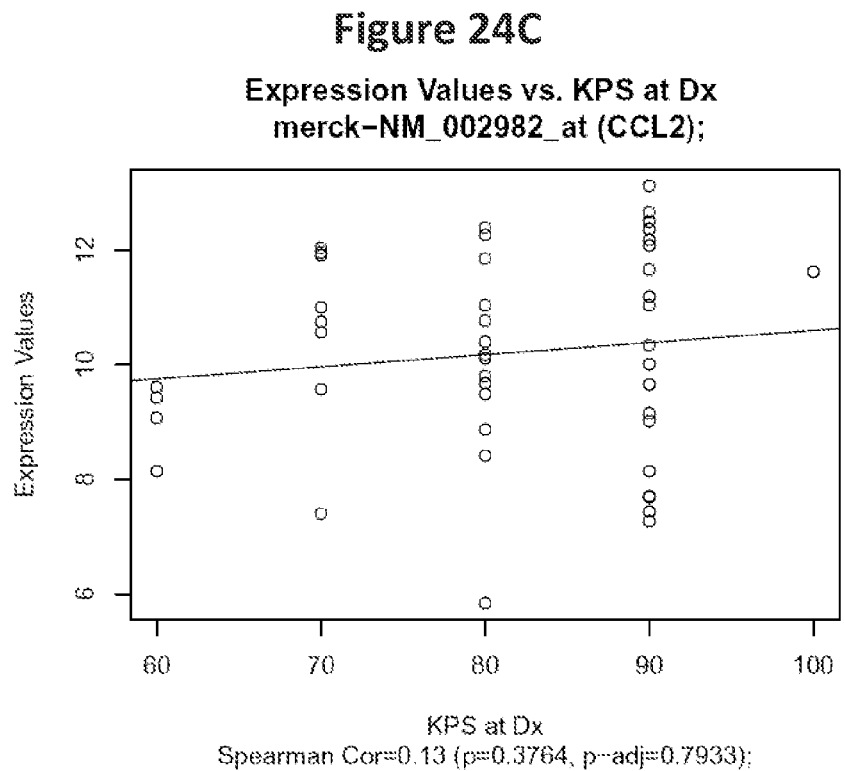
Figure 25A:
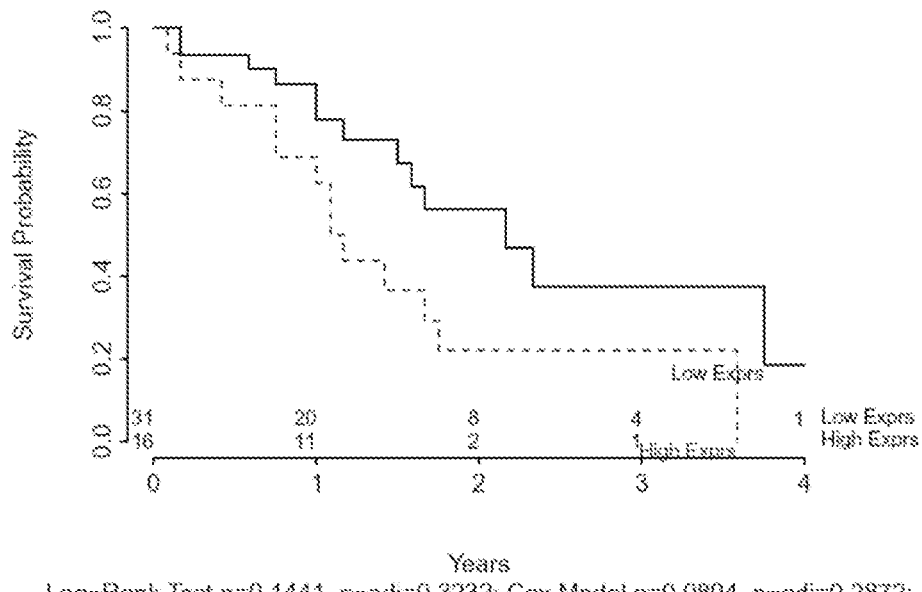
FIG. 25 is a series of images depicting the sixteenth probe set (Probe Set 16) (merck-NM_006273 at CCL7) containing the CCL7 gene. (A) a Kaplan-Meier survival curve depicting two risk groups (high and low-risk) and showing significant separation of the two survival curves. (B) graph depicting expression values versus age for CCL7. (C) graph depicting expression values versus grade for CCL7. (D) graph depicting expression values versus KPS at Dx.
Figure 25B:
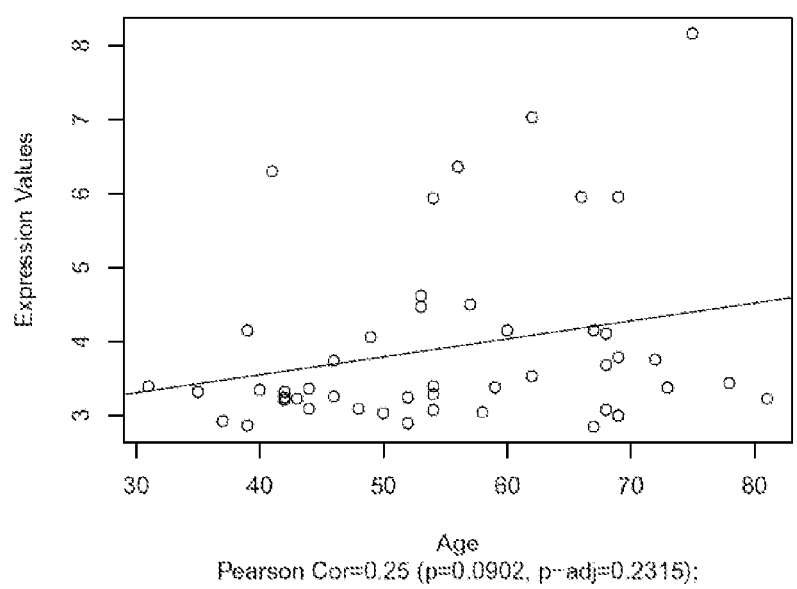
Figure 25C:
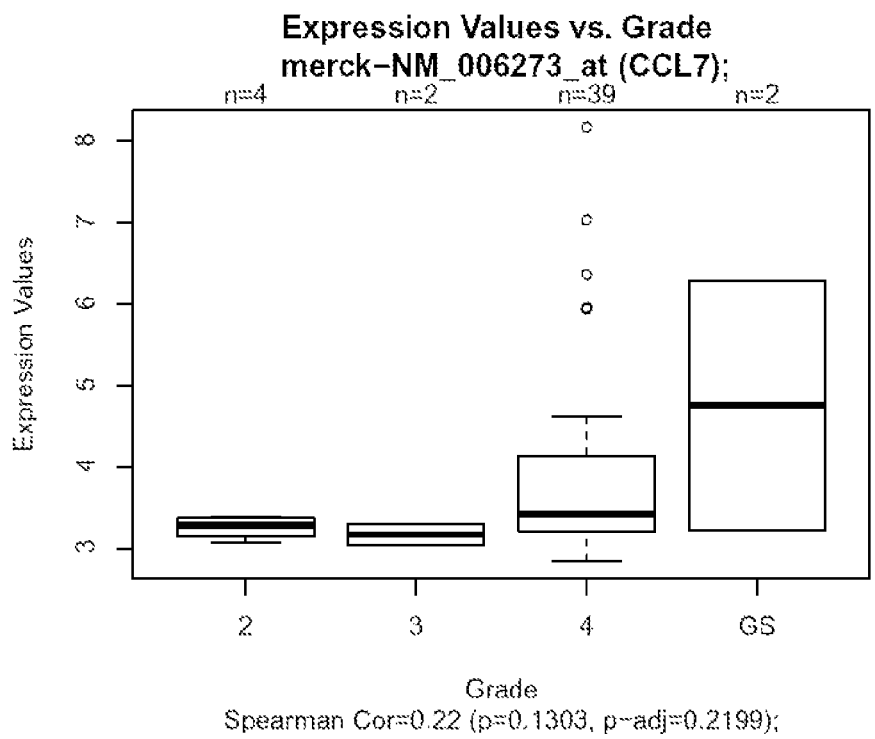
Figure 25D:
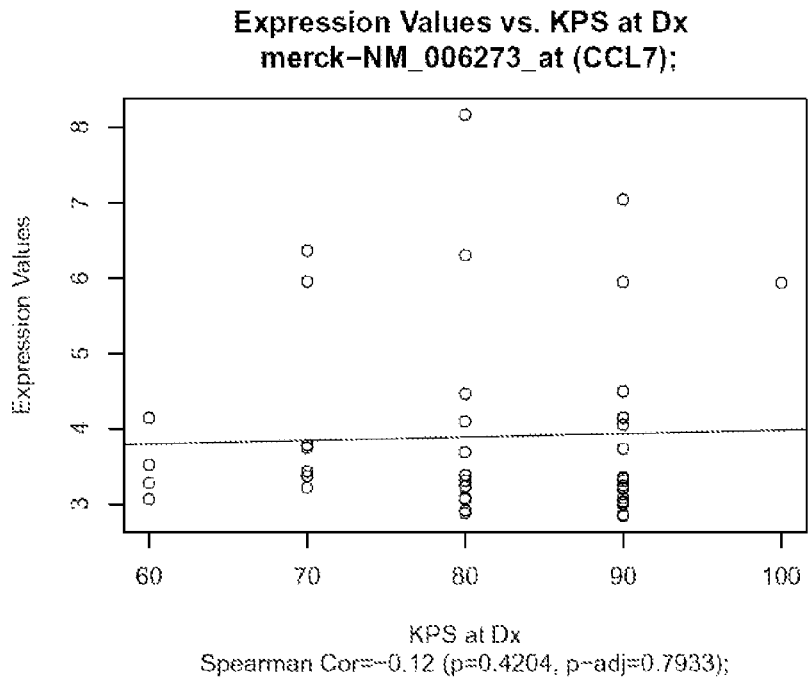
Figure 26A:
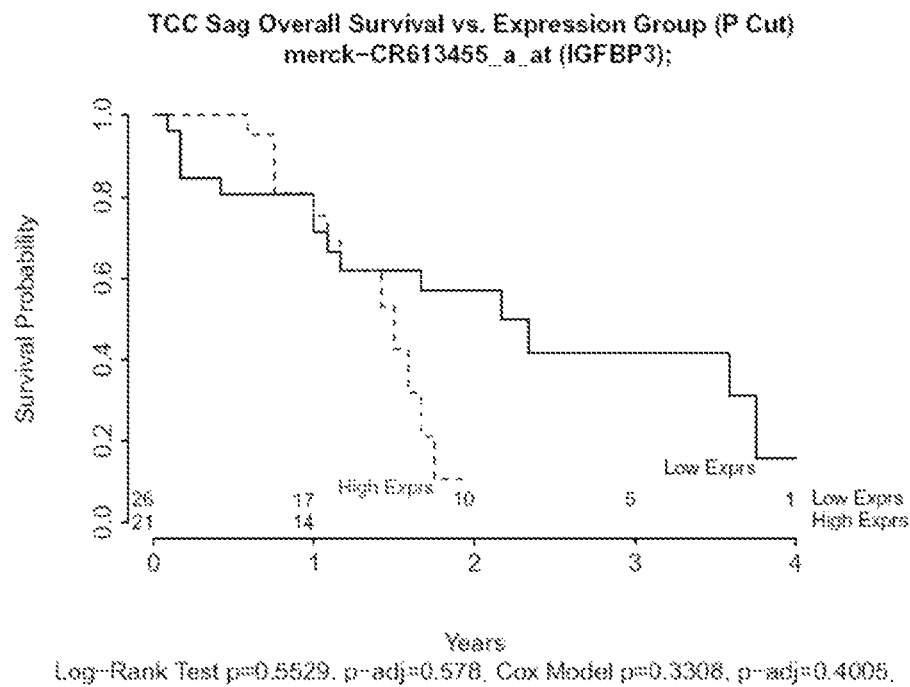
FIG. 26 is a series of images depicting the seventeenth probe set (Probe Set 17) (merck-CR613455_a_at IGFBP3) containing the IGFBP3 gene. (A) a Kaplan-Meier survival curve depicting two risk groups (high and low-risk) and showing significant separation of the two survival curves. (B) graph depicting expression values versus age for IGFBP3. (C) graph depicting expression values versus grade for IGFBP3. (D) graph depicting expression values versus KPS at Dx.
Figure 26B:
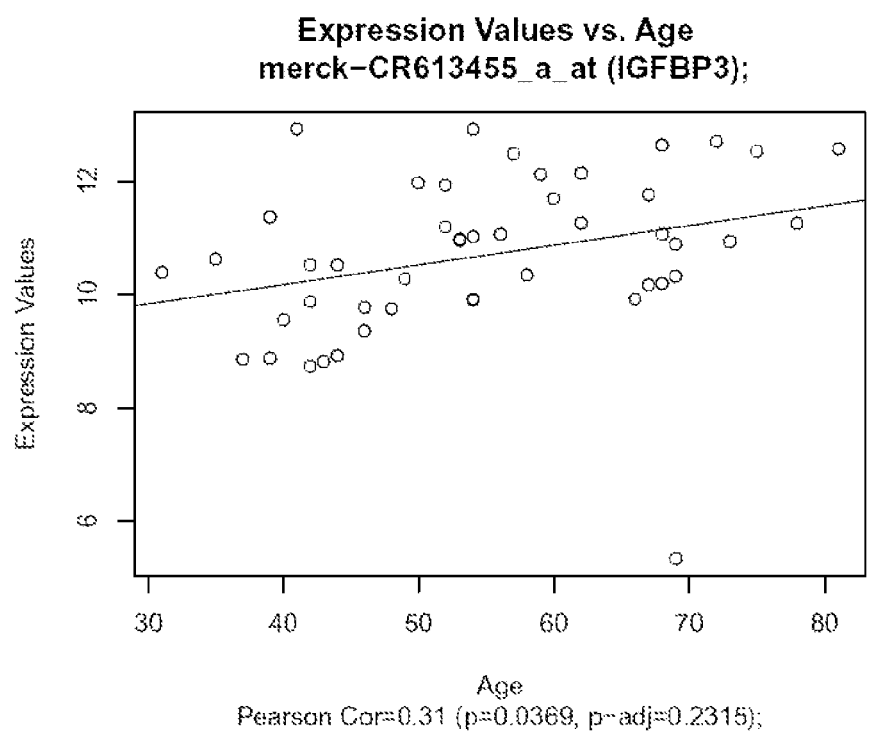
Figure 26C:
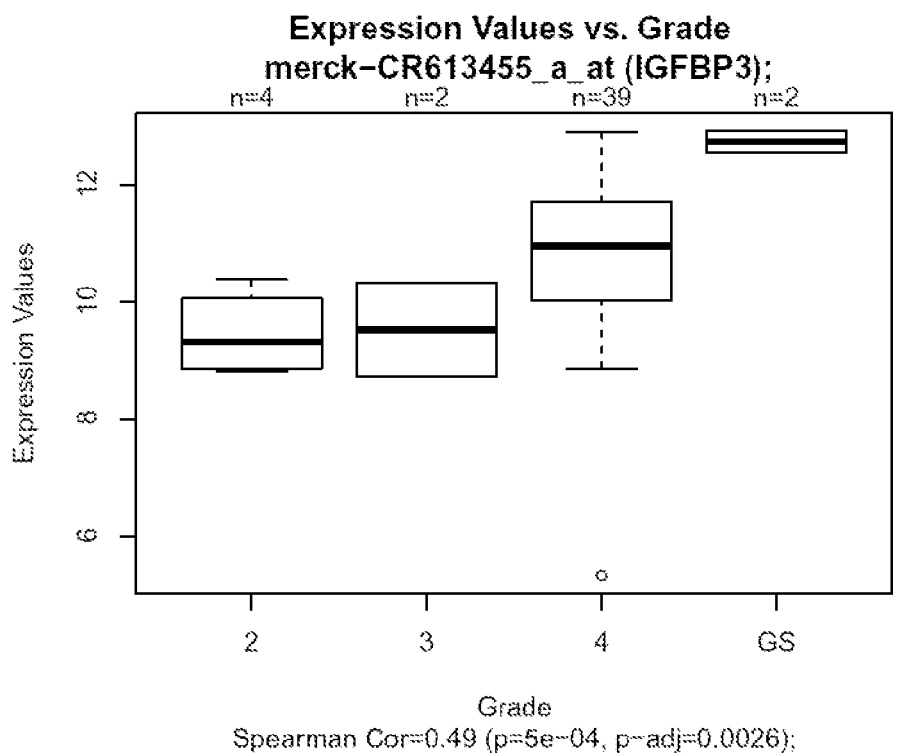
Figure 26D:
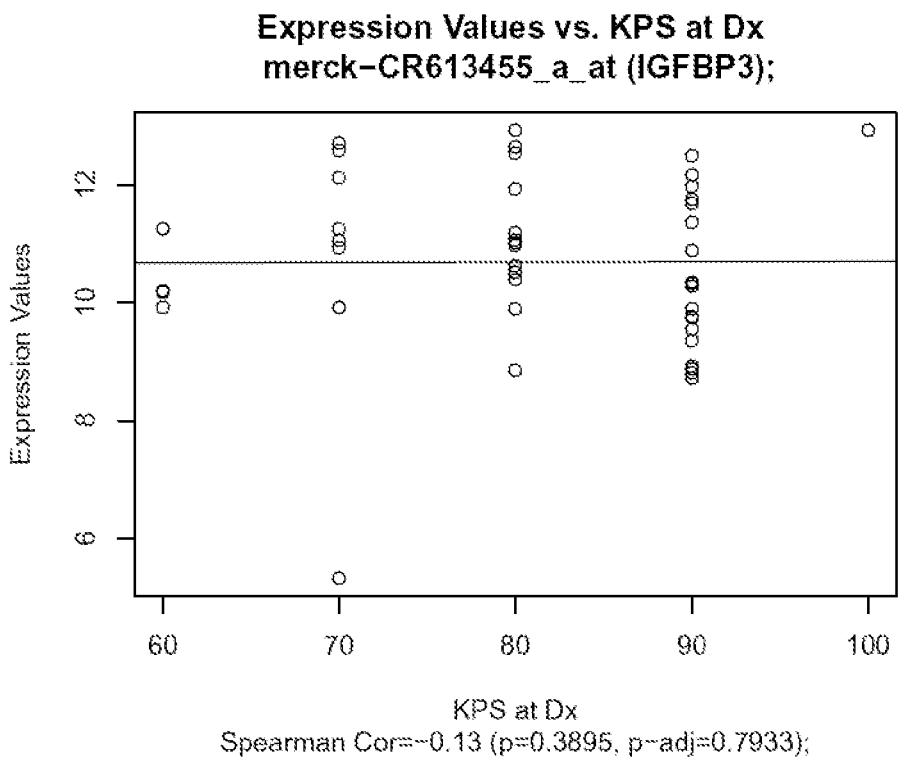
Figure 27A:
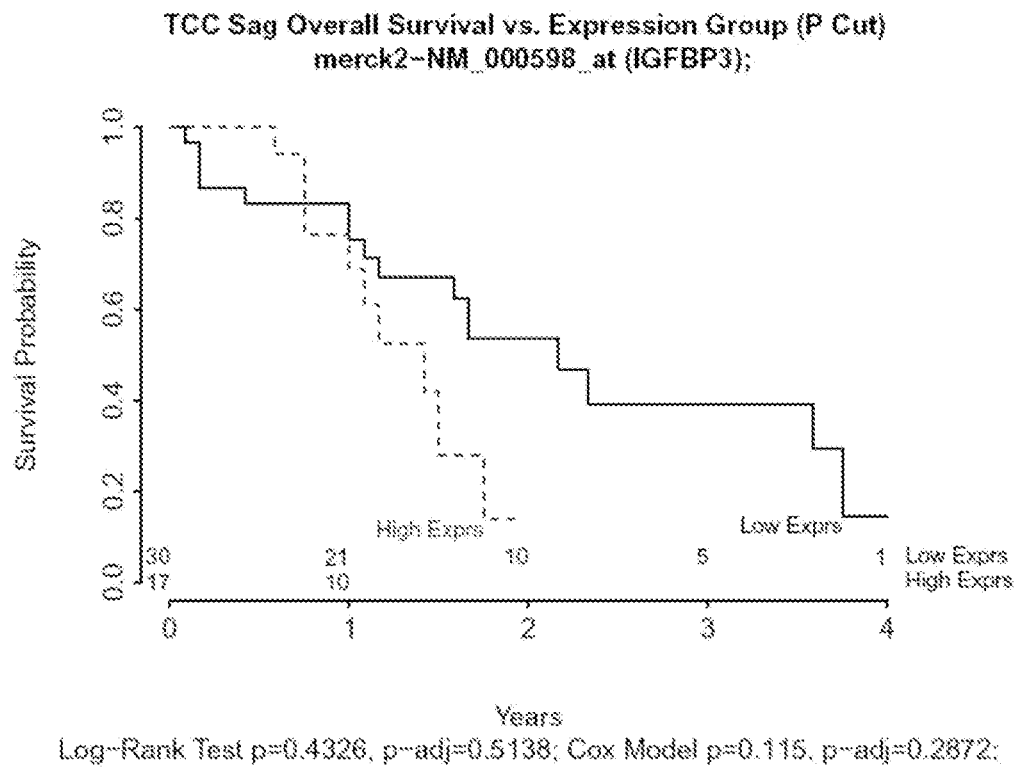
FIG. 27 is a series of images depicting the eighteenth probe set (Probe Set 18) (merck2-NM_000598 at IGFBP3) containing the IGFBP3 gene. (A) a Kaplan-Meier survival curve depicting two risk groups (high and low-risk) and showing significant separation of the two survival curves. (B) graph depicting expression values versus age for IGFBP3. (C) graph depicting expression values versus grade for IGFBP3. (D) graph depicting expression values versus KPS at Dx.
Figure 27B:
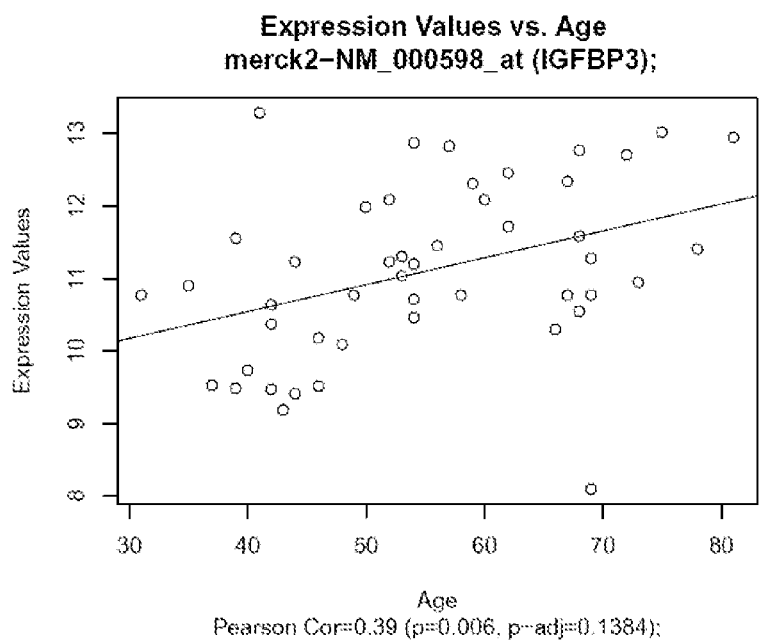
Figure 27C:
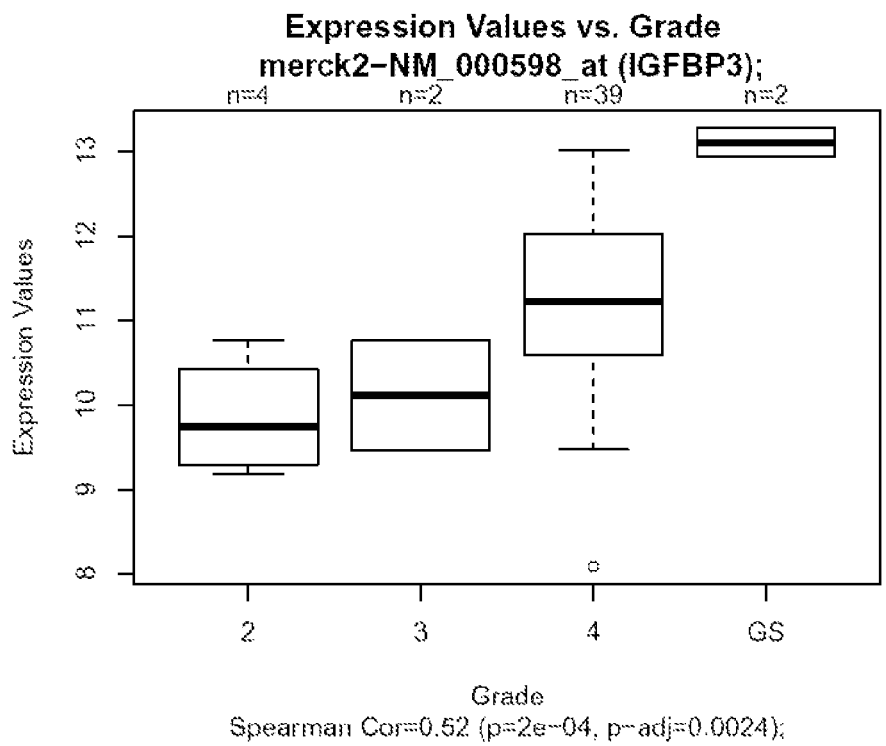
Figure 27D:
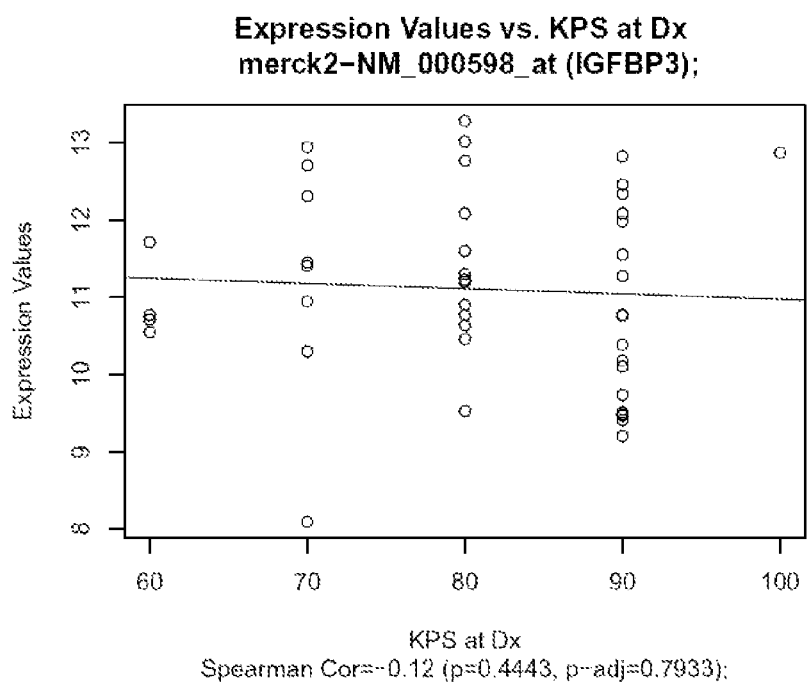
Figure 28A:
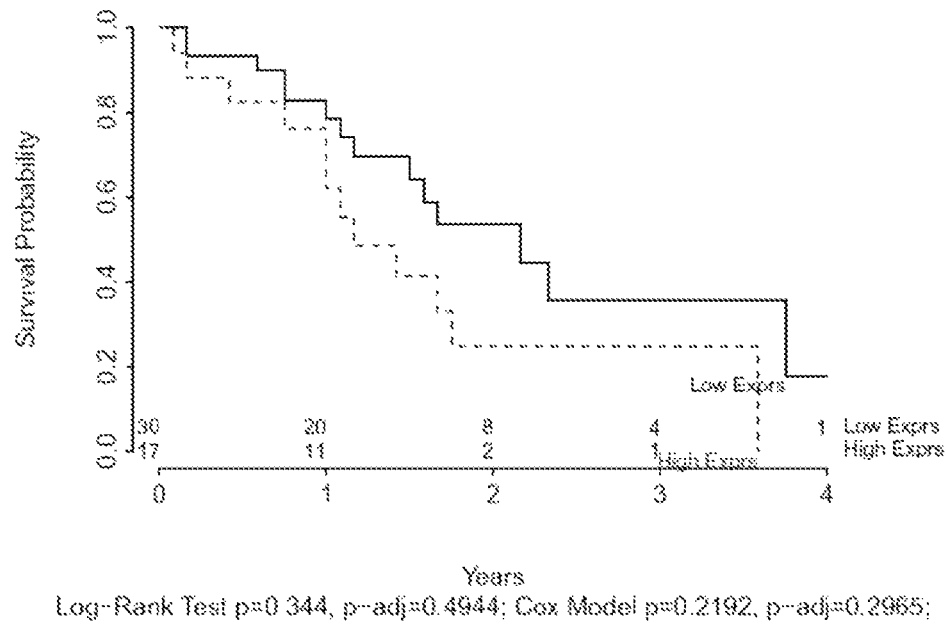
FIG. 28 is a series of images depicting the nineteenth probe set (Probe Set 19) (merck-NM_001511 at CXCL1) containing the CXCL1 gene. (A) a Kaplan-Meier survival curve depicting two risk groups (high and low-risk) and showing significant separation of the two survival curves. (B) graph depicting expression values versus age for CXCL1. (C) graph depicting expression values versus grade for CXCL1. (D) graph depicting expression values versus KPS at Dx.
Figure 28B:
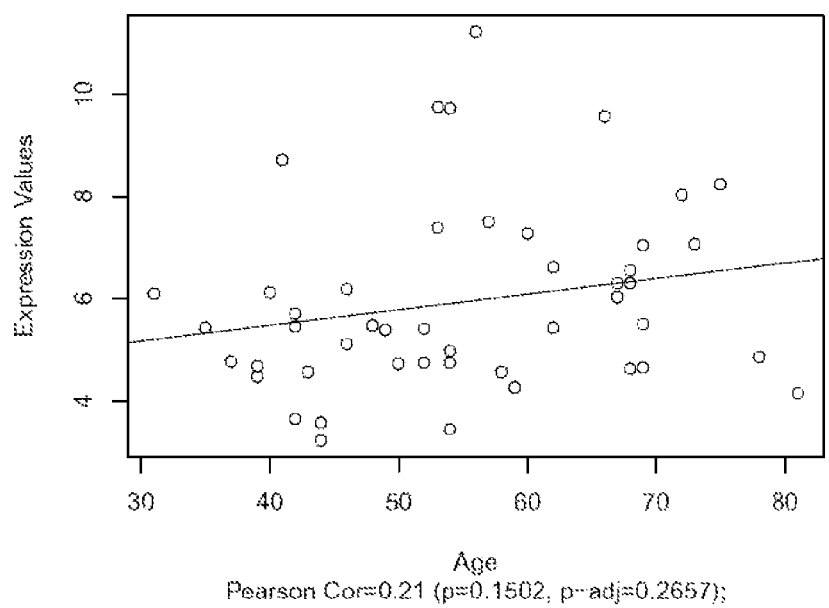
Figure 28C:
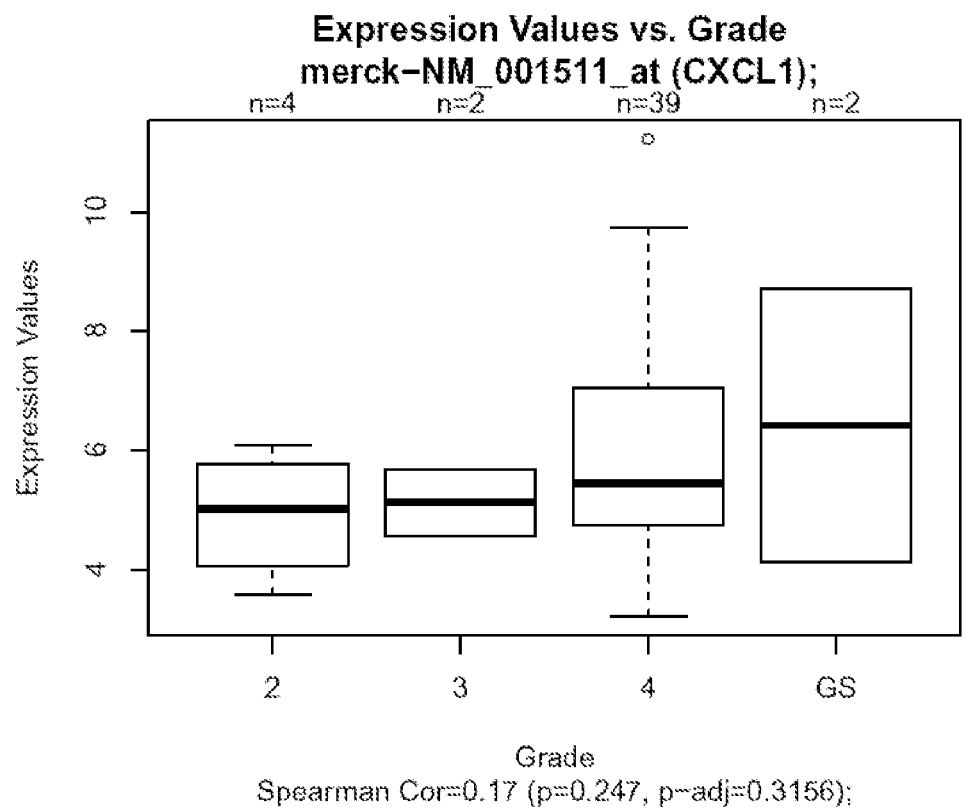
Figure 28D:
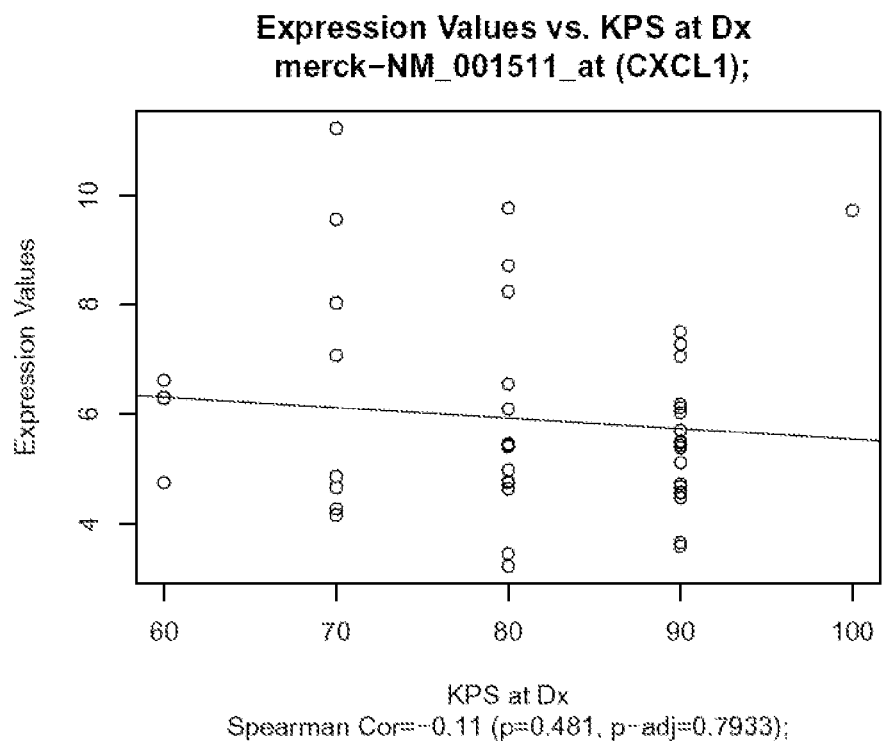
Figure 29A:
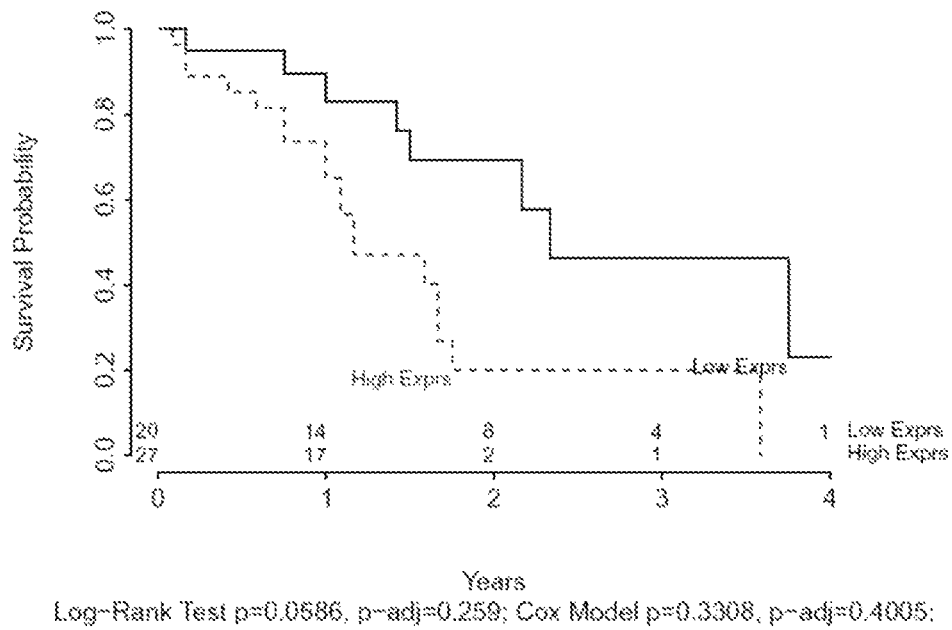
FIG. 29 is a series of images depicting the twentieth probe set (Probe Set 20) (merck-NM_006512 at SAA4) containing the SAA4 gene. (A) a Kaplan-Meier survival curve depicting two risk groups (high and low-risk) and showing significant separation of the two survival curves. (B) graph depicting expression values versus age for SAA4. (C) graph depicting expression values versus grade for SAA4. (D) graph depicting expression values versus KPS at Dx.
Figure 29B:
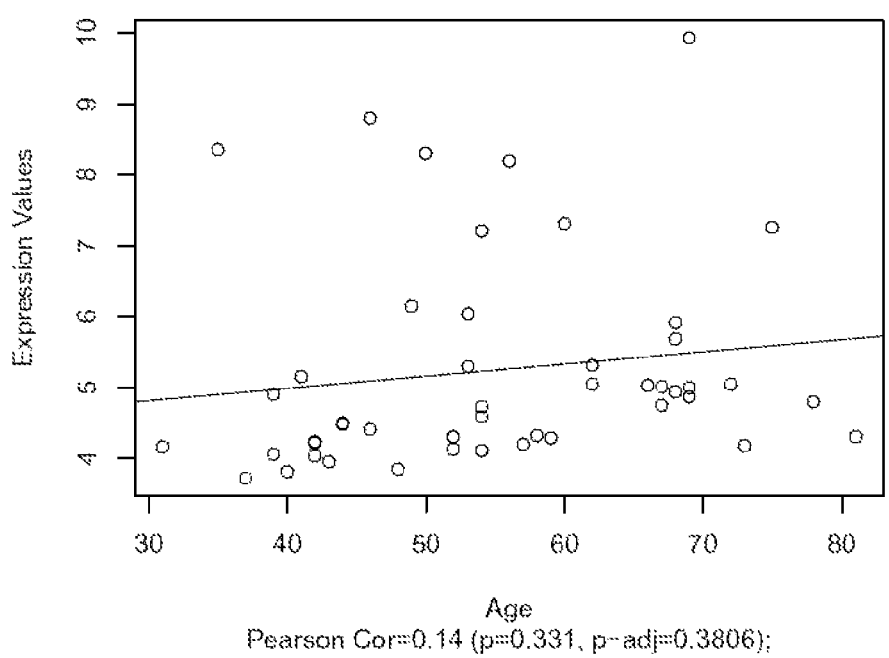
Figure 29C:
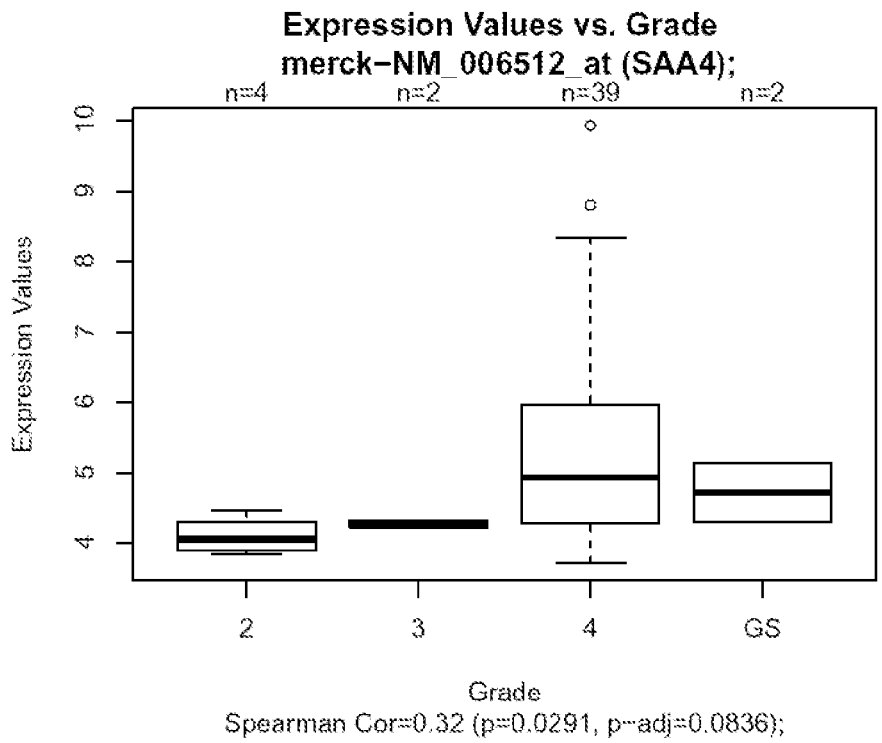
Figure 29D:
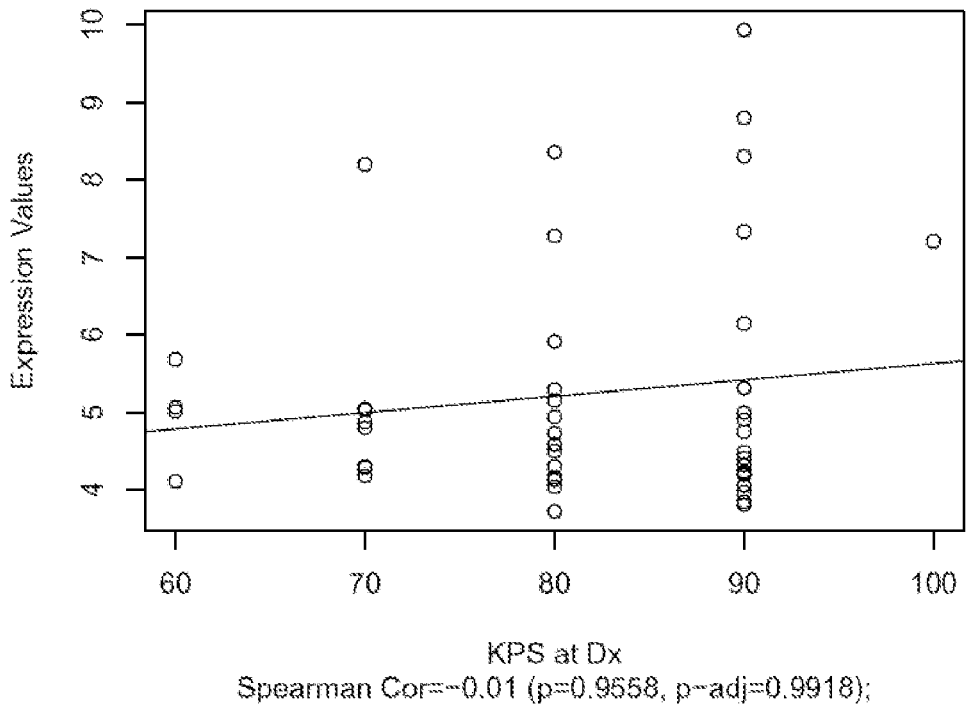
Figure 30A:
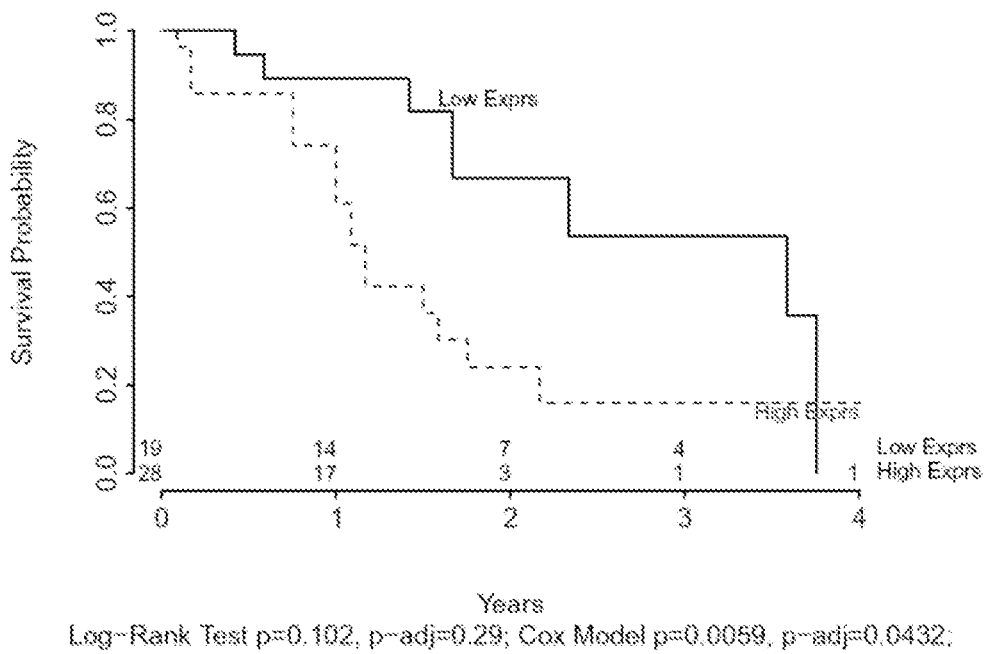
FIG. 30 is a series of images depicting the twenty-first probe set (Probe Set 21) (merck-NM_016128_at COPG) containing the COPG gene. (A) a Kaplan-Meier survival curve depicting two risk groups (high and low-risk) and showing significant separation of the two survival curves. (B) graph depicting expression values versus age for COPG. (C) graph depicting expression values versus grade for COPG. (D) graph depicting expression values versus KPS at Dx.
Figure 30B:
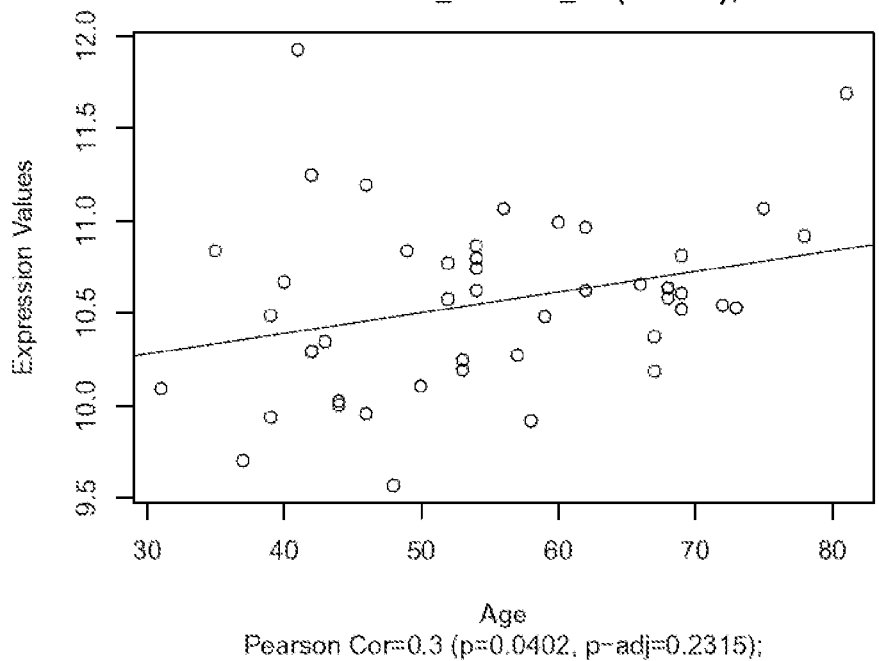
Figure 30C:
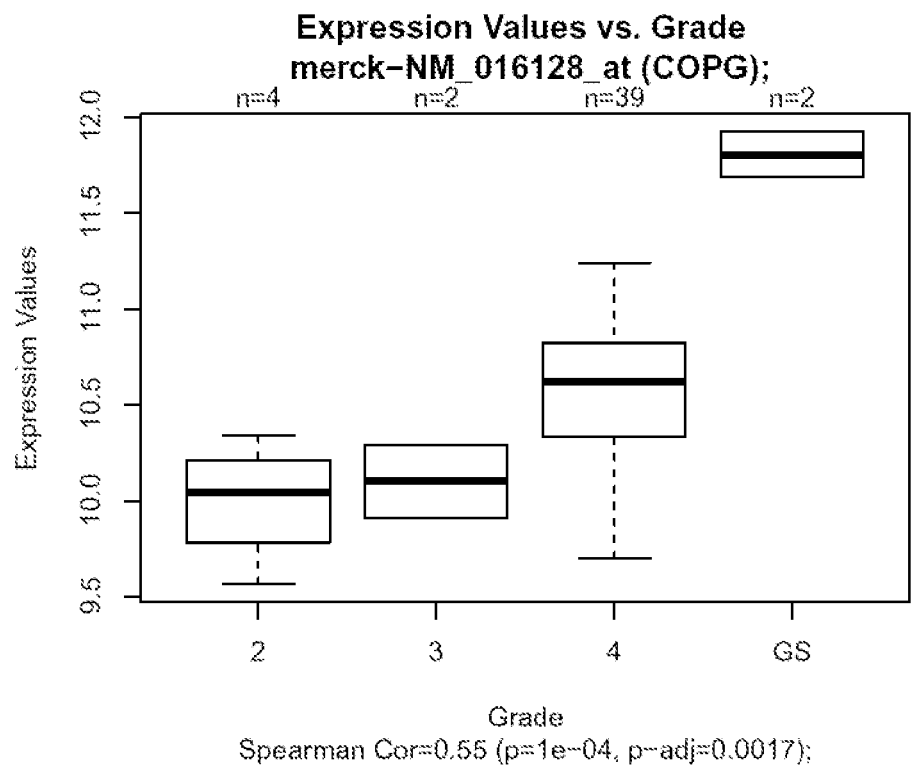
Figure 30D:
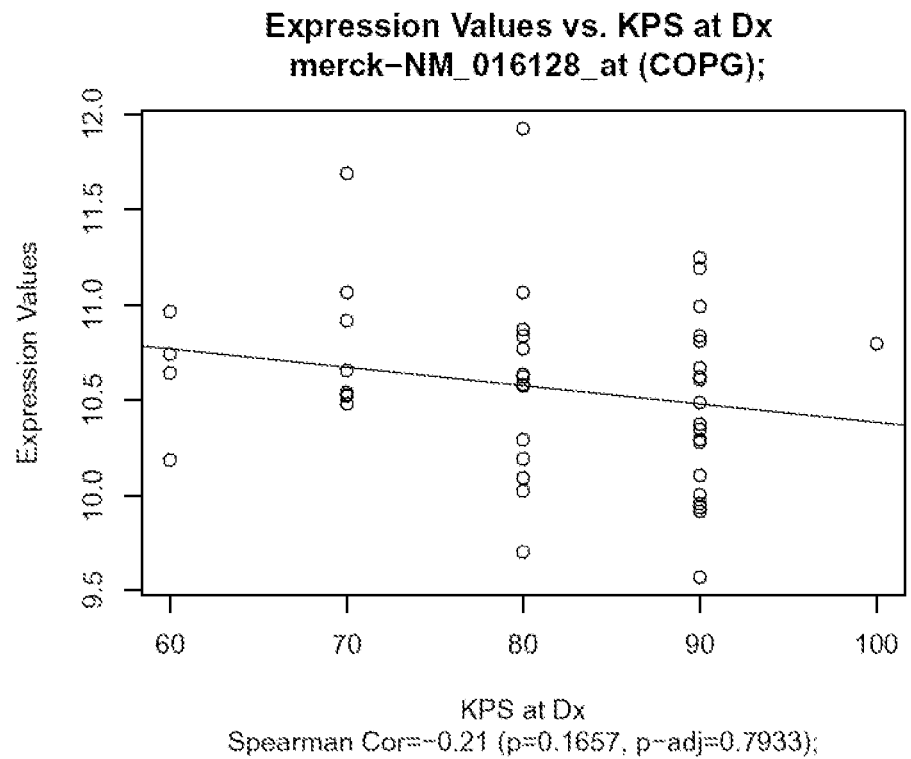
Figure 31A:
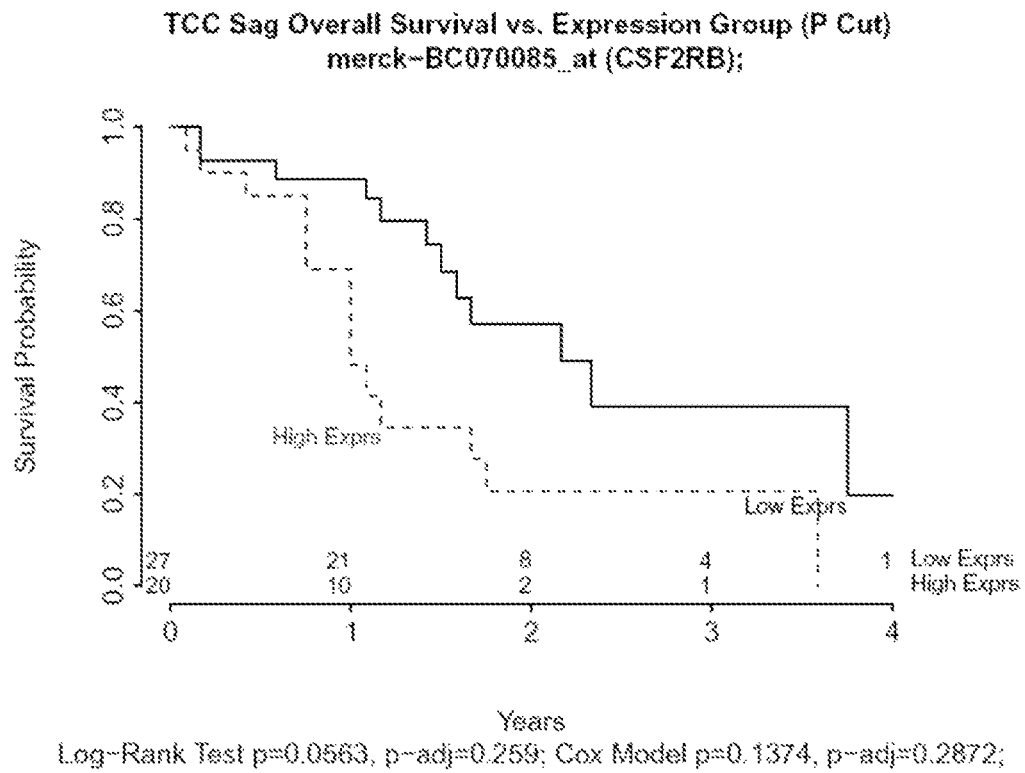
FIG. 31 is a series of images depicting the twenty-second probe set (Probe Set 22) (merck-BC070085_at CSF2RB) containing the CSF2RB gene. (A) a Kaplan-Meier survival curve depicting two risk groups (high and low-risk) and showing significant separation of the two survival curves. (B) graph depicting expression values versus age for CSF2RB. (C) graph depicting expression values versus grade for CSF2RB. (D) graph depicting expression values versus KPS at Dx.
Figure 31B:
Figure 31C:
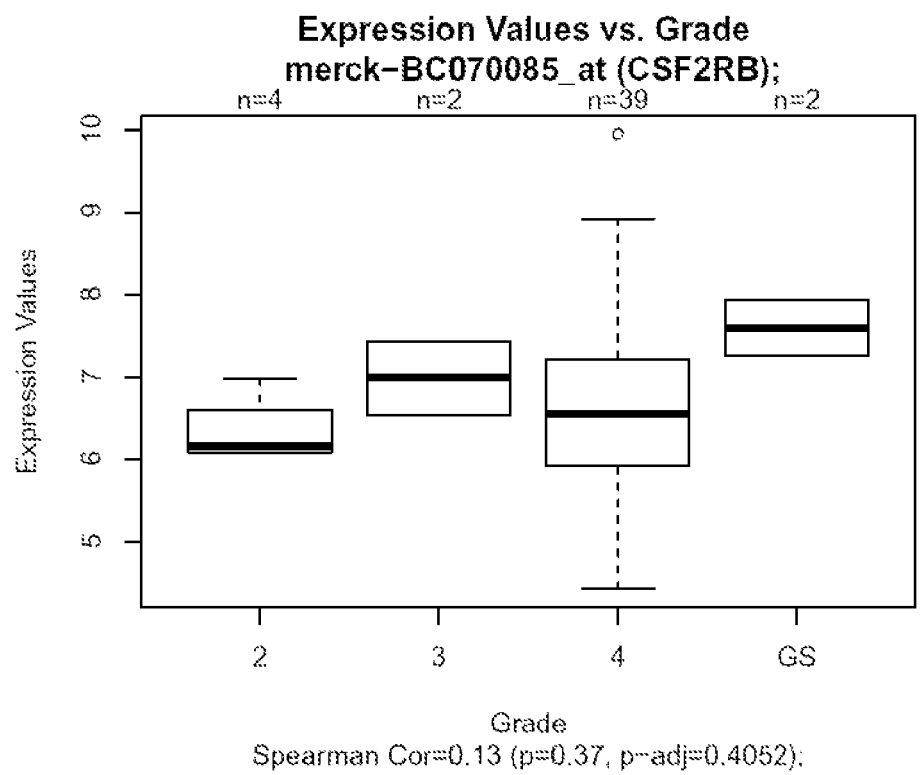
Figure 31D:
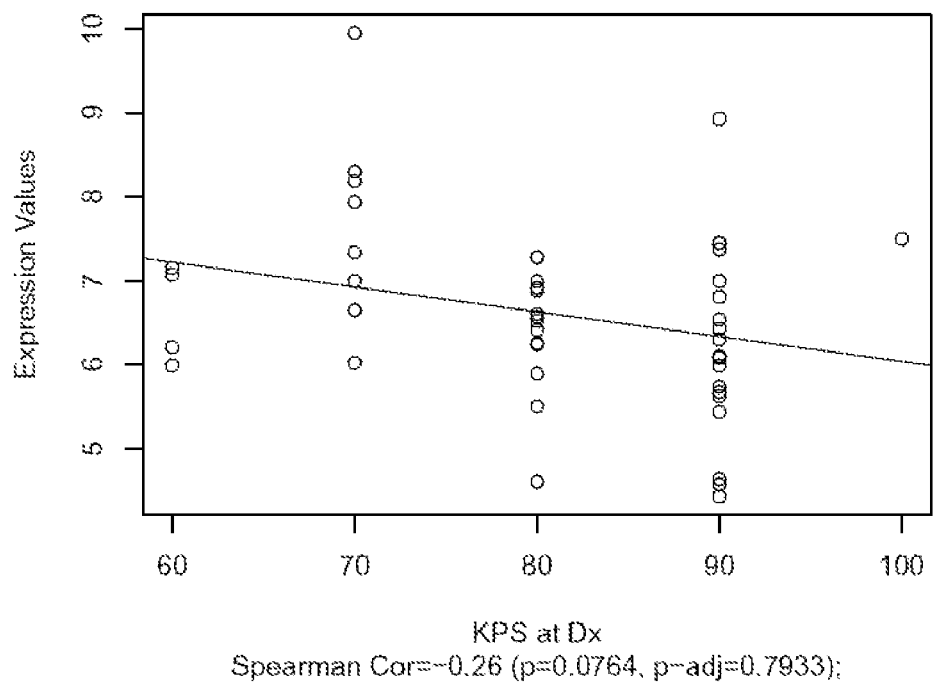
Figure 32A:
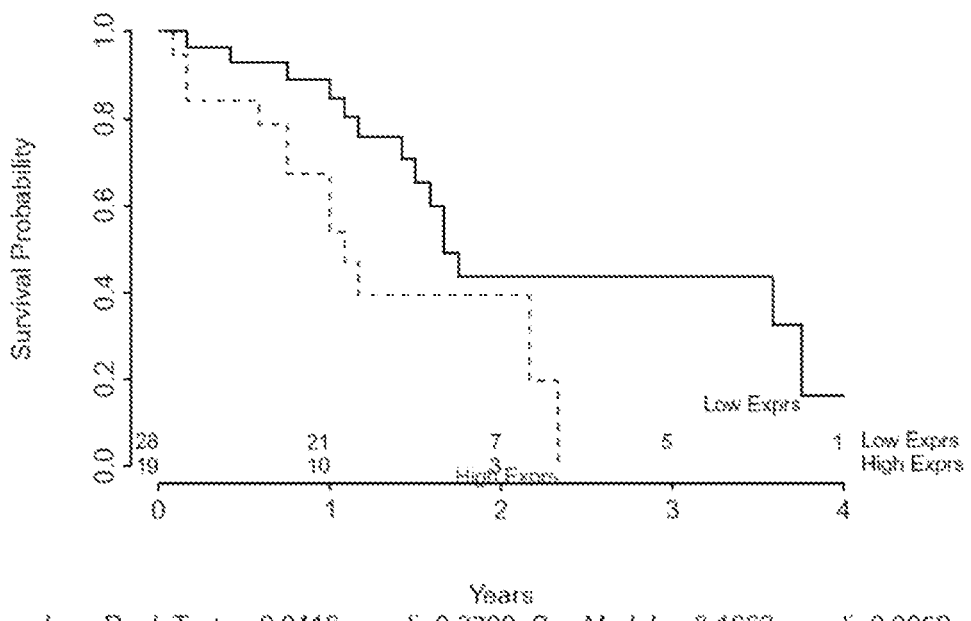
FIG. 32 is a series of images depicting the twenty-third probe set (Probe Set 23) (merck-NM_000395_a_at CSF2RB) containing the CSF2RB gene. (A) a Kaplan-Meier survival curve depicting two risk groups (high and low-risk) and showing significant separation of the two survival curves. (B) graph depicting expression values versus age for CSF2RB. (C) graph depicting expression values versus grade for CSF2RB. (D) graph depicting expression values versus KPS at Dx.
Figure 32B:
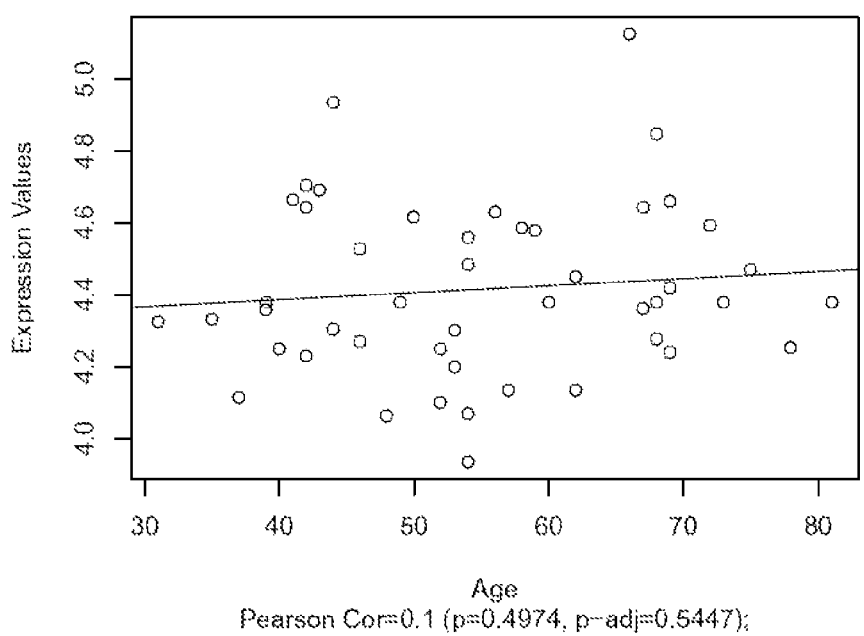
Figure 32C:
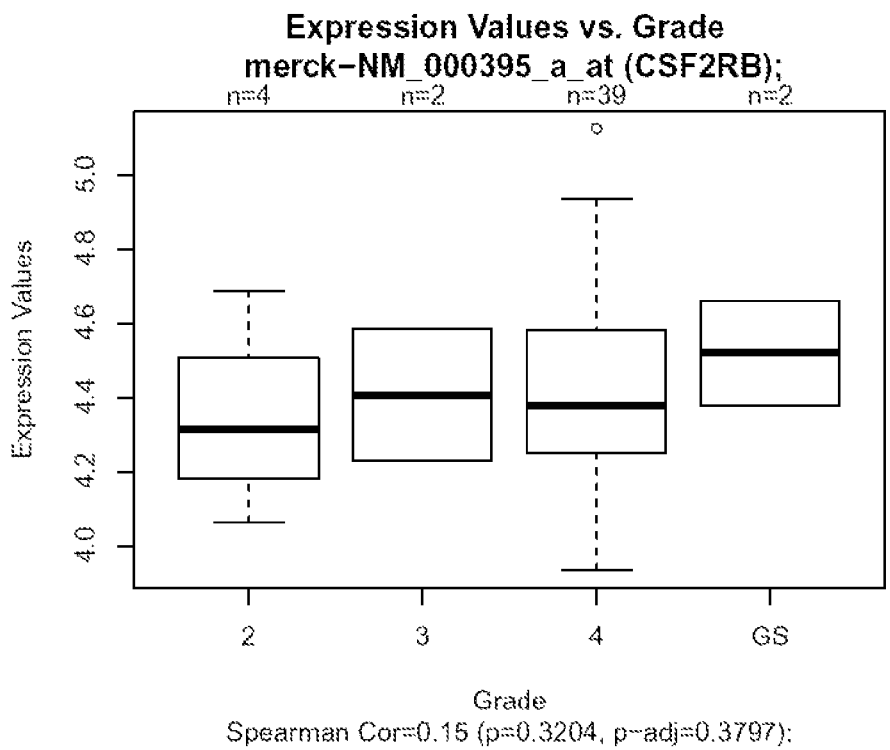
Figure 32D:
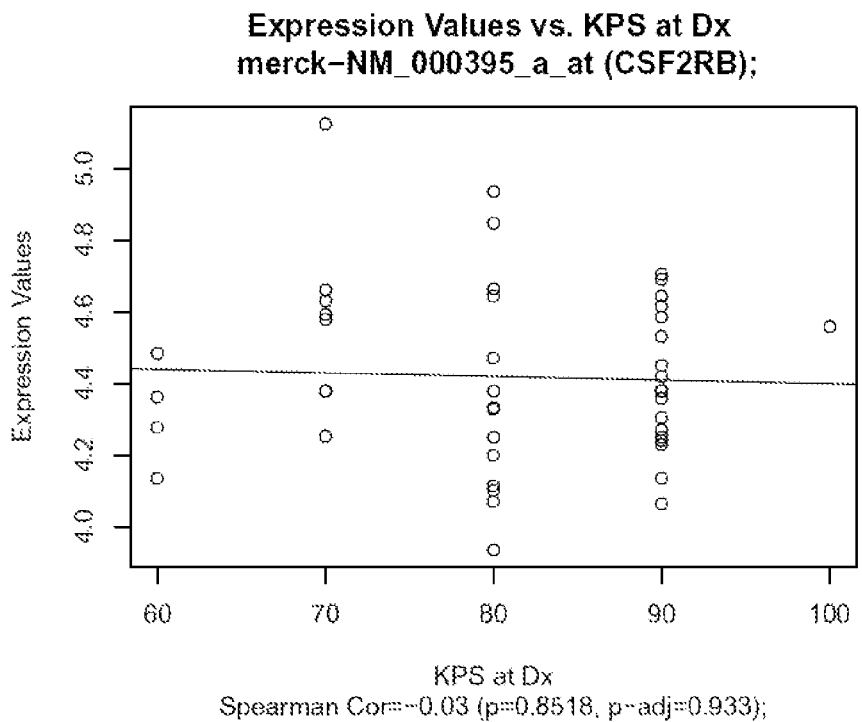

Five SAGs were significantly correlated with grade (5% FDR): COPG (r=0.55 in FIG. 8), IGFBP3 (r=0.49 and 0.52 in FIG. 9), IL6 (r=0.50 in FIG. 10C), ICAM1 (r=0.45 and 0.46 in FIG. 7), and IL8 (r=0.38 in FIG. 11C).

None of SAGs were significantly correlated with age at 5% FDR.

Given the results obtained, the inventors demonstrate a SAG signature in high grade glioma that is associated with age at onset and patient outcome. This signature is comprised of genes involved in cell cycle regulation, apoptosis, cell proliferation, and angiogenesis and may define a more aggressive subtype of high-grade glioma. While the inventors examined the genes (specifically probe sets containing RNA transcripts) associated with high grade gliomas, one of ordinary skill in the art would recognize that the polynucleotides and gene products such as polypeptides of SAG can also serve as biomarkers in the present invention.

The inventors have demonstrated that an increase of expression of SAG is associated with high grade gliomas and is correlated to a poor prognosis. Given these findings, SAG can be used as biomarkers to predict the response of high grade gliomas to therapy. In this embodiment, an expression level of at least one SAG or gene expression product is obtained from a sample. This expression level is compared to a predetermined control expression level. Using the comparison between these expression levels a determination is made regarding the likelihood of a favorable response to therapy.

EXAMPLE 2

SAG can be used as biomarkers to diagnose neoplasia such as high grade gliomas. In this embodiment, an expression level of at least one SAG is obtained from a sample and is compared to a control expression level. An increase in the expression level of SAG obtained from the sample can indicate a diagnosis of high grade glioma.

EXAMPLE 3

SAG can also be used to monitor the progression of a high grade glioma from one biological state to another. In this embodiment, an expression level of at least one SAG is obtained from a tumor sample at a first timepoint. A second expression level is obtained from the tumor sample at a second timepoint that is at a predetermined interval after the first timepoint. The expression levels are compared and an increase in expression level from the first timepoint to the second timepoint indicates disease progression while a decrease in expression level from the first timepoint to the second timepoint indicates disease regression.

EXAMPLE 4

SAG biomarkers can be used to evaluate the efficacy of a given therapeutic agent on high grade gliomas. In this embodiment, an expression level of at least one SAG is obtained from a tumor sample at a first timepoint prior to any agent being administered. Once the initial expression level is taken, a therapeutically effective amount of an agent can be administered to the subject. At a second timepoint, which occurs at a given interval after the first timepoint and after the administration of the agent, a second expression level is obtained from the tumor sample. The expression levels of the sample are compared and an increase in expression level from the first timepoint to the second timepoint indicates the agent is ineffective for treating high grade gliomas while a decrease in expression level from the first timepoint to the second timepoint indicates the agent is effective for treating high grade gliomas. If the agent is deemed ineffective, studies can be conducted to determine if it is the agent itself that is ineffective or if the dose of the agent administered needs to be adjusted.

Test compounds or agents that are believed to be capable of modulating the activity of any of the biomarkers of the present invention may be administered to subjects who are suffering from or at risk of developing cancer, particularly high grade gliomas. In the present invention, the administration of an agent which decreases the activity of a particular biomarker may decrease the risk of high grade glioma in a subject since the increased activity of the biomarker is at least partly responsible for the onset of neoplasia such as high grade gliomas.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of predicting the response of a subject to therapy for high grade glioma comprising:
    obtaining an expression level of at least one gene or gene expression product in a tumor sample;
    comparing the expression level of the at least one gene or gene expression product to a predetermined control expression level;
    determining a therapeutic response based on the comparison of the expression level of the at least one gene or gene expression product obtained from the tumor sample to the predetermined control expression level;
    obtaining a senescence score for the at least one gene or gene expression product; and
    associating the senescence score with patient survival using statistical methods.

2. The method of claim 1, wherein the at least one gene is a senescence associated gene (SAG).

3. The method of claim 1, wherein the at least one gene expression product is derived from an SAG.

4. The method of claim 1, wherein the at least one gene is selected from the group consisting of CCL2, CCL7, CDKN1A, COPG, CSF2RB, CXCL1, ICAM1, IGFBP3, IL6, IL8, SAA4, TNFRSF11B, TNFSF11 and TP53.

5. The method of claim 1, wherein the at least one gene is selected from the group consisting of IL6, ICAM1, COPG, IL8, IGFBP-3 and TNFSF11.

6. The method of claim 1, wherein the high grade glioma is selected from the group consisting of gliomas, astrocytomas, oligodendrogliomas, anaplastic oligodendrogliomas, and glioblastomas.

7. The method of claim 1, wherein the high grade glioma is a glioblastoma.

8. A method of diagnosing neoplasia comprising:
obtaining an expression level of at least one senescence associated gene (SAG) or gene expression product in a sample;
generating a senescence score for the at least one senescence associated gene or gene expression product; and
comparing the senescence score of the at least one SAG or gene expression product to a predetermined control senescence score;
wherein a higher senescence score of the at least one SAG or gene expression product as compared to the predetermined control senescence score indicates the presence of neoplasia.

9. The method of claim 8, wherein the neoplasia is a high grade glioma.

10. The method of claim 8, wherein the neoplasia is selected from the group consisting of gliomas, astrocytomas, oligodendrogliomas, anaplastic oligodendrogliomas, glioblastomas, neuroblastomas, and meningiomas.

11. The method of claim 8, wherein the neoplasia is a glioblastoma.

12. The method of claim 8, wherein the at least one gene is selected from the group consisting of CCL2, CCL7, CDKN1A, COPG, CSF2RB, CXCL1, ICAM1, IGFBP3, IL6, IL8, SAA4, TNFRSF11B, TNFSF11 and TP53.

13. A method of monitoring neoplasia progression from one biological state to another in a tumor sample comprising:
detecting a first expression level of at least one gene or gene expression product in a tumor sample at a first timepoint;
generating a first senescence score for the at least one senescence associated gene or gene expression product at the first timepoint;
detecting a second expression level of the at least one gene or gene expression product in the tumor sample at a second time point wherein the second timepoint is at a given interval after the first timepoint;
generating a second senescence score for the at least one senescence associated gene or gene expression product at the second timepoint; and
comparing the first and the second senescence scores to each other;
wherein an increase in the second senescence score as compared to the first senescence score is indicative of neoplasia progression and a decrease in the second senescence score as compared to the first senescence score is indicative of neoplasia regression.

14. The method of claim 13, wherein the neoplasia is a high grade glioma.

15. The method of claim 13, wherein the neoplasia is selected from the group consisting of gliomas, astrocytomas, oligodendrogliomas, anaplastic oligodendrogliomas, glioblastomas, neuroblastomas, and meningiomas.

16. The method of claim 13, wherein the neoplasia is a glioblastoma.

17. The method of claim 13, wherein the at least one gene is a senescence associated gene (SAG).

18. The method of claim 13, wherein the at least one gene expression product is derived from an SAG.

19. The method of claim 13, wherein the at least one gene is selected from the group consisting of CCL2, CCL7, CDKN1A, COPG, CSF2RB, CXCL1, ICAM1, IGFBP3, IL6, IL8, SAA4, TNFRSF11B, TNFSF11 and TP53.

20. A method for evaluating the efficacy of an agent for modulating a senescence associated gene (SAG) comprising:
detecting a first expression level of at least one senescence associated gene (SAG) or gene expression product in a tumor sample at a first timepoint;
generating a first senescence score for the at least one senescence associated gene or gene expression product at the first timepoint;
administering a therapeutically effective amount of the agent to the tumor sample;
detecting a second expression level of the at least one senescence associated gene or gene expression product in the tumor sample at a second timepoint wherein the second timepoint is at a given interval after the first timepoint and after the administration of the agent;
generating a second senescence score for the at least one senescence associated gene or gene expression product at the second timepoint; and
comparing the first senescence score to the second senescence score;
wherein a decrease in the second senescence score as compared to the first senescence score indicates the agent is efficacious for modulating the senescence associated gene.

21. The method of claim 20, wherein the at least one gene is selected from the group consisting of CCL2, CCL7, CDKN1A, COPG, CSF2RB, CXCL1, ICAM1, IGFBP3, IL6, IL8, SAA4, TNFRSF11B, TNFSF11 and TP53.

* * * * *